(12) United States Patent
Talukdar et al.

(10) Patent No.: US 12,172,991 B2
(45) Date of Patent: Dec. 24, 2024

(54) BICYCLE TOPOISOMERASE I INHIBITING COMPOUNDS, PROCESS FOR PREPARATION AND USE THEREOF

(71) Applicants: Council of Scientific & Industrial Research, New Delhi (IN); Indian Association for the Cultivation of Science, Kolkat (IN)

(72) Inventors: Arindam Talukdar, Kolkata (IN); Benu Brata Das, Kolkata (IN); Biswajit Kundu, Kolkata (IN); Subhendu K. Das, Kolkata (IN); Chowdhuri Srijita Paul, Kolkata (IN); Dipayan Sarkar, Kolkata (IN); Sourav Pal, Kolkata (IN); Debomita Bhattacharya, Kolkata (IN); Ayan Mukherjee, Kolkata (IN); Subhajit Roy, Kolkata (IN)

(73) Assignees: Council of Scientific & Industrial Research, New Delhi (IN); Indian Association for the Cultivation of Science, Kolkata (IN)

( * ) Notice: Subject to any disclaimer, the term of this patent is extended or adjusted under 35 U.S.C. 154(b) by 912 days.

(21) Appl. No.: 17/059,289

(22) PCT Filed: May 24, 2019

(86) PCT No.: PCT/IN2019/050410
§ 371 (c)(1),
(2) Date: Nov. 27, 2020

(87) PCT Pub. No.: WO2019/229765
PCT Pub. Date: Dec. 5, 2019

(65) Prior Publication Data
US 2021/0246128 A1    Aug. 12, 2021

(30) Foreign Application Priority Data
May 29, 2018    (IN) .............................. 201811020003

(51) Int. Cl.
*C07D 413/14*    (2006.01)
*C07D 413/04*    (2006.01)
*C07D 491/22*    (2006.01)

(52) U.S. Cl.
CPC ......... *C07D 413/14* (2013.01); *C07D 413/04* (2013.01); *C07D 491/22* (2013.01)

(58) Field of Classification Search
CPC ........................... C07D 401/01; C07D 413/14
See application file for complete search history.

(56) References Cited

U.S. PATENT DOCUMENTS 7,312,228 B2    12/2007    Cushman et al.

FOREIGN PATENT DOCUMENTS

| WO | WO-2012/135759 A1 | | 10/2012 | |
|----|----|----|----|----|
| WO | WO2018/013676 | * | 1/2018 | .......... C07D 401/04 |
| WO | WO-2018/013676 A1 | | 1/2018 | |

OTHER PUBLICATIONS

International Search Report & Written Opinion for PCT/IN2019/050410, dated Aug. 7, 2019, 10 pgs.
M. Goodman, et al., "Plant Antitumor Agents. I. The Isolation and Structure of Camptothecin, a Novel Alkaloidal Leukimia and Tumor Inhibitor from *Camptotheca acuminate*", Journal of the American Chemical Society, Aug. 20, 1966, pp. 3888-3890.
D. Strumberg, et al., "Synthesis of Cytotoxic Indenoisoquinoline Topoisomerase I Poisons", J. Med. Chem., 1999, vol. 42, pp. 446-457.
Y. Pommier, "Topoisomerase I Inhibitors: Camptothecins and Beyond", Nature Reviews, www.nature.com/reviews/cancer, vol. 6, Oct. 2006, pp. 789-802.
"International Journal of Scientific and Research Publications", vol. 3, Issue 8, Aug. 2013 Edition, www.ijsrp.org, 896 pgs.

* cited by examiner

*Primary Examiner* — Paul V Ward
(74) *Attorney, Agent, or Firm* — BLANK ROME LLP

(57) ABSTRACT

The invention described herein relates to the compounds of Formula I for treating diseases and disorders for which inhibition or modulation of the topoisomerase I enzyme produces a physiologically beneficial response, in particular for the treatment of breast cancer. Also provided is the process of preparing compounds of Formula I.

12 Claims, 6 Drawing Sheets

A

B

C

BICYCLE TOPOISOMERASE I INHIBITING COMPOUNDS, PROCESS FOR PREPARATION AND USE THEREOF

RELATED APPLICATIONS

This application is a national phase application of International Application No. PCT/IN2019/050410, filed May 24, 2019, which claims the benefit of Indian Patent Application No. 201811020003, filed on May 29, 2018. The entire contents of these applications are hereby incorporated by reference.

FIELD OF INVENTION

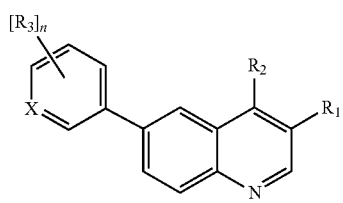

Formula I

The present invention relates to a compound with formula I in free form or in acceptable salt form as topoisomerase I inhibitors.

The invention relates to small molecules where $R_1$, $R_2$, $R_3$, n and X are as defined in the description, which together possess the ability to increase the stability of the drug-DNA-Topoisomerase I ternary complex that eventually results in cancer cell death to achieve clinical anticancer activity.

BACKGROUND OF THE INVENTION

Chemotherapy is used to treat many types of cancer by stopping or slowing the growth of cancer cells. The discovery of small molecule targeting specific cellular processes in the proliferation of cancer cells is currently very active research area for cure and control of cancer. During the DNA replication the supercoiled DNA double helix is pulled apart into two strands. Enzyme topoisomerase I ('TopI') can typically perform the DNA strand break by binding to double-stranded DNA and cut the phosphate backbone of one of the DNA strands. Top I form a transient covalent bond with the 3'-phosphate end of the cleaved DNA strand by attacking the phosphodiester backbone of the DNA. These covalent intermediates are generally referred to as TopI-cleavage complexes (TopIcc). Subsequent strand passage through the break leads to DNA relaxation followed by strand religation. Agents that inhibit the function of the Top I can cause death of the dividing cell. Cancer cells are more vulnerable to Top I inhibition than normal cell since cancer cells grow and replicate at a much faster rate. In various tumor cells, Top I is expressed much higher than the normal cells; hence, modulating the Top I levels in tumor cells to block DNA replication and cell division has made it an attractive drug target for anticancer therapy.

In general, TopI poisons exhibit their antitumor activities by stabilizing the TopI-DNA cleavage complexes. Camptothecin a natural product isolated from the Chinese tree was the first small molecule to be identified as a Top I inhibitor (G. A. Sim, *J. Am. Chem. Soc.* 1966, 88, 3888-3890). Later, topotecan and irinotecan two camptothecin derivatives were developed and clinically marketed anticancer drug, which emphasizes the significance of Top I as a drug target (Pommier. Y, *Nat. Rev. Cancer,* 2006, 6, 789-802). However, topotecan and irinotecan are not ideal drug molecules as they possess inherently unstable chemical structure due to opening of the lactone ring present in these compounds. Consequently after drug removal rapid reversibility of the cleavage complexes is observed. Also, they suffer from rapid cellular efflux via membrane pumps and develop cellular resistance. As a result of the pharmacokinetic problems of the camptothecin and its clinically marketed drug there is a need in the development of 'non-camptothecin' TopI inhibitors as anticancer agents that inhibit Top I like the camptothecin (Cushman. M, *Journal of Medicinal Chemistry,* 1999, Vol. 42, No. 3, 446-457), (Cushman et al., U.S. Pat. No. 7,312,228B2, 2007).

OBJECTIVES OF THE INVENTION

The main objective of the present invention is to provide compounds with general formula I which show potent inhibitory activity on human Topoisomerase I and also show cytotoxicity in Breast Cancer cells and therefore may act as novel anticancer therapeutics.

Another objective of the present invention is to provide methods of preparation of compounds with general formula I.

Yet another objective of the present invention is to provide compounds with general formula I, which act as anticancer agents by inhibiting Topoisomerase I enzyme like camptothecin.

Yet another objective of the present invention is to provide compounds with general formula I, which are stable non-camptothecin candidates which possess the ability to increase the stability of the drug-DNA-Topoisomerase I ternary complex that eventually results in cancer cell death to achieve clinical anticancer activity.

Yet another objective of the present invention is to provide compounds with general formula I, or in acceptable salt which can be useful to treat variety of disease or disorders for which inhibition or modulation of topoisomerase I enzyme produces a physiologically beneficial response.

Yet another object of the present invention is to provide compounds of general formula I that are highly stable at pH 7.4 in plasma.

Yet another object of the present invention is to provide compounds of general formula I which show moderate solubility at pH 7.4.

SUMMARY OF THE INVENTION

The present invention relates to the compound represented by following formula I or a pharmaceutically acceptable salt thereof:

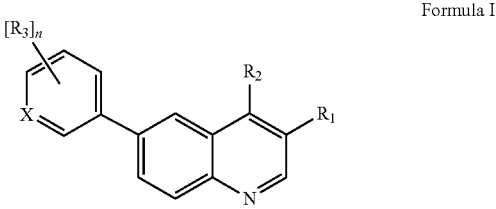

Formula I wherein
R₁ is an optionally aromatic heterocyclic group selected from the group consisting of oxadiazole, pyridyl, amino pyridyl, and furyl, wherein aromatic heterocyclic group may be optionally substituted with —CH₃ or —NH₂;
R₂ is water soluble or hydrophilic functional group —NR₅R₆,
R₅ and R₆ are either same or different selected from hydrogen atom, an optionally substituted C₁-C₆ aminoalkyl, an optionally substituted C₁-C₆ alkyl chain bearing aromatic heterocyclic group, or an optionally substituted C₁-C₆ alkyl chain bearing aliphatic heterocyclic group;
R₃ is selected from a hydrogen, a halogen, hydroxy, cyano, C₁-C₆ alkyl, C₁-C₆ haloalkyl, C₁-C₆ alkoxy, C₁-C₆ haloalkoxy, amino, alkylamino, acyl amino and carbamate;
X is nitrogen or carbon; and
n is 0-3.

In a preferred embodiment, the R1 is 1,3,4-oxadiazole.
In an embodiment the compound of Formula I is selected from the group consisting of:
6-(4-methoxyphenyl)-N-(2-morpholinoethyl)-3-(1,3,4-oxadiazol-2-yl)quinolin-4-amine (9) 6-(4-methoxyphenyl)-3-(5-methyl-1,3,4-oxadiazol-2-yl)-N-(2-morpholinoethyl)quinolin-4-amine (14)
N-(3-(1H-imidazol-1-yl)propyl)-6-(4-methoxyphenyl)-3-(1,3,4-oxadiazol-2-yl)quinolin-4-amine (18)
N-(3-(1H-imidazol-1-yl)propyl)-6-(3,4-dimethoxyphenyl)-3-(1,3,4-oxadiazol-2-yl)quinolin-4-amine (19)
N-(3-(1H-imidazol-1-yl)propyl)-6-(4-aminophenyl)-3-(1,3,4-oxadiazol-2-yl)quinolin-4-amine (20)
4-(4-((3-(1H-imidazol-1-yl)propyl)amino)-3-(1,3,4-oxadiazol-2-yl)quinolin-6-yl)benzonitrile (21)
4-(4-((3-(1H-imidazol-1-yl)propyl)amino)-3-(1,3,4-oxadiazol-2-yl)quinolin-6-yl)phenol (22)
N-(3-(1H-imidazol-1-yl)propyl)-6-(6-aminopyridin-3-yl)-3-(1,3,4-oxadiazol-2-yl)quinolin-4-amine (24)
N-(3-(1H-imidazol-1-yl)propyl)-6-(4-methoxy-3-methylphenyl)-3-(1,3,4-oxadiazol-2-yl)quinolin-4-amine (28)
N-(3-(1H-imidazol-1-yl)propyl)-3-(1,3,4-oxadiazol-2-yl)-6-(p-tolyl)quinolin-4-amine (29)
N-(3-(1H-imidazol-1-yl)propyl)-3-(1,3,4-oxadiazol-2-yl)-6-(pyridin-3-yl)quinolin-4-amine (30)
N-(3-(1H-imidazol-1-yl)propyl)-6-(4-methoxy-2-methylphenyl)-3-(1,3,4-oxadiazol-2-yl)quinolin-4-amine (31)
N-(3-(1H-imidazol-1-yl)propyl)-6-(4-methoxy-2,6-dimethylphenyl)-3-(1,3,4-oxadiazol-2-yl)quinolin-4-amine (32)
N-(3-(1H-imidazol-1-yl)propyl)-6-(6-methoxypyridin-3-yl)-3-(1,3,4-oxadiazol-2-yl)quinolin-4-amine (33)
N-(3-(1H-imidazol-1-yl)propyl)-6-(4-ethoxyphenyl)-3-(1,3,4-oxadiazol-2-yl)quinolin-4-amine (34)
N-(3-(1H-imidazol-1-yl)propyl)-6-(4-ethylphenyl)-3-(1,3,4-oxadiazol-2-yl)quinolin-4-amine (35)
N-(3-(1H-imidazol-1-yl)propyl)-6-(4-isopropoxyphenyl)-3-(1,3,4-oxadiazol-2-yl)quinolin-4-amine (36)
N-(3-(1H-imidazol-1-yl)propyl)-6-(4-isopropylphenyl)-3-(1,3,4-oxadiazol-2-yl)quinolin-4-amine (37)
N-(3-(1H-imidazol-1-yl)propyl)-6-(6-methylpyridin-3-yl)-3-(1,3,4-oxadiazol-2-yl)quinolin-4-amine (38)
5-(4-((3-(1H-imidazol-1-yl)propyl)amino)-3-(1,3,4-oxadiazol-2-yl)quinolin-6-yl)pyridin-2-ol (39)
6-(4-methoxyphenyl)-N-(3-morpholinopropyl)-3-(1,3,4-oxadiazol-2-yl)quinolin-4-amine (43)
6-(6-methoxypyridin-3-yl)-N-(3-morpholinopropyl)-3-(1,3,4-oxadiazol-2-yl)quinolin-4-amine (44)
N-(3-morpholinopropyl)-3-(1,3,4-oxadiazol-2-yl)-6-(p-tolyl)quinolin-4-amine (44a)
6-(6-aminopyridin-3-yl)-N-(3-morpholinopropyl)-3-(1,3,4-oxadiazol-2-yl)quinolin-4-amine (45)
6-(3,4-dimethoxyphenyl)-N-(3-morpholinopropyl)-3-(1,3,4-oxadiazol-2-yl)quinolin-4-amine (45a)
N-(2-(1H-imidazol-1-yl)ethyl)-6-(4-methoxyphenyl)-3-(1,3,4-oxadiazol-2-yl)quinolin-4-amine (50)
5-(4-((3-(1H-imidazol-1-yl)propyl)amino)-6-(4-methoxyphenyl)quinolin-3-yl)-1,3,4-oxadiazol-2-amine (52)
N-(3-(1H-imidazol-1-yl)propyl)-6-(4-methoxyphenyl)-3-(5-methyl-1,3,4-oxadiazol-2-yl)quinolin-4-amine (54)
N-(3-(1H-pyrrol-1-yl)propyl)-6-(4-methoxyphenyl)-3-(1,3,4-oxadiazol-2-yl)quinolin-4-amine (58)
6-(4-methoxyphenyl)-3-(1,3,4-oxadiazol-2-yl)-N-(3-(pyrrolidin-1-yl)propyl)quinolin-4-amine (62)
N-(3-(1H-imidazol-1-yl)propyl)-6-(6-aminopyridin-3-yl)-3-(furan-2-yl)quinolin-4-amine (69)
N-(3-(1H-imidazol-1-yl)propyl)-3-(furan-2-yl)-6-(4-methoxyphenyl)quinolin-4-amine (70)
N-(3-(1H-imidazol-1-yl)propyl)-3-(furan-2-yl)-6-(6-methoxypyridin-3-yl)quinolin-4-amine (71)
N-(3-(1H-imidazol-1-yl)propyl)-3-(6-aminopyridin-3-yl)-6-(4-methoxyphenyl)quinolin-4-amine (73)
N-(3-(1H-imidazol-1-yl)propyl)-3-(1,3,4-oxadiazol-2-yl)-6-(4-(trifluoromethyl)phenyl)quinolin-4-amine (79)
N-(3-(1H-imidazol-1-yl)propyl)-6-(4-(dimethylamino)phenyl)-3-(1,3,4-oxadiazol-2-yl)quinolin-4-amine (80)
N-(3-(1H-imidazol-1-yl)propyl)-3-(1,3,4-oxadiazol-2-yl)-6-(4-(trifluoromethoxy)phenyl)quinolin-4-amine (81)
N-(3-(1H-imidazol-1-yl)propyl)-6-(3-methoxyphenyl)-3-(1,3,4-oxadiazol-2-yl)quinolin-4-amine (82)
N-(3-(1H-imidazol-1-yl)propyl)-6-(2-methoxyphenyl)-3-(1,3,4-oxadiazol-2-yl)quinolin-4-amine (83) tert-butyl (4-(4-((3-(1H-imidazol-1-yl)propyl)amino)-3-(1,3,4-oxadiazol-2-yl)quinolin-6-yl)phenyl)(methyl)carbamate (84)
N-(3-(1H-imidazol-1-yl)propyl)-6-(4-(methylamino)phenyl)-3-(1,3,4-oxadiazol-2-yl)quinolin-4-amine (85)
N-(4-(4-((3-(1H-imidazol-1-yl)propyl)amino)-3-(1,3,4-oxadiazol-2-yl)quinolin-6-yl)phenyl)acetamide (86)

In another embodiment a process of preparation of compounds of formula I comprising, reacting a compound of formula II

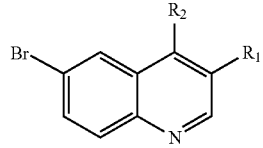

Formula II with boronic acids of formula V or formula VI

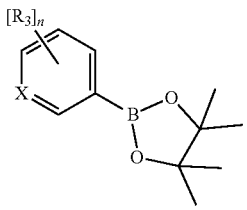

Formula V or

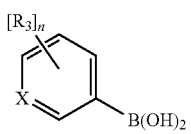

Formula VI in presence of 2(M) sodium carbonate solution and tetrakis(triphenylphosphine)palladium(O) catalyst in a suitable solvent to obtain the compound of Formula I,

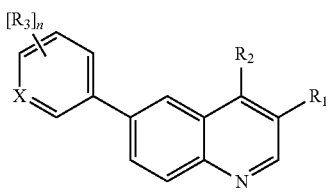

Formula I wherein
- $R_1$ is an optionally aromatic heterocyclic group selected from the group consisting of oxadiazole, pyridyl, amino pyridyl, and furyl, wherein aromatic heterocyclic group may be optionally substituted with —$CH_3$ or —$NH_2$;
- $R_2$ is water soluble or hydrophilic functional group —$NR_5R_6$,
- $R_5$ and $R_6$ are either same or different selected from hydrogen atom, an optionally substituted $C_1$-$C_6$ aminoalkyl, an optionally substituted $C_1$-$C_6$ alkyl chain bearing aromatic heterocyclic group, or an optionally substituted $C_1$-$C_6$ alkyl chain bearing aliphatic heterocyclic group;
- $R_3$ is selected from a hydrogen, a halogen, hydroxy, cyano, $C_1$-$C_6$ alkyl, $C_1$-$C_6$ haloalkyl, $C_1$-$C_6$ alkoxy, $C_1$-$C_6$ haloalkoxy, amino, alkylamino, acyl amino and carbamate;
- X is nitrogen or carbon; and
- n is 0-3.

In an embodiment the suitable solvent is ethanol.

In another embodiment of the invention wherein compounds are prepared by the process wherein the process steps comprising:
(i) reacting 4-bromoaniline (compound 1) with diethyl ethoxymethylenemalonate at 120° C. for 2 hours to obtain compound 2. Again heating of 4-bromoaniline with with meldrum's acid and triethylorthoformate in polar solvent such as ethanol at 85° C. for 2 hours produces compound 63.
(ii) heating of compound 2 and 63 in dowtherm [eutectic mixture of 26.5% diphenyl+73.5% diphenyl oxide] solvent at 180° C. to 240° C. for 2 hours to obtain compound 3 and 64.
(iii) reacting compound 64 with iodinating reagent such as $I_2$, 20% KI in 2(N) NaOH at room temperature for 3 hours to obtain compound 65.
(iv) reacting compound 3 and 65 with chlorinating agent such as $POCl_3$ at 100° C. for 2 to 7 hours to produce compound 4 and 66.
(v) reacting compound 4 with a variety of amines such as 4-(2-aminoethyl)morpholine, 3-(1H-imidazol-1-yl)propan-1-amine, 3-morpholinopropan-1-amine, 2-(1H-imidazol-1-yl)ethanamine, 3-(1H-pyrrol-1-yl)propan-1-amine, 3-(pyrrolidin-1-yl)propan-1-amine and methylamine with mild base such as DIPEA in 1,4-dioxane at room temperature to 60° C. for 12-48 hours to obtain compound 5, 15, 40, 46, 55, 59 and 74 respectively. Similarly compound 66 was heated with 3-(1H-imidazol-1-yl)propan-1-amine, DIPEA [N,N-diisopropylethylamine] as base in the same solvent at 70° C. for 12 hours to produce compound 67.
(vi) reacting compound 5, 15, 40, 46, 55, 59 and 74 as obtained in step (v) with hydrazine monohydrate in polar solvent such as ethanol at room temperature for 8 to 12 hours to afford compound 6, 16, 41, 47, 56, 60 and 75 respectively.
(vii) reacting compound 6, 16, 41, 47, 56, 60 and 75 with triethylorthoformate at 100° C. for 4 to 12 hours to obtain compound 7, 17, 42, 48, 57, 61 and 76 respectively.
(viii) reacting compound 6 and 16 with triethyl orthoacetate in polar solvent such as ethanol at 100 to 110° C. for 6 to 8 hours to afford 12 and 53 respectively.
(ix) reacting compound 16 with cyanogen bromide in polar solvent such as methanol at refluxing temperature for 4 hours to obtain compound 51.
(x) heating compound 67 with furan-2-boronic acid and 5-(4,4,5,5-tetramethyl-1,3,2-dioxaborolan-2-yl)pyridin-2-amine separately along with base such as 2(M) $Na_2CO_3$ solution and tetrakis(triphenylphosphine)palladium(0) catalyst in 1,4-dioxane solvent at 80 to 100° C. for 12 hours to afford compound 68 and 72 respectively.
(xi) reacting compound 7, 12, 15, 17, 42, 48, 51, 53, 57, 61, 68, 72, 76 and 82 with various boronic acids, base such as 2(M) $Na_2CO_3$ solution and tetrakis(triphenylphosphine)palladium(0) and bis(triphenylphosphine)palladium(II) dichloride catalyst in 1,4-dioxane and dimethylformamide (DMF) solvent at 100° C. for 6-24 hours to afford compound 8-11, 13-14, 18-39, 43-45a, 49-50, 52, 54, 58, 62, 69-71, 73, 77, 78-84 and 86.
(xii) finally compound 84 was subjected to deprotection in 4M HCl-dioxane to provide compound 85.

In another embodiment of the invention wherein compounds with formula I show potent inhibitory activity on human topoisomerase I and also show cytotoxicity in Breast Cancer cells and therefore may act as novel anticancer therapeutics.

In another embodiment of the invention wherein compounds with formula I can be useful to treat any of a variety of conditions where inhibition of topoisomerase I enzyme is important.

In another embodiment of the invention the compounds with formula I are stable non-camptothecin candidates which possess the ability to increase the stability of the drug-DNA-Topoisomerase I ternary complex that eventually results in cancer cell death. Thus, these compounds may act as topoisomerase I poisons.

In another embodiment of the invention wherein compounds with formula I shows they have good stability at pH 7.4 in plasma.

In one embodiment according to this aspect of the invention, $R_1$, $R_2$ and $R_3$ substituted aromatic ring are together essential for these compounds to show potential human TopI (HTopI) inhibitory activity.

In another embodiment according to this aspect of the invention, a general screening method is provided to screen compounds of general formula I against Human TopI (HTopI) and *Leishmania donovani* Top I (LdTopI) in plasmid DNA relaxation experiments.

In another embodiment according to this aspect of the invention, in vitro viable dose dependent screening method is provided to screen compounds of general formula I for their effect on inhibition of recombinant HTopI and LdTopI in the plasmid DNA relaxation assay.

The results were compared with standard camptothecin (CPT) induced inhibition of HTopI in the plasmid DNA relaxation assay.

In another embodiment according to this aspect of the invention, an ex vivo relaxation assay is provided to screen compounds of general formula I for inhibitory impact on human breast adenocarcinoma (MCF7) cell extracts as the source of TopI. The assay has the benefit of using native human TopI.

In another embodiment according to this aspect of the invention, an assay was provided to compounds of general formula I for their ability to stabilize TopI-cleavage complexes (TopIcc). The results were compared with camptothecin (CPT), which showed that the compounds are able to stabilize the Top I-cleavable complexes.

In another embodiment according to this aspect of the invention, the said compounds with general formula (I) show anticancer activity in cytotoxic assays in human breast adenocarcinoma cell lines (MCF7), human cervical cancer cell lines (HeLa), human colon carcinoma cell lines (HCT116), as well as noncancerous human embryonic kidney (HEK293) cells.

In another embodiment according to this aspect of the invention, the said compounds with general formula (I) show high plasma stability at pH 7.4.

In another embodiment according to this aspect of the invention, the said compounds with general formula (I) show moderate aqueous solubility at pH 7.4.

DESCRIPTION OF THE INVENTION

Figure 1:
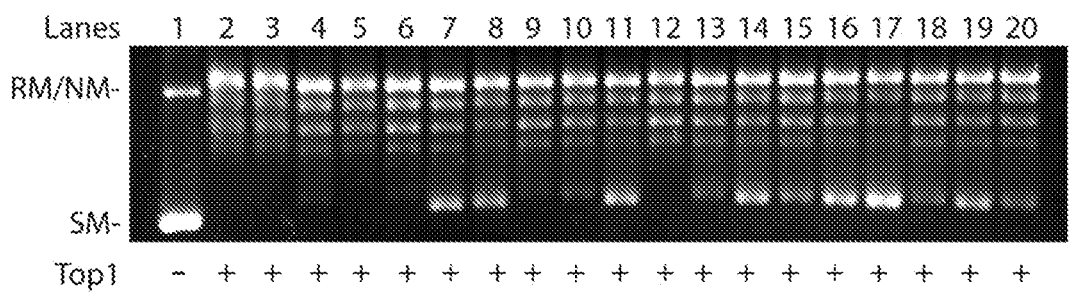
FIG. 1: depicts in vitro inhibitory activity of the bicyclic compounds of Formula I: (A) test compounds 26, 18, 20, 50, 24, 30 on human TopI mediated plasmid DNA relaxation activity. Lane 1: 90 fmol of pBSSK($^+$) DNA; lanes 2: same as lane 1 but simultaneously incubated with 30 fmol of HTop I; lane 3-20, same as lane 2 but in the presence of 0.2, 0.3 and 0.5 µM compound 26 (lane 3-5), compound 18 (lane 6-8), compound 20 (lane 9-11), compound 50 (lane 12-14), compound 24 (lane 15-17), compound 30 (lane 18-20). Positions of supercoiled monomer (SM), relaxed and nicked monomer (RL/NM) are indicated. (B) test compounds 68, 15, 17, 33, 24, 18 on Human Top I mediated plasmid DNA relaxation activity. Lane 1: 90 fmol of pBSSK($^+$) DNA; lanes 2: same as lane 1 but simultaneously incubated with 30 fmol of HTopI; lane 3-20 same as lane 2 but in the presence of 0.2, 0.3 and 0.5 µM compound 68 (lane 3-5), compound 15 (lane 6-8), compound 17 (lane 9-11), compound 33 (lane 12-14), compound 24 (lane 15-17), compound 29 (lane 18-20). Positions of supercoiled monomer (SM), relaxed and nicked monomer (RL/NM) are indicated. (C) test compounds 45, 31, 28, 33, 24, 18 on Human Top I mediated plasmid DNA relaxation activity. Lane 1: 90 fmol of pBSSK ($^+$) DNA; lanes 2: same as lane 1 but simultaneously incubated with 30 fmol of HTopI; lane 3-20, same as lane 2 but in the presence of 0.2, 0.3 and 0.5 µM compound 45 (lane 3-5), compound 31 (lane 6-8), compound 28 (lane 9-11), compound 73 (lane 12-14), compound 33 (lane 15-17), compound 30 (lane 18-20). Positions of supercoiled monomer (SM), relaxed and nicked monomer (RL/NM) are indicated.
Figure 1:
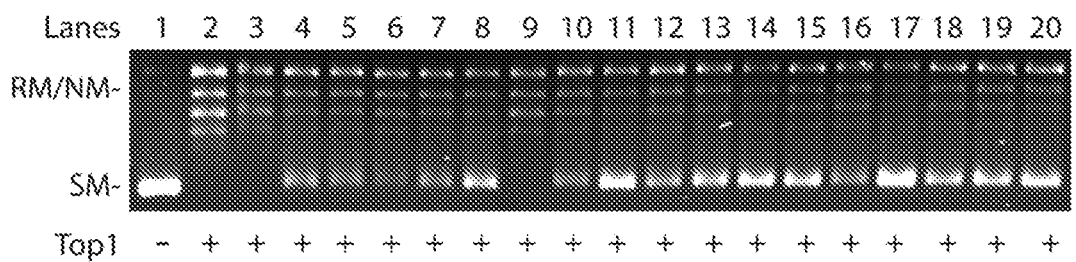
Figure 1:
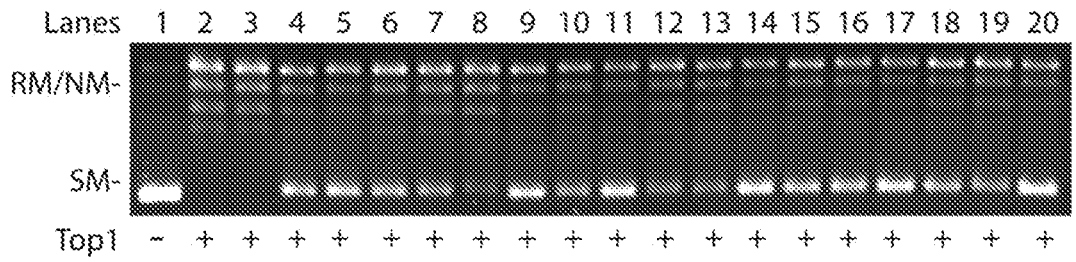

The present invention relates to the compound of formula I or a salt thereof:

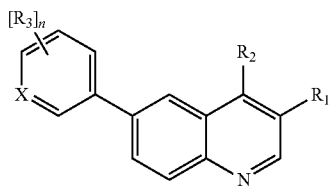

Formula I wherein
- $R_1$ is an optionally aromatic heterocyclic group selected from the group consisting of oxadiazole, pyridyl, amino pyridyl, and furyl, wherein aromatic heterocyclic group may be optionally substituted with —$CH_3$ or —$NH_2$;
- $R_2$ is water soluble or hydrophilic functional group —$NR_5R_6$,
- $R_5$ and $R_6$ are either same or different selected from hydrogen atom, an optionally substituted $C_1$-$C_6$ aminoalkyl, an optionally substituted $C_1$-$C_6$ alkyl chain bearing aromatic heterocyclic group, or an optionally substituted $C_1$-$C_6$ alkyl chain bearing aliphatic heterocyclic group;
- $R_3$ is selected from a hydrogen, a halogen, hydroxy, cyano, $C_1$-$C_6$ alkyl, $C_1$-$C_6$ haloalkyl, $C_1$-$C_6$ alkoxy, $C_1$-$C_6$ haloalkoxy, amino, alkylamino, acyl amino and carbamate;
- X is nitrogen or carbon; and
- n is 0-3.

In a preferred embodiment, the $R_1$ is 1,3,4-oxadiazole.

The compound of present invention has the structure of formula I as depicted in the table below:

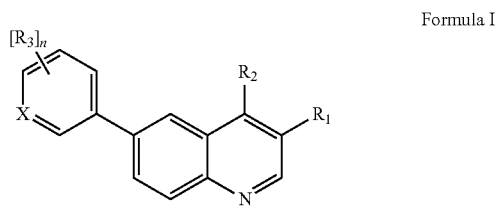

Formula I

TABLE 1

| Compound | $R_1$ | $R_2$ | [R₃]ₙ / X-aryl group | n |
|---|---|---|---|---|
| 9 | 1,3,4-oxadiazol-2-yl (methyl) | —NH—CH₂CH₂—N(morpholine) | MeO-phenyl | 1 |
| 14 | 2,5-dimethyl-1,3,4-oxadiazole | —NH—CH₂CH₂—N(morpholine) | MeO-phenyl | 1 |
| 18 | methyl-1,3,4-oxadiazol-2-yl | —NH—CH₂CH₂CH₂—N(imidazole) | MeO-phenyl | 1 |
| 19 | methyl-1,3,4-oxadiazol-2-yl | —NH—CH₂CH₂CH₂—N(imidazole) | (MeO)₂-phenyl | 2 |
| 20 | methyl-1,3,4-oxadiazol-2-yl | —NH—CH₂CH₂CH₂—N(imidazole) | H₂N-phenyl | 1 |
| 21 | methyl-1,3,4-oxadiazol-2-yl | —NH—CH₂CH₂CH₂—N(imidazole) | NC-phenyl | 1 |
| 22 | methyl-1,3,4-oxadiazol-2-yl | —NH—CH₂CH₂CH₂—N(imidazole) | HO-phenyl | 1 |

TABLE 1-continued
| Compound | R₁ | R₂ | ![R₃]ₙ group | n |
|---|---|---|---|---|
| 24 | 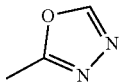 | 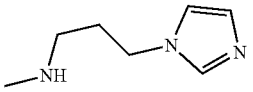 | 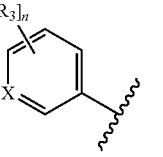 | 1 |
| 26 | 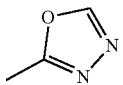 | 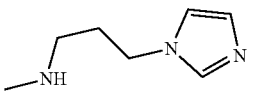 | 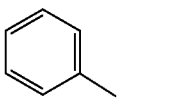 | 0 |
| 28 | 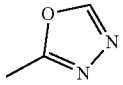 | 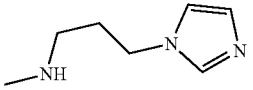 | 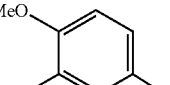 | 2 |
| 29 | 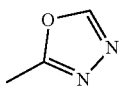 | 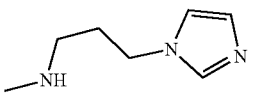 | 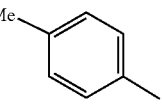 | 1 |
| 30 | 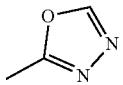 | 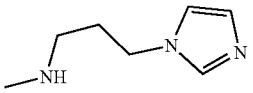 | 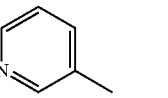 | 0 |
| 31 | 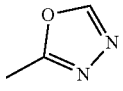 | 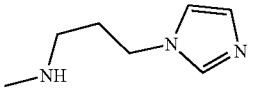 | 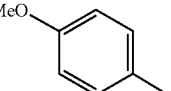 | 2 |
| 32 | 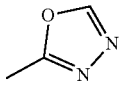 | 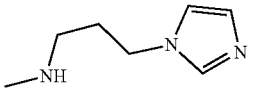 | 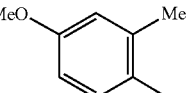 | 3 |
| 33 | 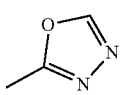 | 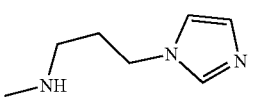 | 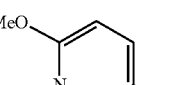 | 1 |
| 34 | 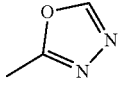 | 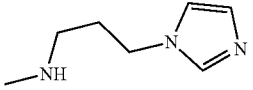 | 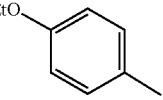 | 1 |
| 35 | 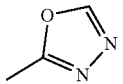 | 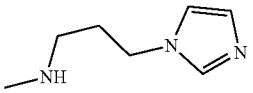 | 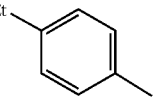 | 1 |
| 36 | 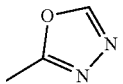 | 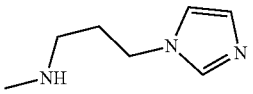 | 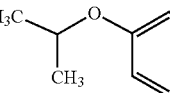 | 1 |

TABLE 1-continued

| Compound | R₁ | R₂ | [R₃]ₙ aryl/heteroaryl group | n |
|---|---|---|---|---|
| 37 | 5-methyl-1,3,4-oxadiazol-2-yl | —NH-CH₂CH₂CH₂-(imidazol-1-yl) | 4-(1-methylethyl)phenyl (Me-CH(Me)-C₆H₄-) | 1 |
| 38 | 5-methyl-1,3,4-oxadiazol-2-yl | —NH-CH₂CH₂CH₂-(imidazol-1-yl) | 2-methylpyridin-5-yl | 1 |
| 39 | 5-methyl-1,3,4-oxadiazol-2-yl | —NH-CH₂CH₂CH₂-(imidazol-1-yl) | 2-hydroxypyridin-5-yl | 1 |
| 43 | 5-methyl-1,3,4-oxadiazol-2-yl | —NH-CH₂CH₂CH₂-(morpholin-4-yl) | 4-methoxyphenyl | 1 |
| 44 | 5-methyl-1,3,4-oxadiazol-2-yl | —NH-CH₂CH₂CH₂-(morpholin-4-yl) | 2-methoxypyridin-5-yl | 1 |
| 44a | 5-methyl-1,3,4-oxadiazol-2-yl | —NH-CH₂CH₂CH₂-(morpholin-4-yl) | 4-methylphenyl | 1 |
| 45 | 5-methyl-1,3,4-oxadiazol-2-yl | —NH-CH₂CH₂CH₂-(morpholin-4-yl) | 2-aminopyridin-5-yl | 1 |
| 45a | 5-methyl-1,3,4-oxadiazol-2-yl | —NH-CH₂CH₂CH₂-(morpholin-4-yl) | 3,4-dimethoxyphenyl | 2 |
| 50 | 5-methyl-1,3,4-oxadiazol-2-yl | —NH-CH₂CH₂-(imidazol-1-yl) | 4-methoxyphenyl | 1 |
| 52 | 5-amino-1,3,4-oxadiazol-2-yl (2-methyl) | —NH-CH₂CH₂CH₂-(imidazol-1-yl) | 4-methoxyphenyl | 1 |
| 54 | 2,5-dimethyl-1,3,4-oxadiazol-? | —NH-CH₂CH₂CH₂-(imidazol-1-yl) | 4-methoxyphenyl | 1 |

TABLE 1-continued

| Compound | R₁ | R₂ | [R₃]ₙ group | n |
|---|---|---|---|---|
| 58 | 5-methyl-1,3,4-oxadiazol-2-yl | —NH—(CH₂)₃—imidazol-1-yl | 4-MeO-phenyl | 1 |
| 62 | 5-methyl-1,3,4-oxadiazol-2-yl | —NH—(CH₂)₃—pyrrolidin-1-yl | 4-MeO-phenyl | 1 |
| 69 | 5-methyl-isoxazol-3-yl | —NH—(CH₂)₃—imidazol-1-yl | 2-amino-pyridin-5-yl | 1 |
| 70 | 5-methyl-furan-2-yl | —NH—(CH₂)₃—imidazol-1-yl | 4-MeO-phenyl | 1 |
| 71 | 5-methyl-furan-2-yl | —NH—(CH₂)₃—imidazol-1-yl | 2-MeO-pyridin-5-yl | 1 |
| 73 | 2-amino-pyridin-5-yl | —NH—(CH₂)₃—imidazol-1-yl | 4-MeO-phenyl | 1 |
| 79 | 5-methyl-1,3,4-oxadiazol-2-yl | —NH—(CH₂)₃—imidazol-1-yl | 4-CF₃-phenyl | 1 |
| 80 | 5-methyl-1,3,4-oxadiazol-2-yl | —NH—(CH₂)₃—imidazol-1-yl | 4-NMe₂-phenyl | 1 |
| 81 | 5-methyl-1,3,4-oxadiazol-2-yl | —NH—(CH₂)₃—imidazol-1-yl | 4-OCF₃-phenyl | 1 |
| 82 | 5-methyl-1,3,4-oxadiazol-2-yl | —NH—(CH₂)₃—imidazol-1-yl | 3-MeO-phenyl | 1 |
| 83 | 5-methyl-1,3,4-oxadiazol-2-yl | —NH—(CH₂)₃—imidazol-1-yl | 2-OMe-phenyl | 1 |
| 84 | 5-methyl-1,3,4-oxadiazol-2-yl | —NH—(CH₂)₃—imidazol-1-yl | 4-(N-Me-N-Boc-amino)-phenyl | 1 |

TABLE 1-continued

| Compound | R₁ | R₂ | 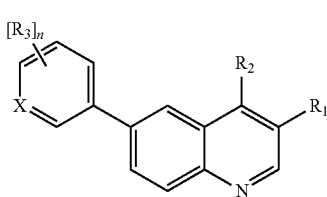 | n |
|---|---|---|---|---|
| 85 | 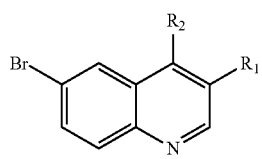 | —NH<br>(propyl-imidazole) | HN—(p-tolyl, methyl) | 1 |
| 86 | 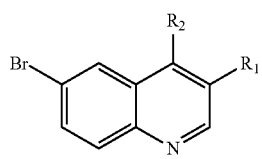 | —NH<br>(propyl-imidazole) | 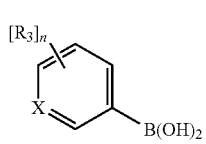 (acetamide p-tolyl) | 1 |

General Process of Preparation

A process of preparation of compounds of formula I comprising
reacting a compound of formula II Formula II with a boronic acid of formula V or formula VI Formula V or Formula VI in presence of 2(M) Na₂CO₃ solution and tetrakis(triphenylphosphine)palladium(0) catalyst in a solvent to obtain the compound of Formula I, Formula I wherein R₁—R₃, n and X are as defined above.

As described herein the compound of formula II is selected from the group consisting of 6-bromo-N-(2-morpholinoethyl)-3-(1,3,4-oxadiazol-2-yl)quinolin-4-amine (compound 7);

6-bromo-3-(5-methyl-1,3,4-oxadiazol-2-yl)-N-(2-morpholinoethyl)quinolin-4-amine (compound 12);

N-(3-(1H-imidazol-1-yl)propyl)-6-bromo-3-(1,3,4-oxadiazol-2-yl)quinolin-4-amine (compound 17);

6-bromo-N-(3-morpholinopropyl)-3-(1,3,4-oxadiazol-2-yl)quinolin-4-amine (compound 42);

N-(2-(1H-imidazol-1-yl)ethyl)-6-bromo-3-(1,3,4-oxadiazol-2-yl)quinolin-4-amine (compound 48);

5-(4-(3-(1H-imidazol-1-yl)propylamino)-6-bromoquinolin-3-yl)-1,3,4-oxadiazol-2-amine (compound 51);

N-(3-(1H-imidazol-1-yl)propyl)-6-bromo-3-(5-methyl-1,3,4-oxadiazol-2-yl)quinolin-4-amine (compound 53);

N-(3-(1H-pyrrol-1-yl)propyl)-6-bromo-3-(1,3,4-oxadiazol-2-yl)quinolin-4-amine (compound 57);

6-bromo-3-(1,3,4-oxadiazol-2-yl)-N-(3-(pyrrolidin-1-yl)propyl)quinolin-4-amine (compound 61);

N-(3-(1H-imidazol-1-yl)propyl)-6-bromo-3-(furan-2-yl)quinolin-4-amine (compound 68);

N-(3-(1H-imidazol-1-yl)propyl)-3-(6-aminopyridin-3-yl)-6-bromoquinolin-4-amine (compound 72); and 6-bromo-N-methyl-3-(1,3,4-oxadiazol-2-yl)quinolin-4-amine(compound 76).

In the preferred aspect the process of preparation of compound of Formula I, wherein R₁ of Formula I is

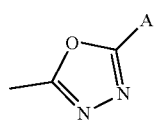

the process comprising the following steps,
 (i) reacting a 4-bromoaniline (compound 1) with a diethyl ethoxymethylenemalonate at 120° C. for 2 hours to obtain diethyl 2-((4-bromophenylamino)methylene) malonate (compound 2);
 (ii) heating of the compound 2 in a dowtherm [eutectic mixture of 26.5% diphenyl+73.5% diphenyl oxide] solvent at 240° C. for 2.5 hours to obtain ethyl 6-bromo-4-hydroxyquinoline-3-carboxylate (compound 3);
 (iii) reacting the compound 3 with a chlorinating agent POCl$_3$ at 100° C. for 2 hours to produce an ethyl 6-bromo-4-chloroquinoline-3-carboxylate (compound 4);
 (iv) reacting the compound 4 with an amine selected from the group consisting of -(2-aminoethyl)morpholine, 3-(1H-imidazol-1-yl)propan-1-amine, 3-morpholino-propan-1-amine, 2-(1H-imidazol-1-yl)ethanamine, 3-(1H-pyrrol-1-yl)propan-1-amine, 3-(pyrrolidin-1-yl)propan-1-amine and methylamine in presence of DIPEA to obtain a compound of Formula III;

Formula III

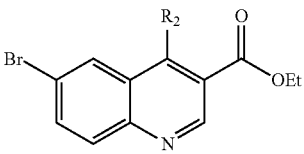

(v) reacting the compound of Formula III as obtained in previous step with a hydrazine monohydrate in a polar solvent such as ethanol at room temperature to obtain a compound of Formula IV;

Formula IV

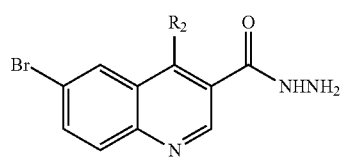

(vi) heating the compound of Formula IV with a triethylorthoformate or a triethyl orthoacetate to obtain a compound of formula IIA;

Formula IIA

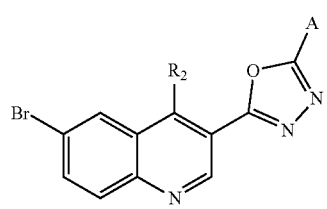

wherein A is H or methyl group (vii) reacting compound of the formula IIA with a boronic acid of formula V or formula VI Formula V

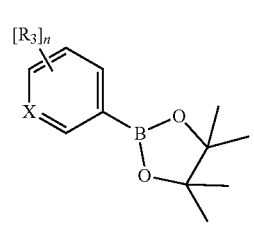

or

Formula VI

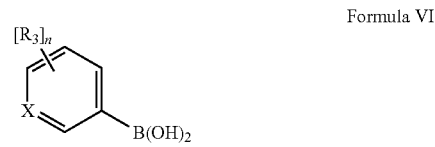

in presence of a 2(M) sodium carbonate solution and tetrakis(triphenylphosphine)palladium(0) catalyst in a suitable solvent to obtain the compound of formula IA, Formula IA

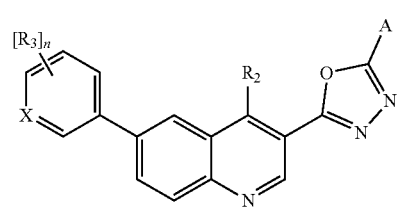

wherein R$_2$, R$_3$, X and n are as defined above.

In the another aspect the process of preparation of compound of Formula I, wherein R$_1$ of Formula I is

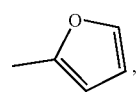

the process comprising the following steps,
 (i) reacting the 4-bromoaniline (compound 1) with 2,2-dimethyl-1,3-dioxane-4,6-dione and Triethyl orthoformate to obtain 5-((4-bromophenylamino)methylene)-2,2-dimethyl-1,3-dioxane-4,6-dione (compound 63);
 (ii) heating of compound 63 in dowtherm [eutectic mixture of 26.5% diphenyl+73.5% diphenyl oxide] solvent at 180° C. for 2 hours to obtain 6-bromoquinolin-4-ol (compound 64);
 (iii) reacting compound 64 with iodinating reagent such as I$_2$, 20% KI in 2(N) NaOH at room temperature for 3 hours to obtain 6-bromo-3-iodoquinolin-4-ol (compound 65); (iv) reacting compound 65 with chlorinating agent POCl$_3$ at 100° C. for 7 hours to produce 6-bromo-4-chloro-3-iodoquinoline (compound 66);
 (v) heating compound 66 with 3-(1H-imidazol-1-yl)propan-1-amine, DIPEA as base in ethanol at 70° C. for 12 hours to produce N-(3-(1H-imidazol-1-yl)propyl)-6-bromo-3-iodoquinolin-4-amine (compound 67);

(vi) heating compound 67 with furan-2-boronic acid along with 2(M) sodium carbonate solution and tetrakis(triphenylphosphine)palladium(0) catalyst in 1,4-dioxane and DMF solvent at 100° C. for 12 hours to afford N-(3-(1H-imidazol-1-yl)propyl)-6-bromo-3-(furan-2-yl)quinolin-4-amine (compound 68)

(vii) reacting compound 68 with 2-(4-methoxyphenyl)-4,4,5,5-tetramethyl-1,3,2-dioxaborolane, 2(M) Na$_2$CO$_3$ solution and tetrakis(triphenylphosphine)palladium(0) catalyst in 1,4-dioxane and DMF solvent at 100° C. for 28 hours to obtain compound 69

In yet another aspect, the process of preparation of compound of Formula I, wherein R$_1$ of Formula I is

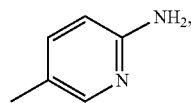

the process comprising the following steps, (i) treating the compound 67 with a 5-(4,4,5,5-tetramethyl-1,3,2-dioxaborolan-2-yl)pyridin-2-amine along with a 2(M) sodium carbonate solution and a tetrakis(triphenylphosphine)palladium(0) catalyst in 1,4-dioxane and DMF solvent at 80° C. for 12 hours to obtain a N-(3-(1H-imidazol-1-yl)propyl)-3-(6-aminopyridin-3-yl)-6-bromoquinolin-4-amine (compound 72);

(ii) heating the compound 72 with a 2-(4-methoxyphenyl)-4,4,5,5-tetramethyl-1,3,2-dioxaborolane, 2(M) sodium carbonate solution and the tetrakis(triphenylphosphine)palladium(0) catalyst in 1,4-dioxane and DMF solvent at 100° C. for 28 hours to afford compound 73.

The process of preparation of compound of formula I as given in table 1, wherein the process steps comprising:

(i) reacting 4-bromoaniline (compound 1) with diethyl ethoxymethylenemalonate at 120° C. for 2 hours to obtain compound 2. Again heating of 4-bromoaniline with with meldrum's acid and triethylorthoformate in polar solvent such as ethanol at 85° C. for 2 hours to obtain compound 63;

(ii) heating of compound 2 and 63 in dowtherm [eutectic mixture of 26.5% diphenyl+73.5% diphenyl oxide] solvent at 180° C. to 240° C. for 2 hours to obtain compound 3 and 64 respectively;

(iii) reacting compound 64 with iodinating reagent such as I$_2$, 20% KI in 2(N) NaOH at room temperature for 3 hours to obtain compound 65;

(iv) reacting compound 3 and 65 with chlorinating agent such as POCl$_3$ at 100° C. for 2 to 7 hours to obtain compound 4 and 66;

(v) reacting compound 4 with amines selected from 4-(2-aminoethyl)morpholine, 3-(1H-imidazol-1-yl)propan-1-amine, 3-morpholinopropan-1-amine, 2-(1H-imidazol-1-yl)ethanamine, 3-(1H-pyrrol-1-yl)propan-1-amine, 3-(pyrrolidin-1-yl)propan-1-amine and methylamine with mild base such as DIPEA in 1,4-dioxane at room temperature to 60° C. for 12-48 hours to obtain compound 5, 15, 40, 46, 55, 59 and 74 respectively. Similarly compound 66 was heated with 3-(1H-imidazol-1-yl)propan-1-amine, DIPEA [N,N-Diisopropylethylamine] as base in the same solvent at 70° C. for 12 hours to obtain compound 67;

(vi) reacting compound 5, 15, 40, 46, 55, 59 and 74 as obtained in step (v) with hydrazine monohydrate in polar solvent such as ethanol at room temperature for 8 to 12 hours to afford compound 6, 16, 41, 47, 56, 60 and 75 respectively;

(vii) reacting compound 6, 16, 41, 47, 56, 60 and 75 with triethylorthoformate at 100° C. for 4 to 12 hours to obtain compound 7, 17, 42, 48, 57, 61 and 76 respectively.

(viii) reacting compound 6 and 16 with triethyl orthoacetate in polar solvent such as ethanol at 100 to 110° C. for 6 to 8 hours to afford 12 and 53 respectively.

(ix) reacting compound 16 with cyanogen bromide in polar solvent such as methanol at refluxing temperature for 4 hours to obtain compound 51.

(x) heating compound 67 with furan-2-boronic acid and 5-(4,4,5,5-tetramethyl-1,3,2-dioxaborolan-2-yl)pyridin-2-amine separately along with base such as 2(M) Na$_2$CO$_3$ solution and tetrakis(triphenylphosphine)palladium(0) catalyst in 1,4-dioxane solvent at 80 to 100° C. for 12 hours to afford compound 68 and 72 respectively.

(xi) reacting compound 7, 12, 15, 17, 42, 48, 51, 53, 57, 61, 68, 72, 76, 82 with various boronic acids, base such as 2(M) Na$_2$CO$_3$ solution and tetrakis(triphenylphosphine)palladium(0) and bis(triphenylphosphine)palladium(II) dichloride catalyst in 1,4-dioxane and dimethylformamide (DMF) solvent at 100° C. for 6-24 hours to afford compound 8-11, 13-14, 18-39, 43-45a, 49-50, 52, 54, 58, 62, 69-71, 73, 77, 78-84 and 86.

(xii) finally compound 84 was subjected to deprotection in 4M HCl-dioxane to provide compound 85.

Experimental Details

The following examples are intended for illustrative purposes only and are not to be construed as being limitations for the invention thereon in any manner. Temperatures are given in degree Celsius. The structures of final products, intermediates and starting materials are confirmed by standard analytical methods, spectroscopic characterization e.g., MS, NMR.

Abbreviations used are those conventional in the art.

All starting materials, reagents, catalysts, building blocks, acids, bases, dehydrating agents and solvents utilized to synthesize the compounds of the present invention are either commercially available or can be produced by known organic synthesis methods in the art.

Abbreviations

DMF N,N-dimethylformamide

POCl$_3$ phosphorous oxychloride

DIPEA N,N-Diisopropylethylamine

Pd(PPh$_3$)$_4$ Tetrakis(triphenylphosphine)palladium(0)

EtOH Ethanol

THF Tetrahydrofuran

Ar Argon

CPT Camptothecin

HBBS Hank's Balanced Salt Solution

TEER transepithelial/transendothelial electrical resistance

UV Ultra voilet

Scheme 1
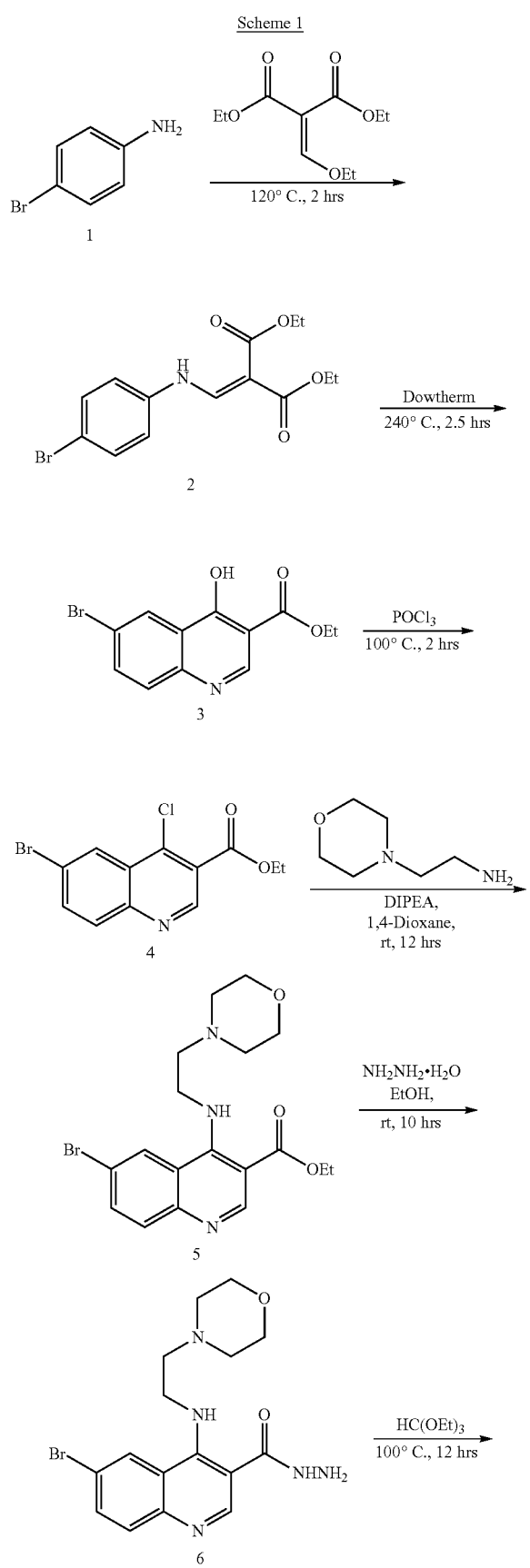
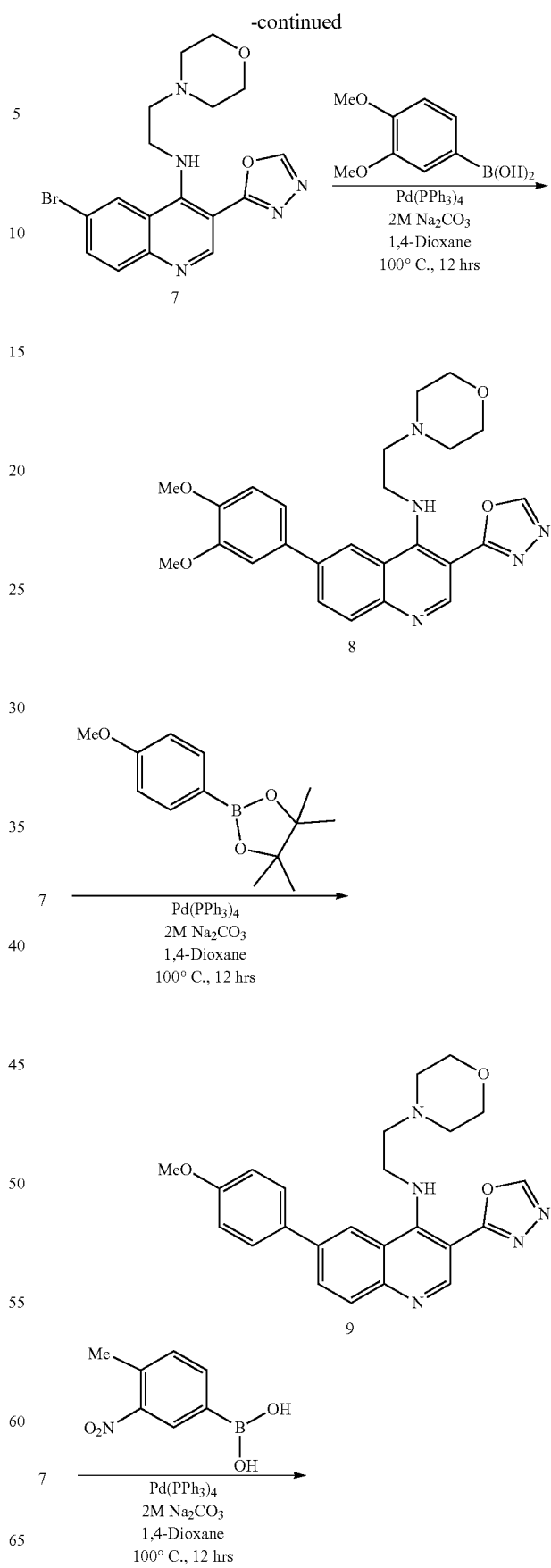

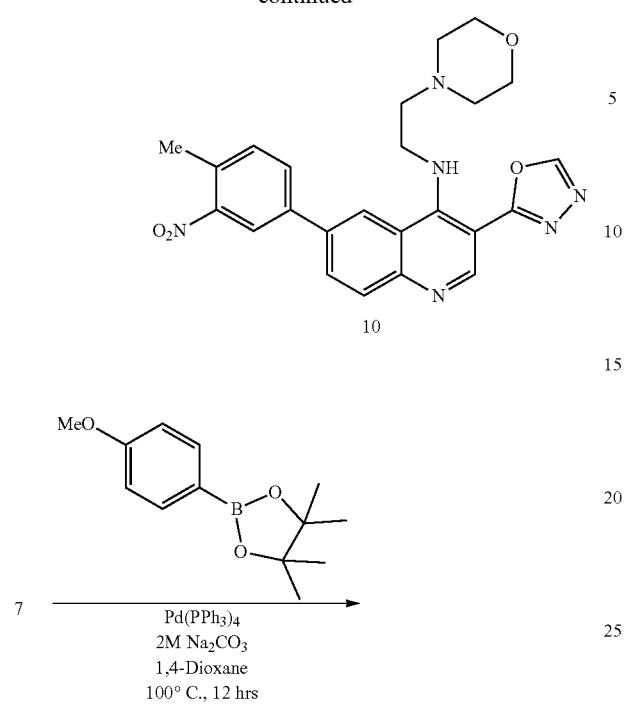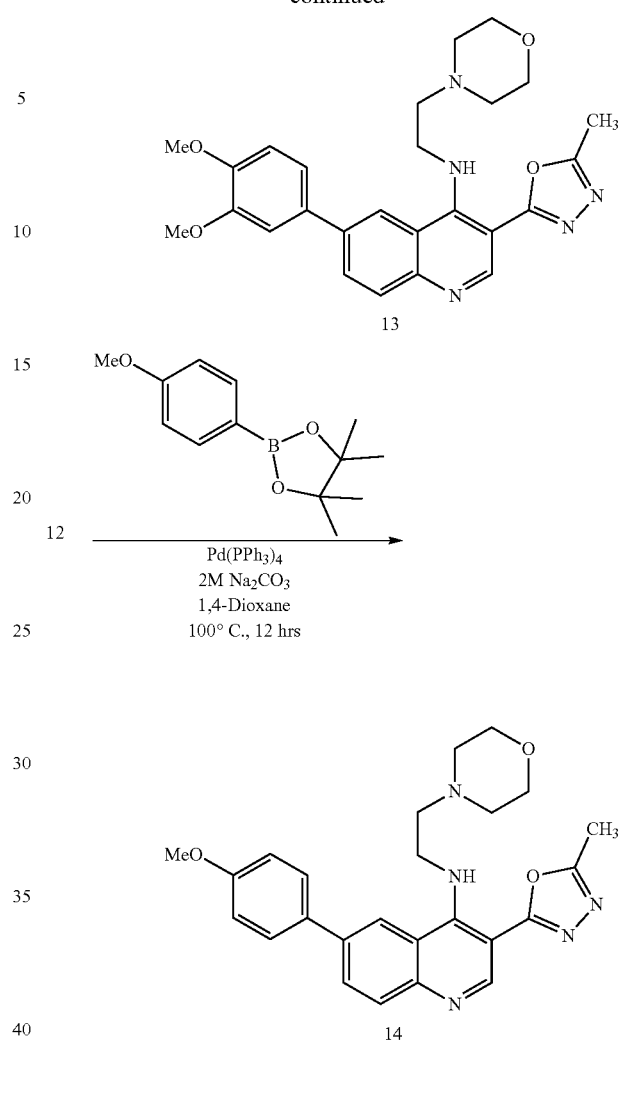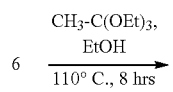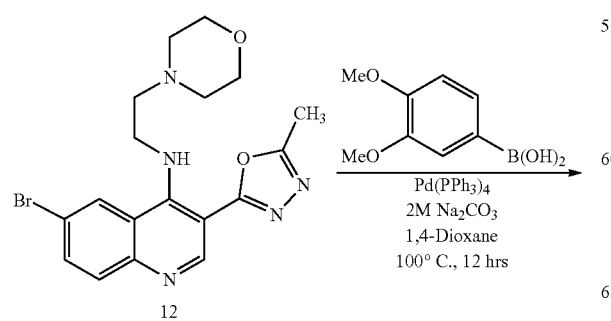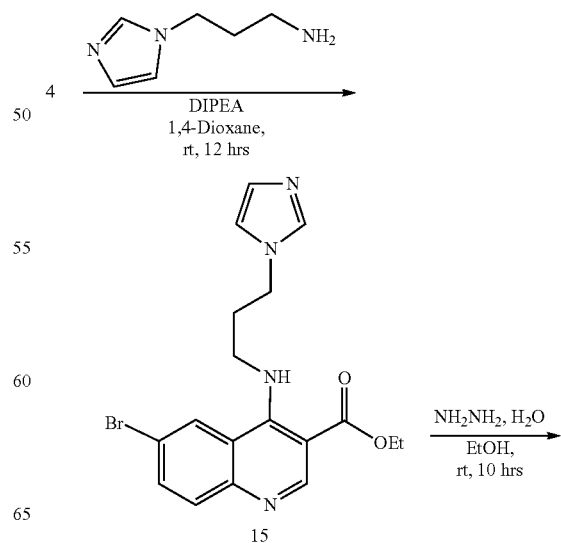

-continued
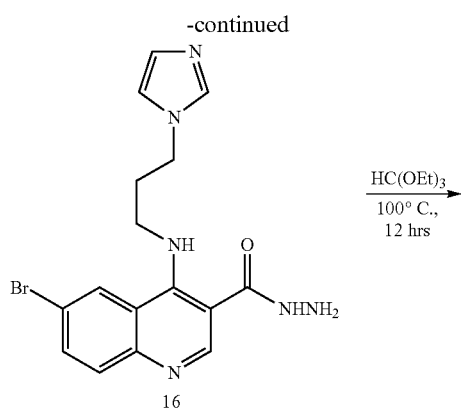
16
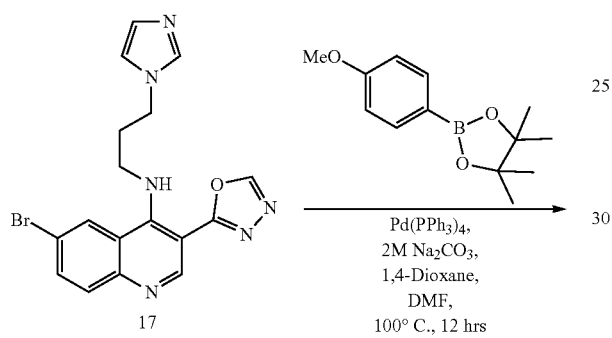
17
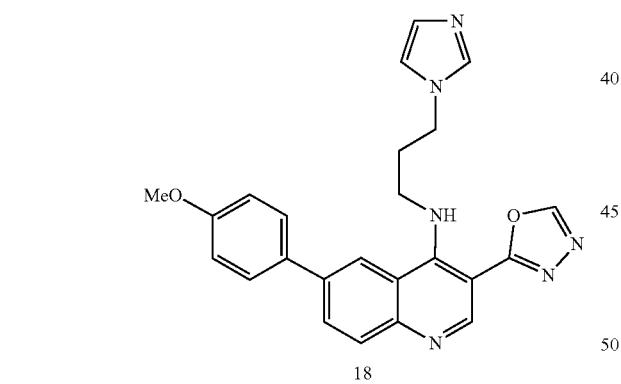
18
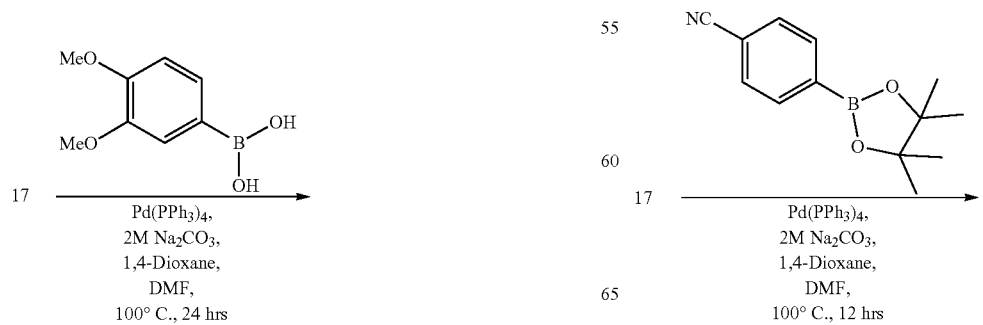
-continued
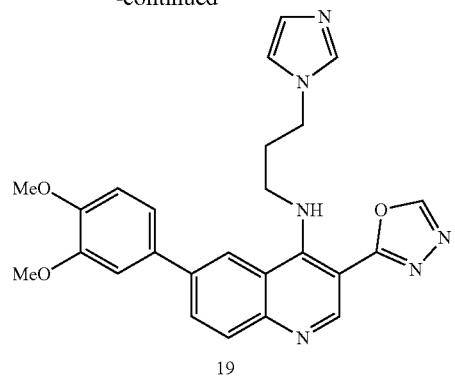
19
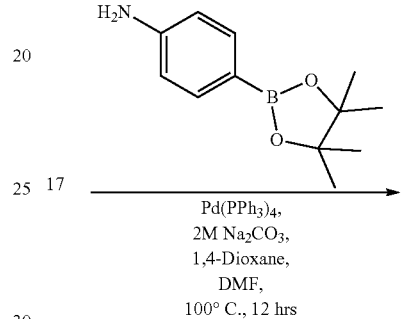
20

-continued
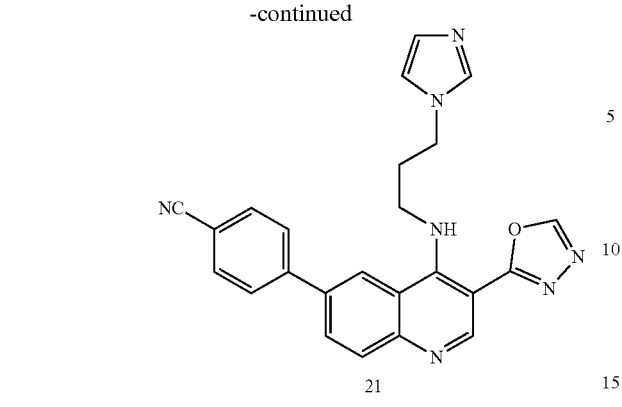
21
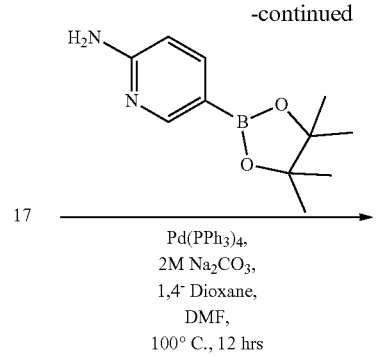
17 →
Pd(PPh₃)₄,
2M Na₂CO₃,
1,4-Dioxane,
DMF,
100° C., 12 hrs
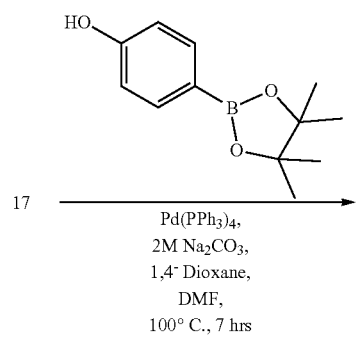
17 →
Pd(PPh₃)₄,
2M Na₂CO₃,
1,4-Dioxane,
DMF,
100° C., 7 hrs
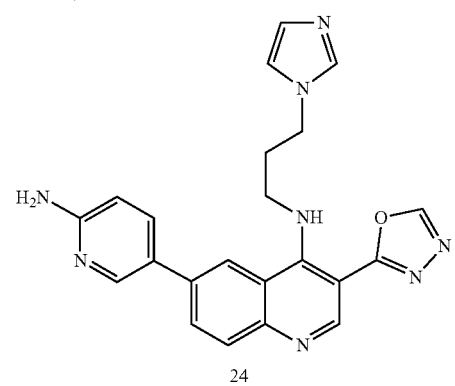
24
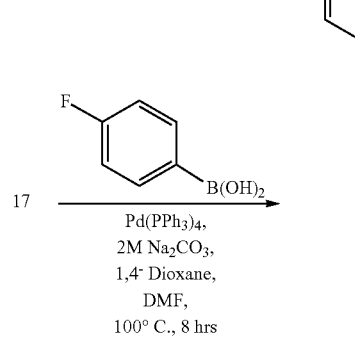
22
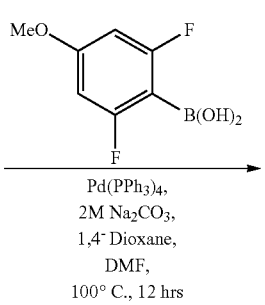
17 →
Pd(PPh₃)₄,
2M Na₂CO₃,
1,4-Dioxane,
DMF,
100° C., 12 hrs
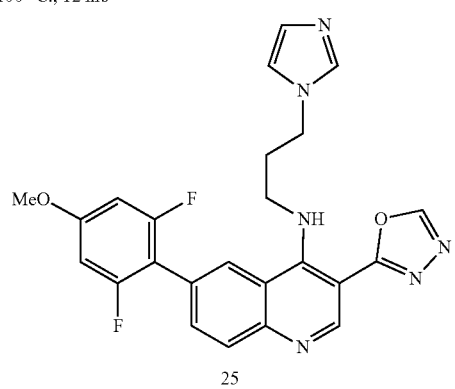
25
17 →
Pd(PPh₃)₄,
2M Na₂CO₃,
1,4-Dioxane,
DMF,
100° C., 8 hrs
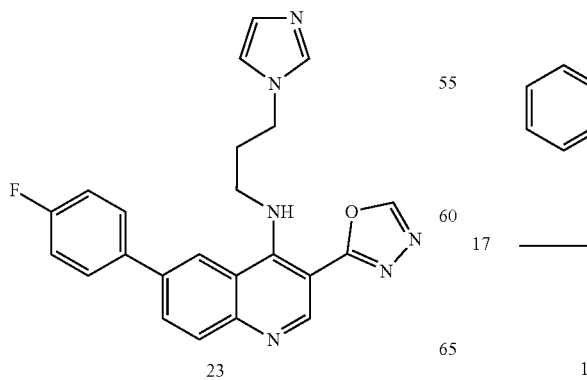
23
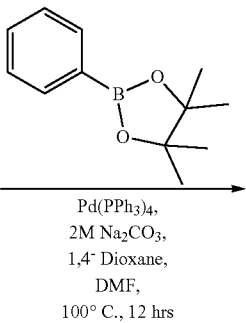
17 →
Pd(PPh₃)₄,
2M Na₂CO₃,
1,4-Dioxane,
DMF,
100° C., 12 hrs -continued
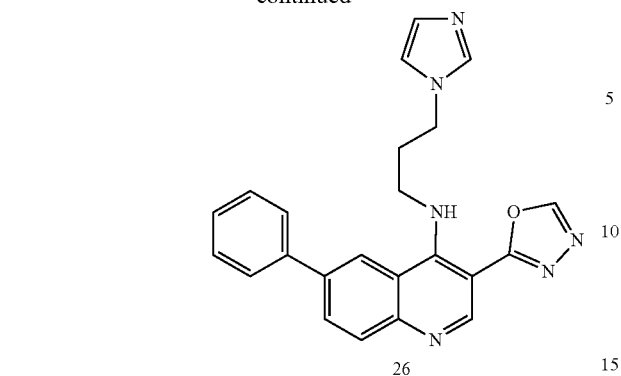
26
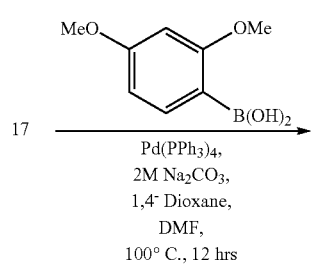
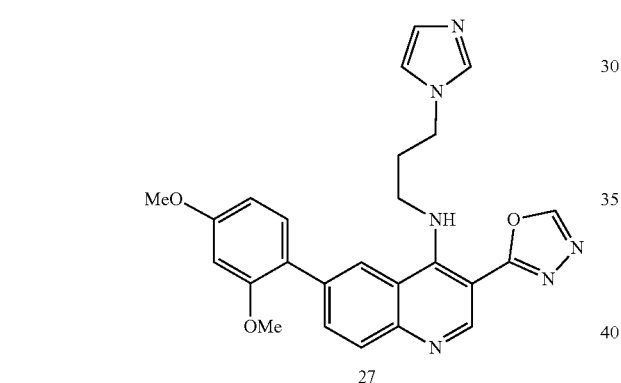
27
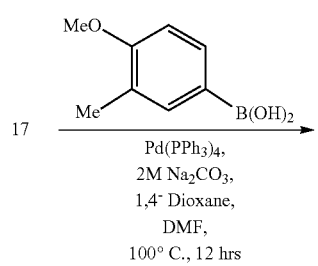
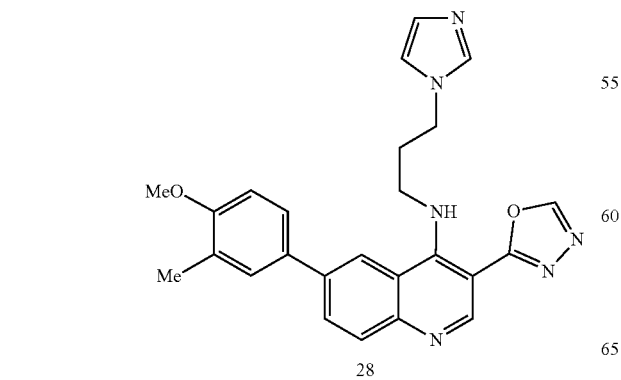
28
-continued
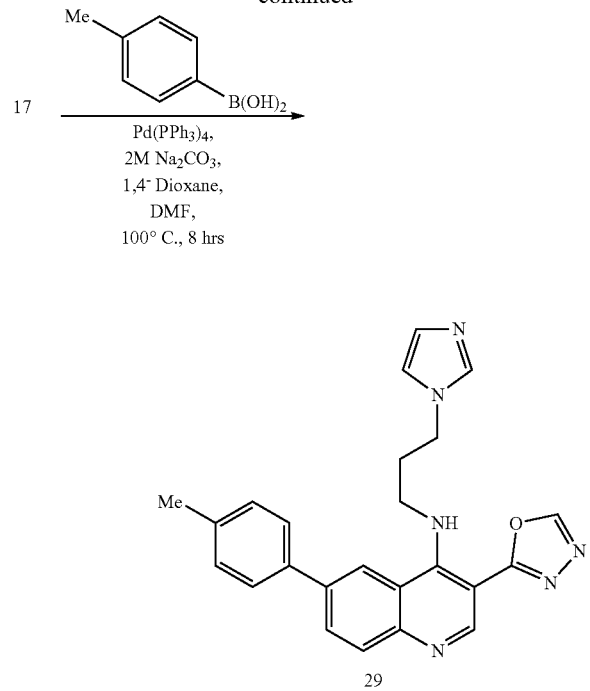
29
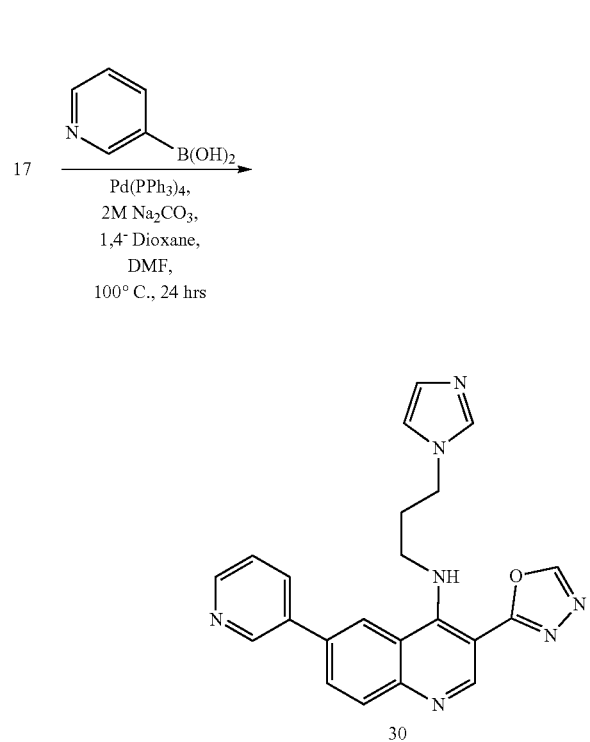
30
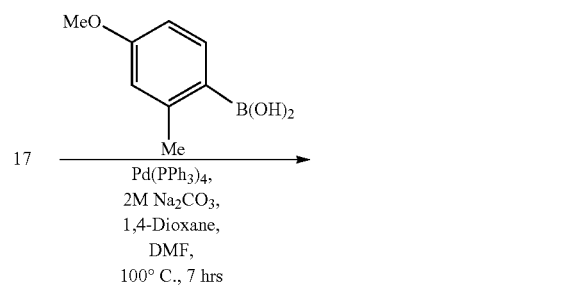

33
-continued
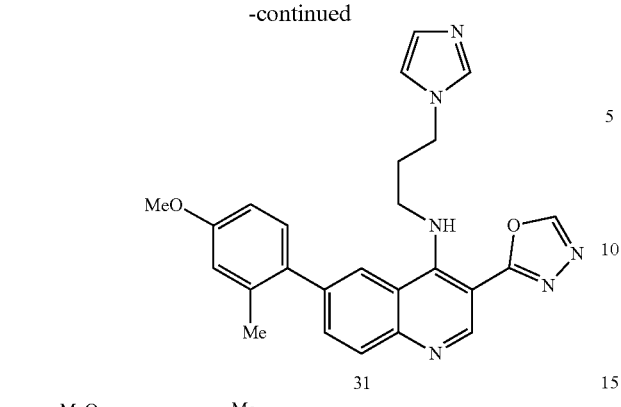
31
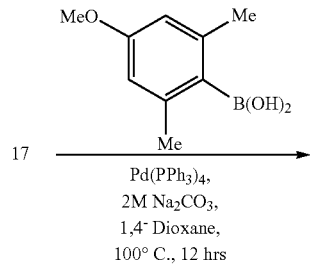
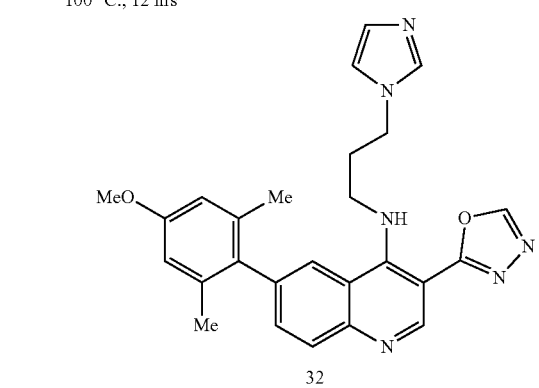
32
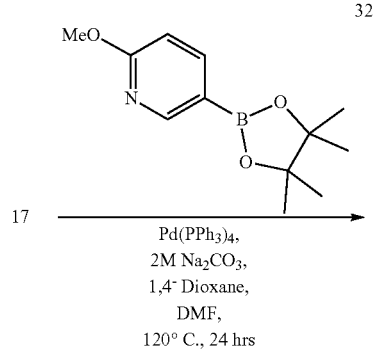
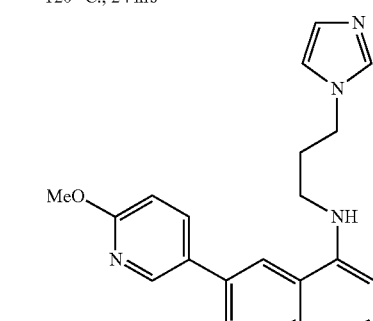
33
34
-continued
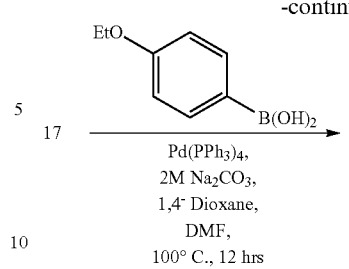
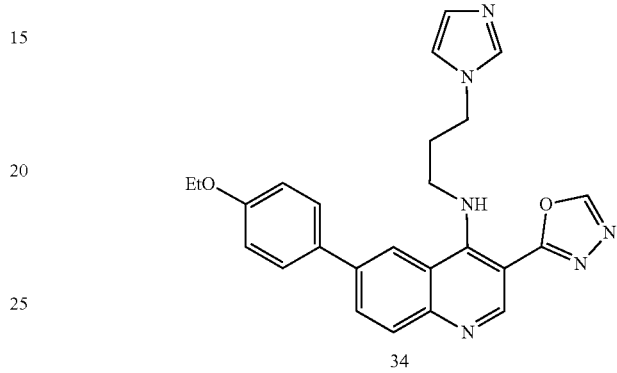
34
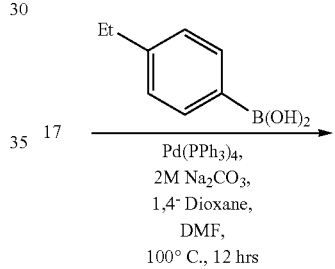
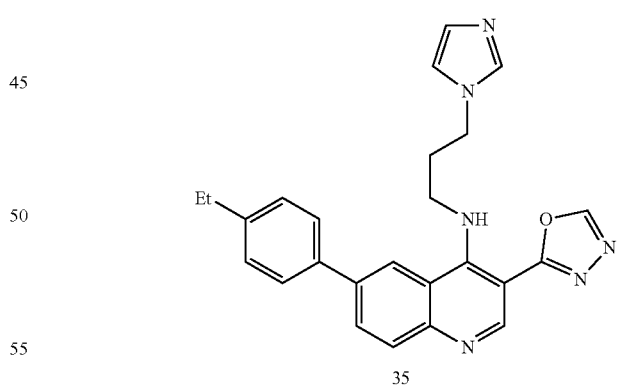
35
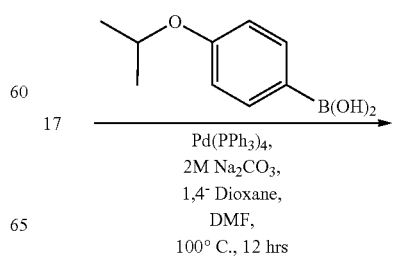

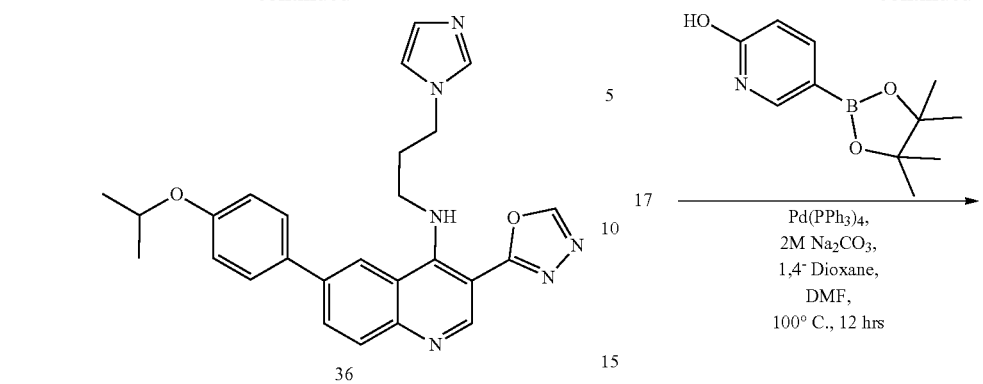
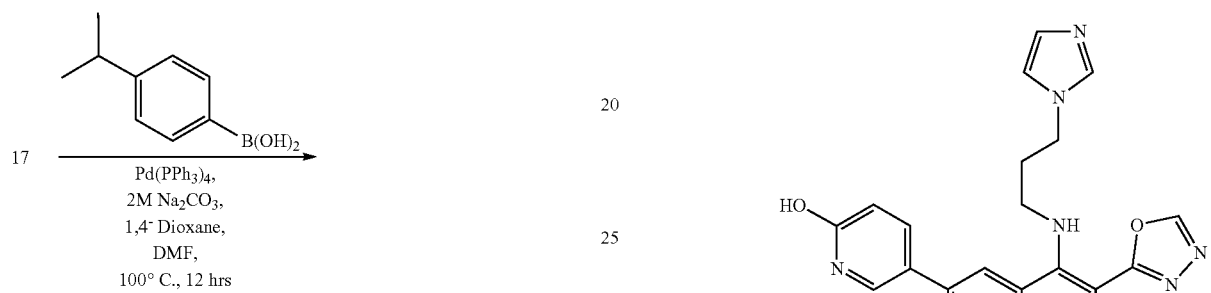
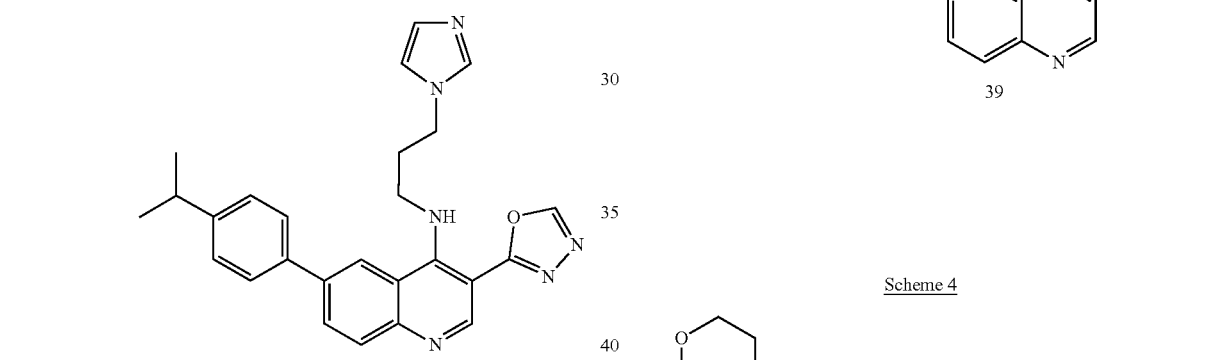
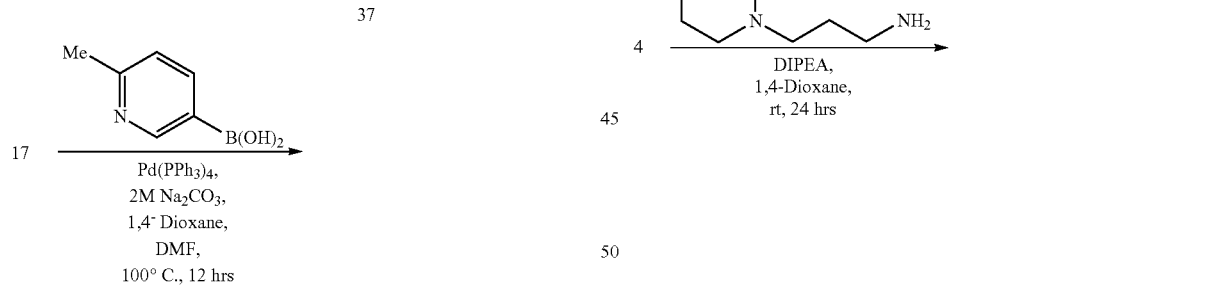
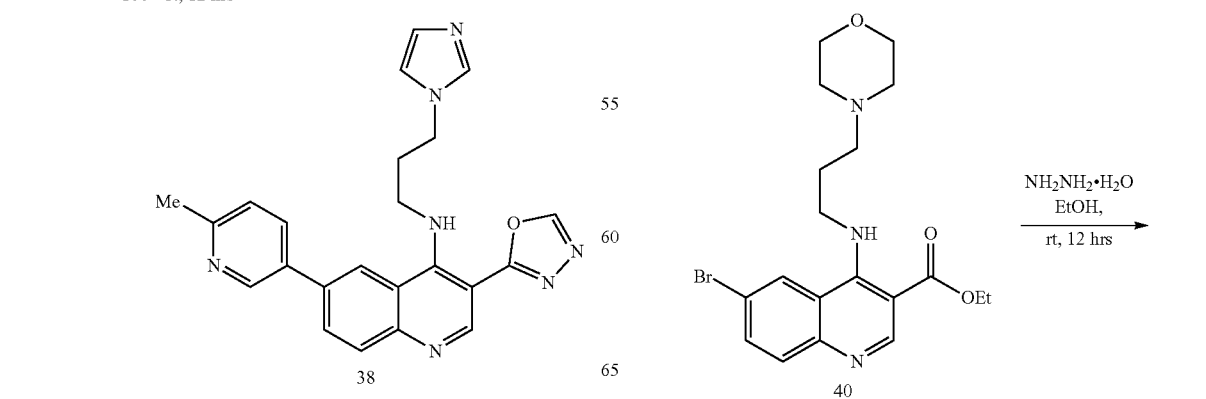

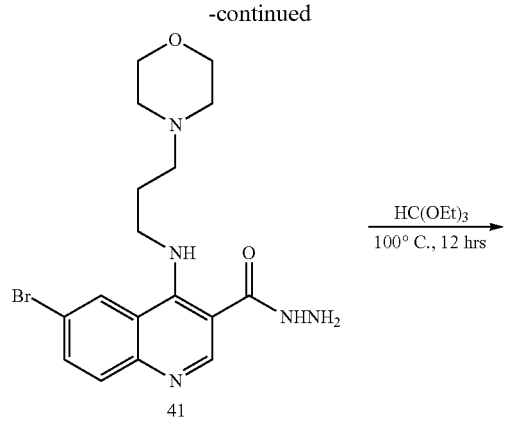
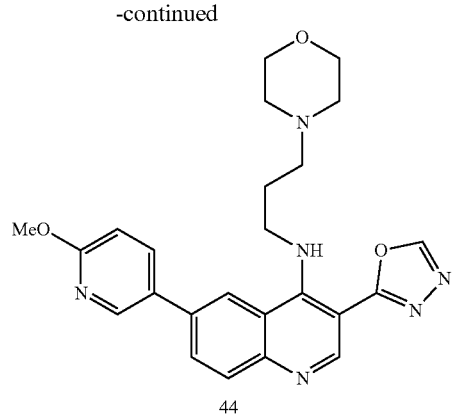
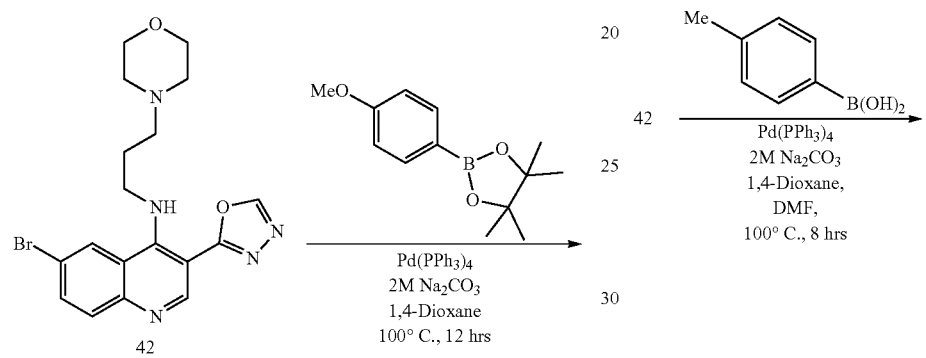
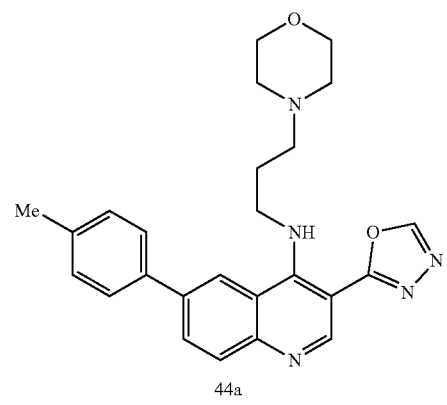
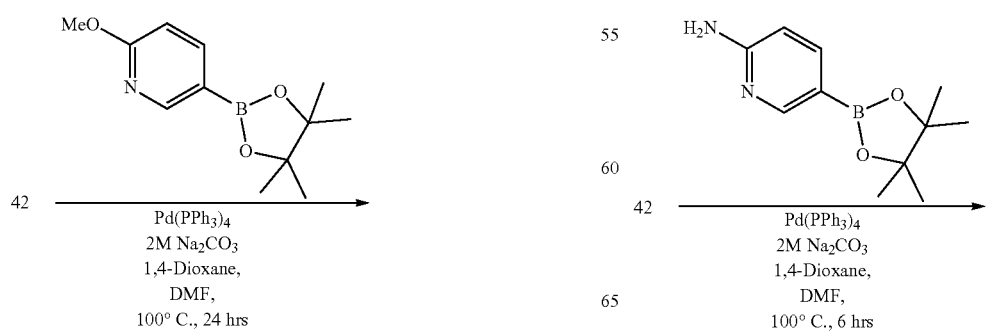

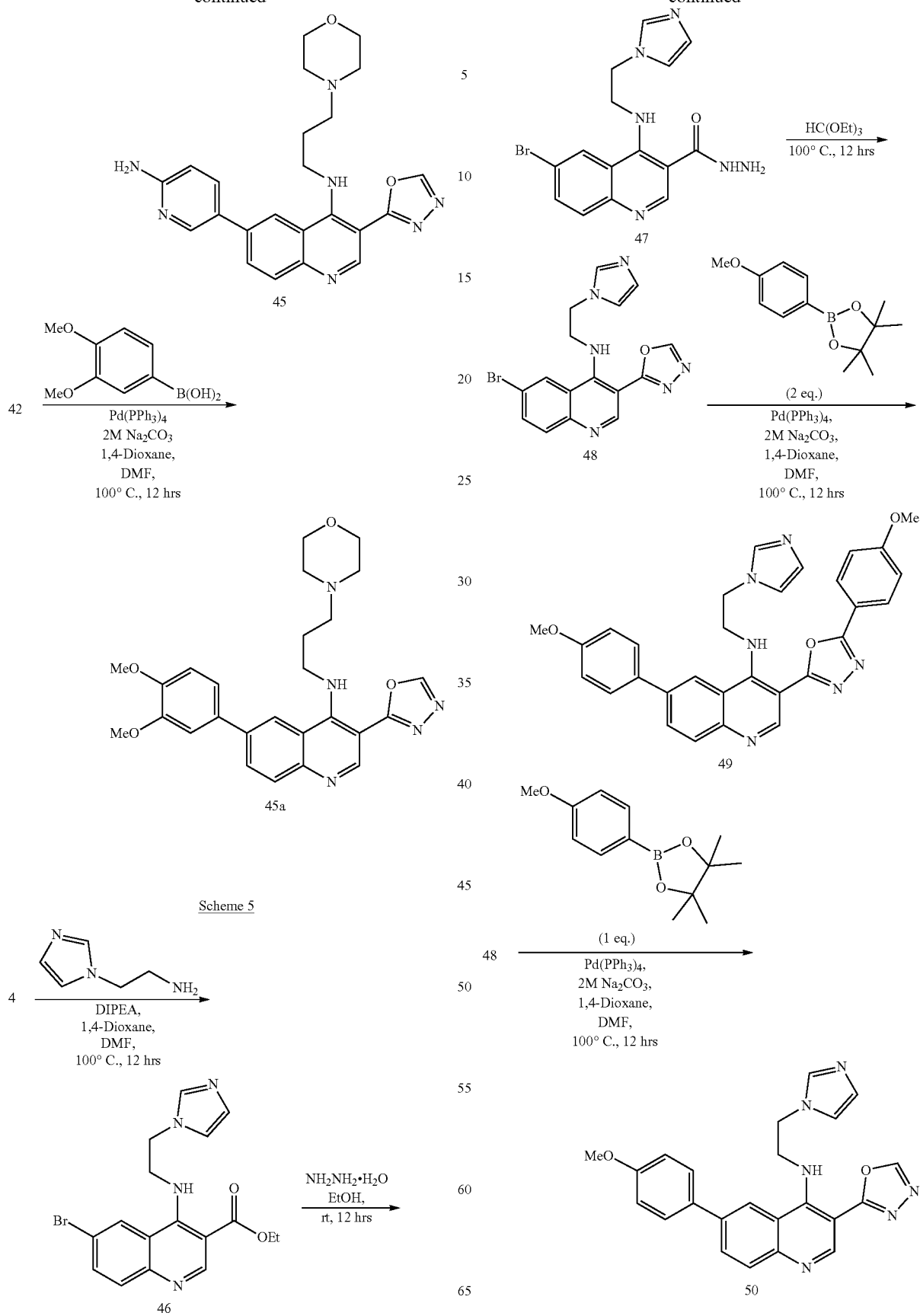

Scheme 6
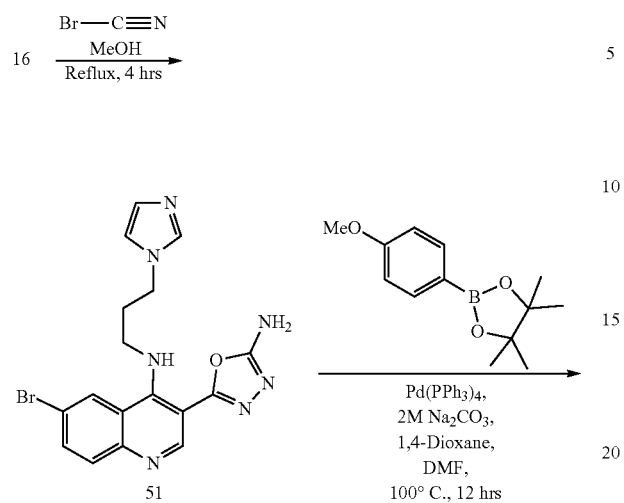
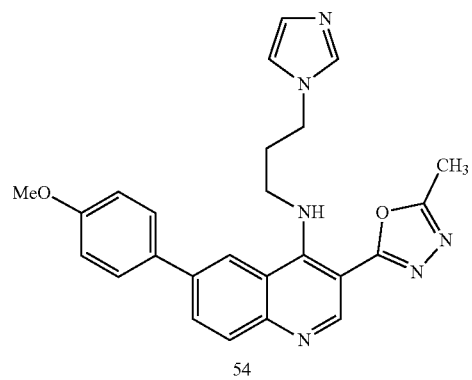
Scheme 7
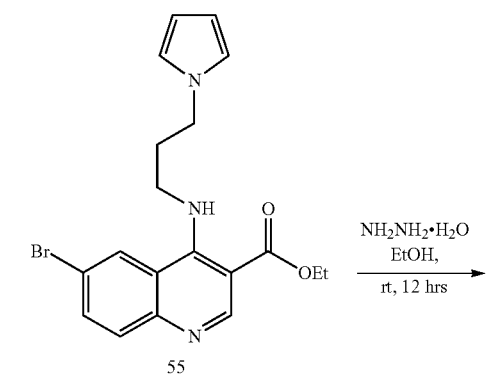
Scheme 8
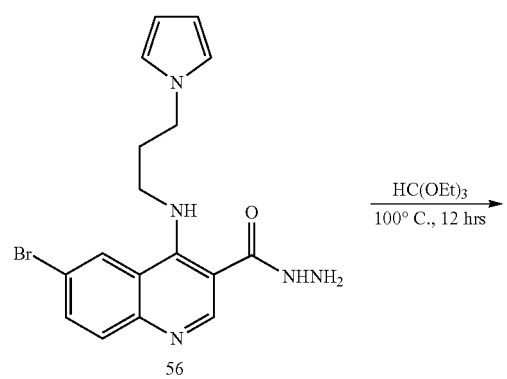

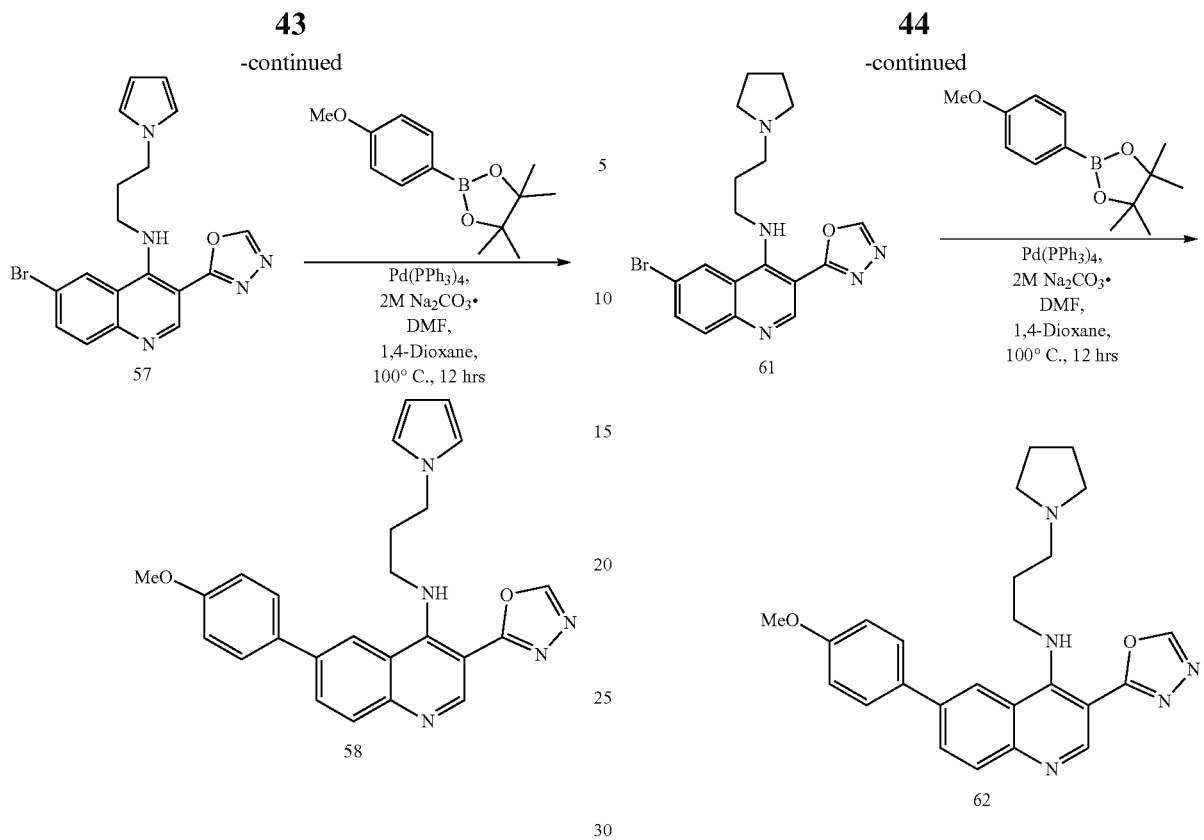
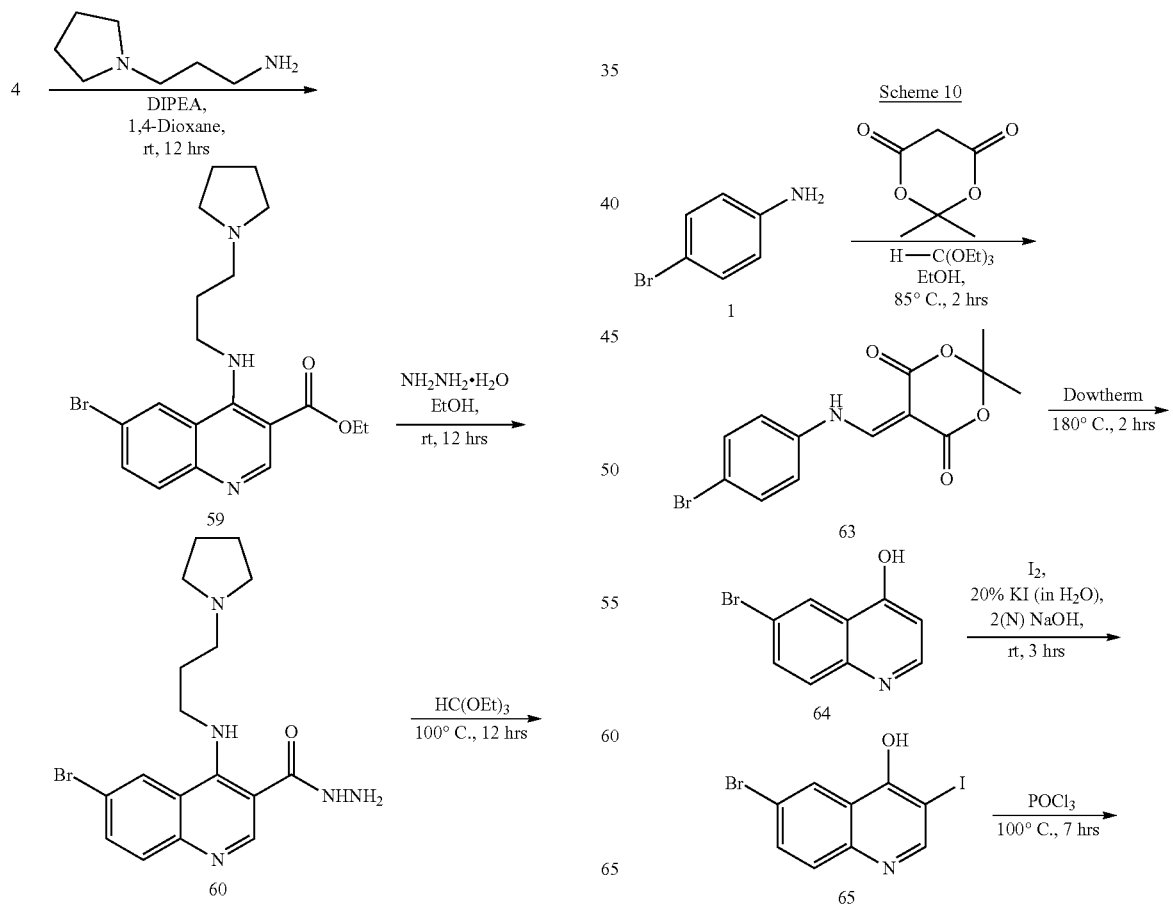

-continued
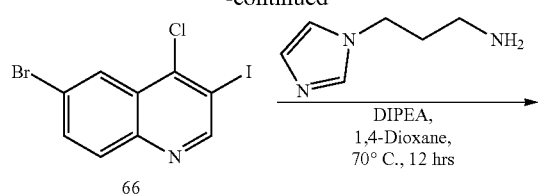
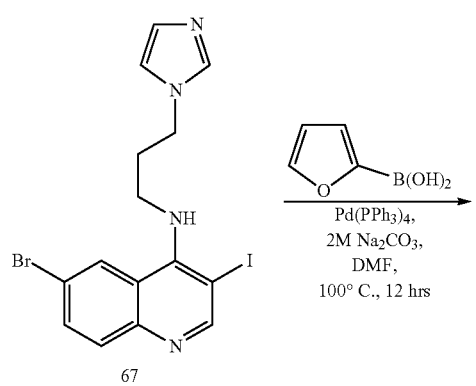
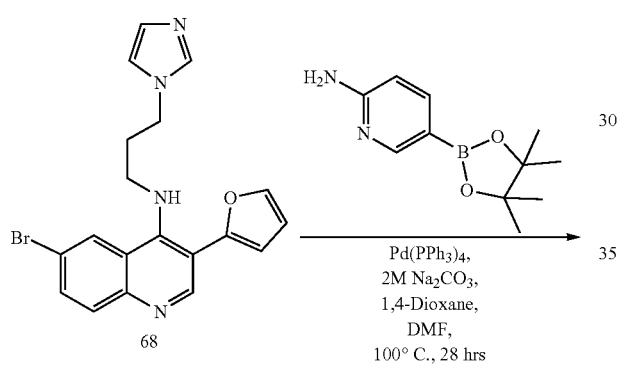
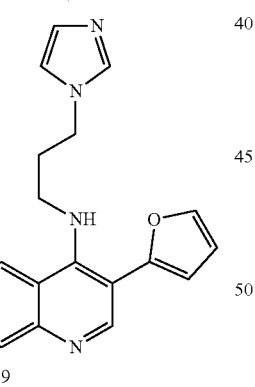
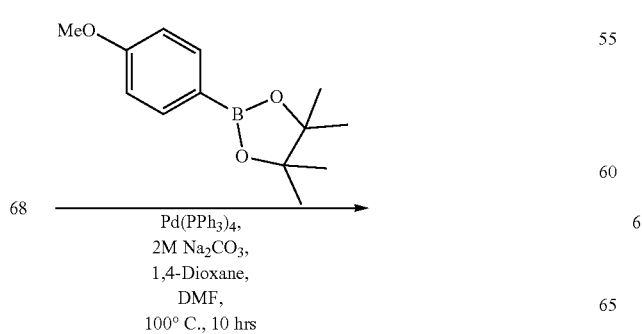
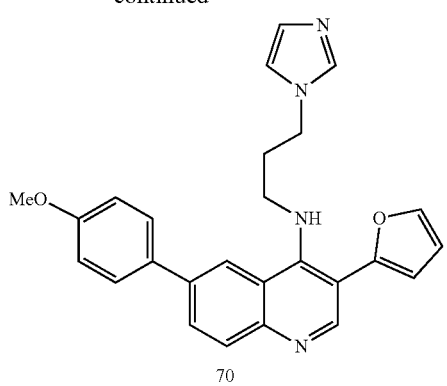
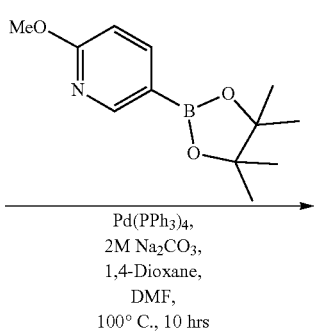
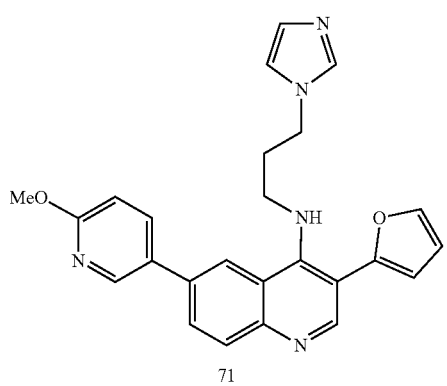
Scheme 11
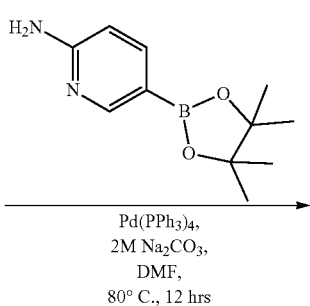

-continued
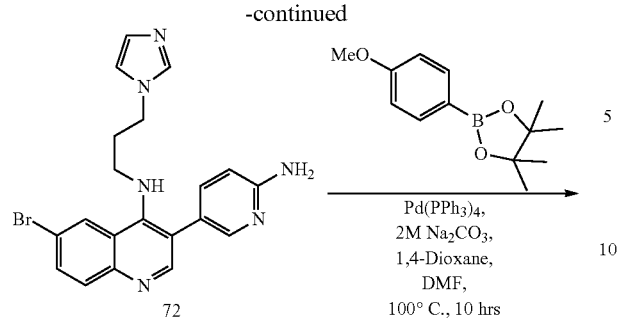
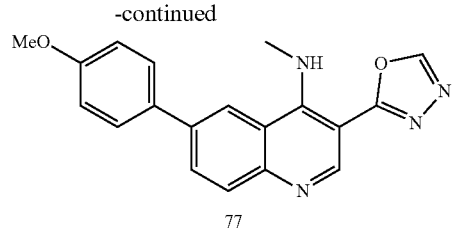
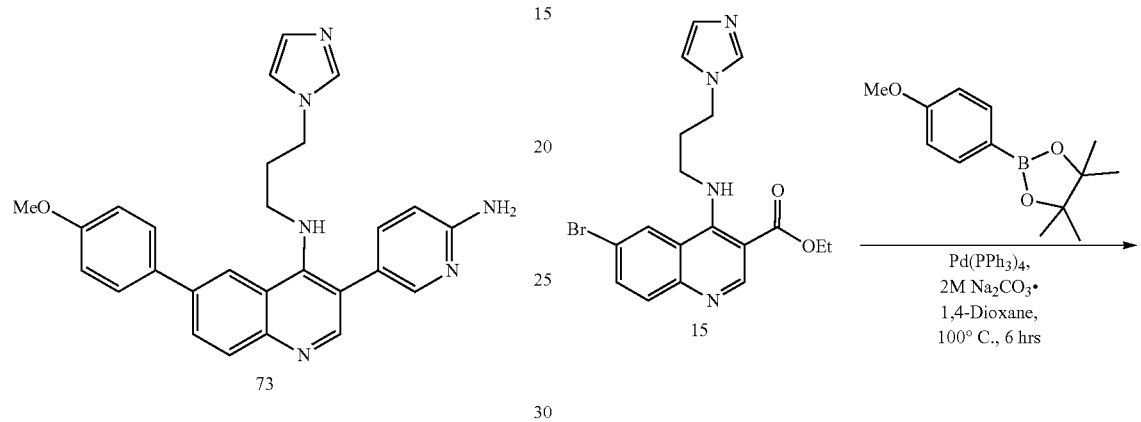
Scheme 13
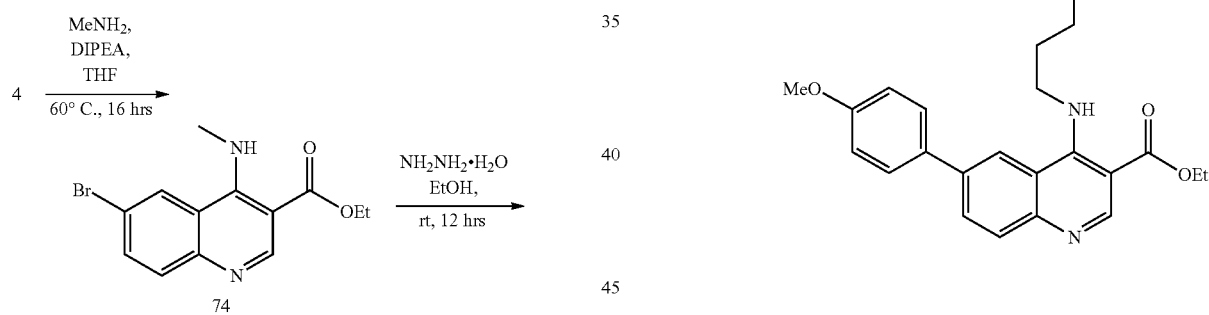
Scheme 12
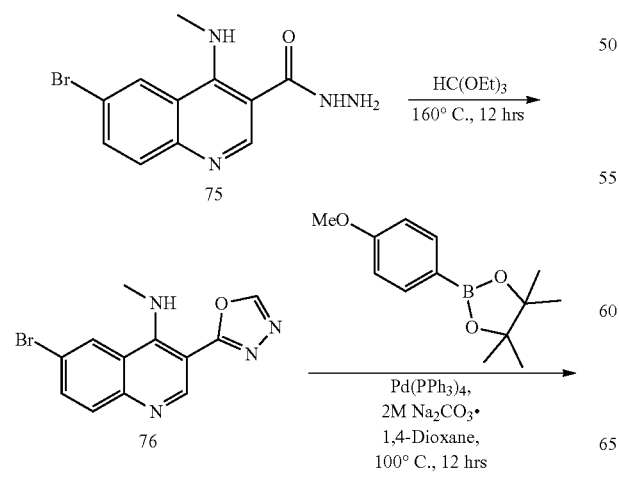
Scheme 14
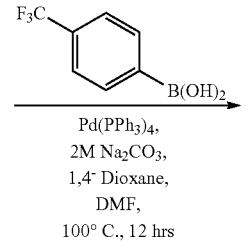

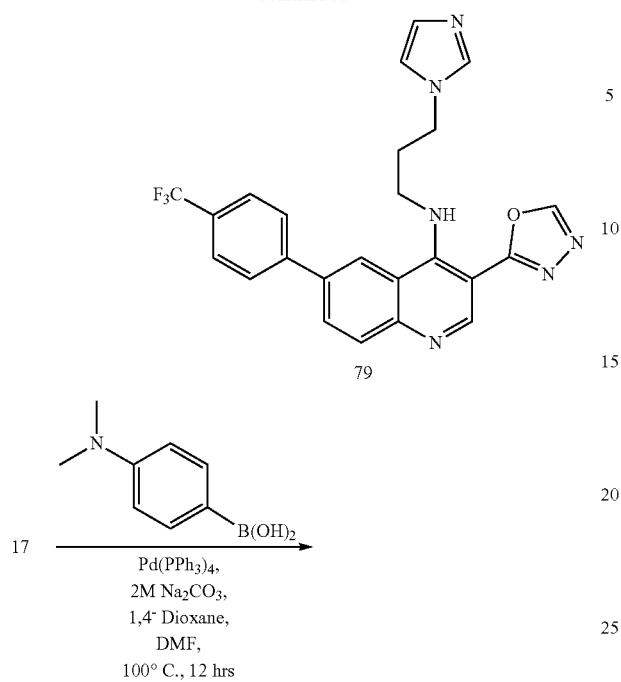
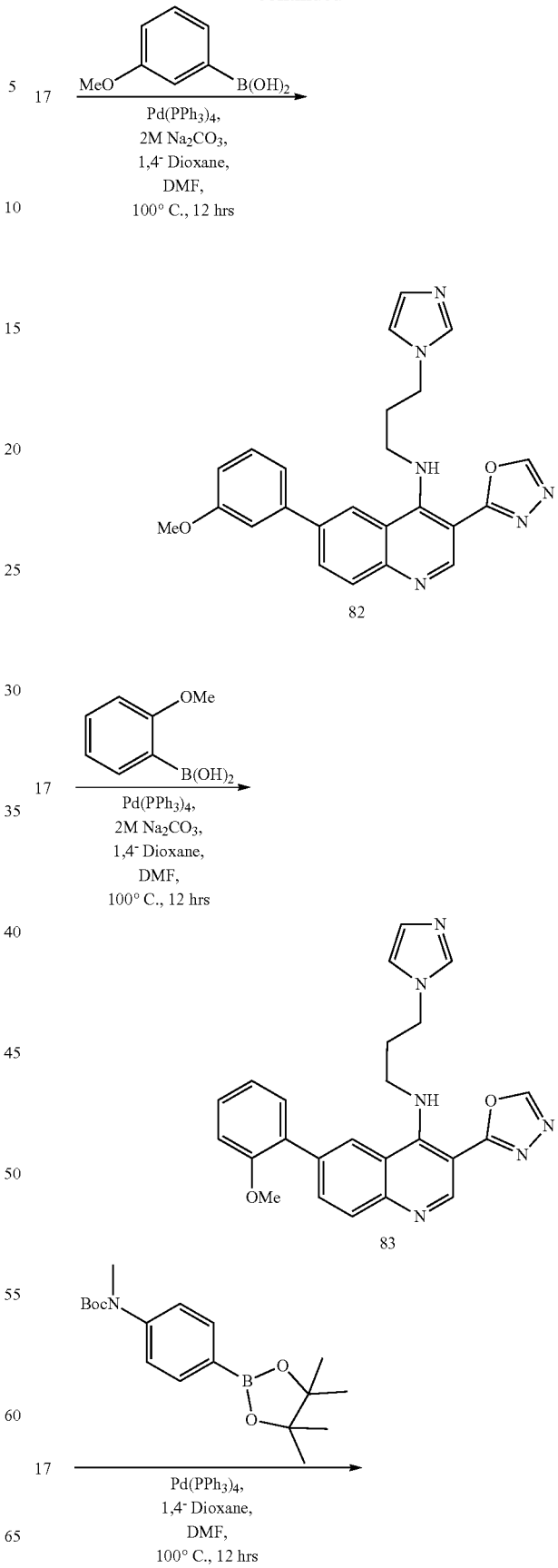

-continued

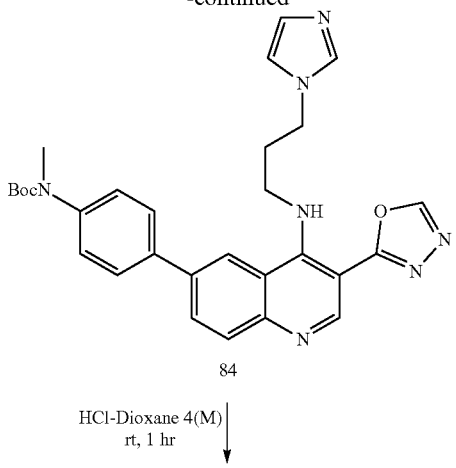

84

HCl-Dioxane 4(M)
rt, 1 hr ↓

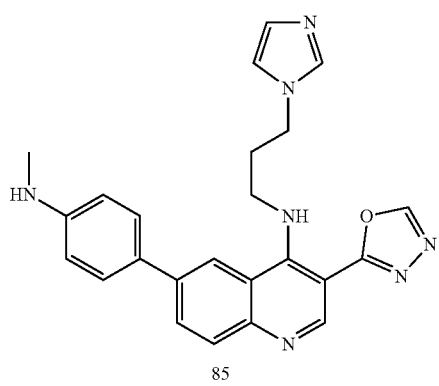

85

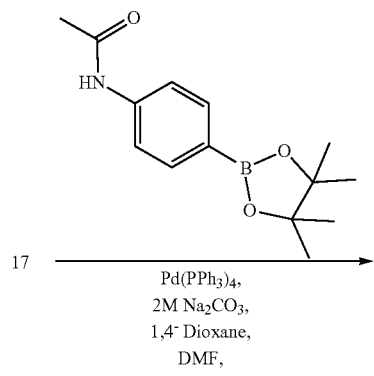

17 →
Pd(PPh₃)₄,
2M Na₂CO₃,
1,4-Dioxane,
DMF,
100° C., 12 hrs

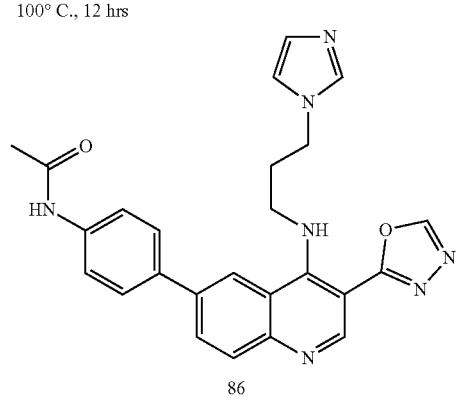

86

EXAMPLES

Following examples are given by way of illustration and therefore should not be construed to limit the scope of the invention.

Example 1A

Synthesis of diethyl 2-((4-bromophenylamino)methylene)malonate (compound 2): 4-Bromoaniline (2 g, 11.63 mmol) was taken in diethyl ethoxymethylenemalonate (2.33 mL, 11.63 mmol) and the reaction mixture was heated for 2 hours at 130° C. A white solid formed which was purified by crystallisation in cyclohexane to give compound 2 (2.8 g, 70%) as white crystals. $^1$H NMR (300 MHz, CDCl$_3$) δ ppm 8.46 (d, J=13.8 Hz, 1H), 7.48 (d, J=8.7 Hz, 2H), 7.02 (d, J=8.4 Hz, 2H), 4.34-4.21 (m, 4H), 1.40-1.31 (m, 6H). ESI-MS m/z 364.16 (M+Na$^+$).

Example 1B

Synthesis of ethyl 6-bromo-4-hydroxyquinoline-3-carboxylate (compound 3): A solution of compound 2 (4 g, 11.69 mmol) in dowtherm (20 mL) solvent [eutectic mixture of 26.5% diphenyl+73.5% diphenyl oxide] was heated for 2.5 hours at 240° C. The reaction mixture was allowed to come to room temperature. Then excess hexane was added to the reaction mixture. A solid formed which was allowed to settle down for 30 minutes. Then the solid was filtered and washed with hexane for several times to remove dowtherm. The solid was dried to give compound 3 (2 g, 58%) as a light brown solid. $^1$H NMR (300 MHz, DMSO-d$_6$) δ ppm 8.60 (s, 1H), 8.19 (dd, J=19, 1.2 Hz, 1H), 7.87 (dd, J=9, 2.4 Hz, 1H), 7.60 (d, J=8.7 Hz, 1H), 4.22 (q, J=7.2 Hz, 2H), 1.28 (t, J=7.2 Hz, 3H). EI-MS m/z 295 (M+H$^+$).

Example 1C

Synthesis of ethyl 6-bromo-4-chloroquinoline-3-carboxylate (compound 4): Compound 3 (2 g, 6.75 mmol) was taken in POCl$_3$ (15 mL) in ice-cold condition. The reaction mixture was allowed to come to room temperature and then heated for 2 hours at 100° C. Then the reaction mixture was poured into crushed ice and neutralised with saturated sodium bicarbonate solution. The organic part was extracted with ethyl acetate, washed with water and brine, concentrated and dried. The solid was purified by silica gel flash column chromatography, eluting with 15% ethyl acetate in hexane to give compound 4 (1.8 g, 85%) as a white crystalline solid. $^1$H NMR (300 MHz, CDCl$_3$) δ ppm 9.2 (s, 1H), 8.58 (d, J=2.4 Hz, 1H), 8.02 (d, J=9.3 Hz, 1H), 7.92 (dd, J=9, 1.8 Hz, 1H), 4.51 (q, J=7.5 Hz, 2H), 1.47 (t, J=7.5 Hz, 3H). ESI-MS m/z 338.16 (M+Na$^+$).

Example 1D

Synthesis of ethyl 6-bromo-4-(2-morpholinoethylamino) quinoline-3-carboxylate (compound 5): Compound 4 (1 g, 3.18 mmol) was dissolved in 1,4-dioxane (5 mL) under N$_2$ atmosphere. To the reaction mixture dry DIPEA (1.11 mL, 6.36 mmol) and 4-(2-aminoethyl)morpholine (0.63 mL, 4.77 mmol) were added respectively. The reaction mixture was allowed to stir for 12 hours at room temperature. Then it was poured into 50 mL water. The solid obtained was filtered and purified by column chromatography to give compound 5 (1.1 g, 85%) as a white solid. $^1$H NMR (300 MHz, CDCl$_3$) δ ppm 9.51 (br. s, —NH), 9.1 (s, 1H), 8.4 (d, J=1.5 Hz, 1H), 7.83 (d, J=9 Hz, 1H), 7.73 (dd, J=8.7, 1.8 Hz, 1H), 4.41 (q, J=7.2 Hz, 2H), 3.92-3.87 (m, 2H), 3.78 (t, J=4.5 Hz, 4H), 2.71 (t, J=6 Hz, 2H), 2.57 (t, J=4.2 Hz, 4H), 1.44 (t, J=7.5 Hz, 3H). ESI-MS m/z 410.35 (M+H$^+$).

Example 1E

Synthesis of 6-bromo-4-(2-morpholinoethylamino)quinoline-3-carbohydrazide (compound 6): Compound 5 (1 g, 2.45 mmol) was dissolved in ethanol (10 mL). To the solution hydrazine hydrate (10 mL) was added. The reaction mixture was stirred for 10 hours at room temperature. Ethanol was removed under vacuum. The residue was then dissolved in CHCl$_3$ and the organic layer was washed with water and brine, dried and concentrated to give compound 6 (0.6 g, 62%) as a yellow solid. $^1$H NMR (300 MHz, CDCl$_3$) δ ppm 8.64 (s, 1H), 8.27 (d, J=1.5 Hz, 1H), 7.84 (d, J=8.7 Hz, 1H), 7.73 (dd, J=8.7, 1.5 Hz, 1H), 3.77 (t, J=4.8 Hz, 4H), 3.70-3.65 (m, 2H), 2.68 (t, J=6.3 Hz, 2H), 2.54 (t, J=4.2 Hz, 4H). ESI-MS m/z 394.41 (M+H$^+$).

Example 1F

Synthesis of 6-bromo-N-(2-morpholinoethyl)-3-(1,3,4-oxadiazol-2-yl)quinolin-4-amine (compound 7): Compound 6 (1 g, 2.54 mmol) was taken in triethylorthoformate (5 mL, 30.06 mmol) and the mixture was heated for 12 hours at 110° C. Then the reaction mixture was allowed to come to room temperature. Excess hexane was added to the mixture. A precipitation formed which was filtered and purified by column chromatography, eluting with 1% methanol in CHCl$_3$ to give compound 7 (0.4 g, 39%) as a light yellow solid. $^1$H NMR (300 MHz, CDCl$_3$) δ ppm 9.22 (br. s, —NH), 9.03 (s, 1H), 8.47 (m, 2H), 7.86 (d, J=8.7 Hz, 1H), 7.75 (dd, J=8.7, 1.8 Hz, 1H), 4.00-3.95 (m, 2H), 3.77 (t, J=4.5 Hz, 4H), 2.74 (t, J=6 Hz, 2H), 2.58 (t, J=4.5 Hz, 4H). ESI-MS m/z 404.37 (M+H$^+$).

Example 1

Synthesis of 6-(3,4-dimethoxyphenyl)-N-(2-morpholinoethyl)-3-(1,3,4-oxadiazol-2-yl)quinolin-4-amine (compound 8): Compound 7 (0.10 g, 0.25 mmol) was dissolved in 1,4-dioxane (5 mL) under Ar (argon) atmosphere. Then 3,4-dimethoxyphenylboronic acid (0.091 g, 0.5 mmol) was added to the mixture. 2(M) Na$_2$CO$_3$ solution (0.3 mL) was added to the reaction mixture and Ar was purged for 5 minutes. Then Pd(PPh$_3$)$_4$(0.023 g, 0.02 mmol) was added to the reaction mixture and Ar purging was performed for about 10 minutes. Then the mixture was heated for 12 hours at 100° C. 1,4-Dioxane was removed under vacuum, the residue then dissolved in CHCl$_3$ and the organic layer was washed with water and brine, dried and concentrated. The residue was purified by column chromatography, eluting with 5% methanol in CHCl$_3$ to give compound 8 (0.035 g, 31%) as a yellow solid. mp 116° C. $^1$H NMR (300 MHz, CDCl$_3$) δ ppm 9.21 (br. s, —NH), 9.06 (s, 1H), 8.51 (s, 1H), 8.45 (d, J=1.5 Hz, 1H), 8.07 (d, J=8.7 Hz, 1H), 7.93 (dd, J=8.7, 1.8 Hz, 1H), 7.25 (dd, J=8.7, 1.8 Hz, 1H), 7.19 (d, J=2.1 Hz, 1H), 7.03 (d, J=8.4 Hz, 1H), 4.11-4.06 (m, 2H), 4.01 (s, 3H), 3.98 (s, 3H), 3.77 (t, J=4.5 Hz, 4H), 2.76 (t, J=6 Hz, 2H), 2.58 (t, J=4.5 Hz, 4H). ESI-MS m/z 461.51 (M+H$^+$).

Example 2

Synthesis of 6-(4-methoxyphenyl)-N-(2-morpholinoethyl)-3-(1,3,4-oxadiazol-2-yl)quinolin-4-amine (compound 9): Compound 7 (0.15 g, 0.37 mmol) was taken along with 2-(4-methoxyphenyl)-4,4,5,5-tetramethyl-1,3,2-dioxaborolane (0.17 g, 0.74 mmol) in 1,4-dioxane (6 mL). 2(M) Na$_2$CO$_3$ solution (0.5 mL) and Pd(PPh$_3$)$_4$(0.035 g, 0.03 mmol) were added to the mixture and the reaction was performed according to Example 1. The residue was purified by silica gel column chromatography to produce compound 9 (0.09 g, 56%) as a white solid. mp 156° C. $^1$H NMR (600 MHz, CDCl$_3$) δ ppm 9.05 (s, 1H), 8.49 (s, 1H), 8.45 (d, J=1.2 Hz, 1H), 8.06 (d, J=8.4 Hz, 1H), 7.94 (dd, J=8.4, 1.2 Hz, 1H), 7.62 (d, J=9 Hz, 2H), 7.05 (d, J=8.4 Hz, 2H), 4.10-4.07 (m, 2H), 3.89 (s, 3H), 3.77 (t, J=4.8 Hz, 4H), 2.76 (t, J=6 Hz, 2H), 2.58 (br. s, 4H). ESI-MS m/z 432.42 (M+H$^+$).

Example 3

Synthesis of 6-(4-methyl-3-nitrophenyl)-N-(2-morpholinoethyl)-3-(1,3,4-oxadiazol-2-yl)quinolin-4-amine (compound 10): Compound 7 (0.10 g, 0.25 mmol) was taken along with 4-methyl-3-nitrophenylboronic acid (0.11 g, 0.63 mmol) in 1,4-dioxane (5 mL). 2(M) Na$_2$CO$_3$ solution (0.3 mL) and Pd(PPh$_3$)$_4$(0.023 g, 0.02 mmol) were added to the mixture and the reaction was performed according to Example 1. The residue was purified by silica gel column chromatography, eluting with 2% methanol in CHCl$_3$ to produce compound 10 (0.03 g, 26%) as a yellow solid. mp 222° C. $^1$H NMR (300 MHz, CDCl$_3$) δ ppm 9.31 (br. s, —NH), 9.09 (s, 1H), 8.50 (s, 2H), 8.27 (d, J=1.5 Hz, 1H), 8.12 (d, J=8.7 Hz, 1H), 7.81 (dd, J=7.8, 1.8 Hz, 1H), 7.49 (d, J=7.8 Hz, 1H), 4.10-4.04 (m, 2H), 3.77 (t, J=4.5 Hz, 4H), 2.76 (t, J=6 Hz, 2H), 2.68 (s, 3H), 2.58 (t, J=4.2 Hz, 4H). ESI-MS m/z 461.23 (M+H$^+$).

Example 4

Synthesis of 4-(4-(2-morpholinoethylamino)-3-(1,3,4-oxadiazol-2-yl)quinolin-6-yl)benzonitrile (compound 11): Compound 7 (0.10 g, 0.25 mmol) was taken along with 4-(4,4,5,5-tetramethyl-1,3,2-dioxaborolan-2-yl)benzonitrile (0.12 g, 0.5 mmol) in 1,4-dioxane (5 mL). 2(M) Na$_2$CO$_3$ solution (0.3 mL) and Pd(PPh$_3$)$_4$(0.023 g, 0.02 mmol) were added to the mixture and the reaction was performed according to Example 1. The residue was purified by silica gel column chromatography, eluting with 2% methanol in CHCl$_3$ to produce compound 11 (0.025 g, 24%) as a white solid. mp 190° C. $^1$H NMR (600 MHz, CDCl$_3$) δ ppm 8.98 (s, 1H), 8.61 (s, 1H), 8.49 (s, 1H), 8.08 (d, J=9 Hz, 1H), 7.94 (d, J=9 Hz, 1H), 7.76-7.72 (m, 4H), 4.07 (br. s, 2H), 3.74 (br. s, 4H), 2.75 (br. s, 2H), 2.57 (br. s, 4H). ESI-MS m/z 427.43 (M+H$^+$).

Example 5A

Synthesis of 6-bromo-3-(5-methyl-1,3,4-oxadiazol-2-yl)-N-(2-morpholinoethyl)quinolin-4-amine (compound 12): Compound 6 (0.15 g, 0.38 mmol) was dissolved in ethanol (3 mL) and to the solution triethyl orthoacetate (3 mL, 16.37 mmol) was added. The reaction mixture was heated for 8 hours at 110° C. Then the reaction mixture was allowed to come to room temperature and solvent was evaporated. Excess hexane was added to the mixture. A precipitation formed which was filtered and purified by column chromatography, eluting with 3% methanol in CHCl$_3$ to give compound 12 (0.14 g, 88%) as a brown solid. H NMR (300 MHz, CDCl$_3$) δ ppm 9.17 (br. s, —NH), 8.99 (s, 1H), 8.48 (d, J=1.8 Hz, 1H), 7.86 (d, J=8.7 Hz, 1H), 7.74 (dd, J=8.7, 2.1 Hz, 1H), 4.00-3.94 (m, 2H), 3.78 (t, J=4.5 Hz, 4H), 2.75 (t, J=6 Hz, 2H), 2.68 (s, 3H), 2.59 (t, J=4.5 Hz, 4H). ESI-MS m/z 418.37 (M+H$^+$).

Example 5

Synthesis of 6-(3,4-dimethoxyphenyl)-3-(5-methyl-1,3,4-oxadiazol-2-yl)-N-(2-morpholinoethyl)quinolin-4-amine (compound 13): Compound 12 (0.065 g, 0.16 mmol) was taken along with 3,4-dimethoxyphenylboronic acid (0.073 g, 0.4 mmol) in 1,4-dioxane (5 mL). 2(M) Na$_2$CO$_3$ solution (0.3 mL) and Pd(PPh$_3$)$_4$ (0.015 g, 0.013 mmol) were added to the mixture and the reaction was performed according to Example 1. The residue was purified by silica gel column chromatography, eluting with 3% methanol in CHCl$_3$ to produce compound 13 (0.03 g, 41%) as a light yellow solid. mp 180° C. $^1$H NMR (300 MHz, CDCl$_3$) δ ppm 9.11 (br. s, —NH), 8.99 (s, 1H), 8.42 (s, 1H), 8.05 (d, J=8.7 Hz, 1H), 7.90 (dd, J=8.4, 1.5 Hz, 1H), 7.24 (dd, J=8.1, 1.5 Hz, 1H), 7.17 (d, J=1.5 Hz, 1H), 7.01 (d, J=8.4 Hz, 1H), 4.08-4.03 (m, 2H), 3.99 (s, 3H), 3.96 (s, 3H), 3.75 (t, J=4.5 Hz, 4H), 2.74 (t, J=6 Hz, 2H), 2.68 (s, 3H), 2.56 (t, J=4.5 Hz, 4H). ESI-MS m/z 462.40 (M+H$^+$).

Example 6

Synthesis of 6-(4-methoxyphenyl)-3-(5-methyl-1,3,4-oxadiazol-2-yl)-N-(2-morpholinoethyl)quinolin-4-amine (compound 14): Compound 12 (0.075 g, 0.18 mmol) was taken along with 2-(4-methoxyphenyl)-4,4,5,5-tetramethyl-1,3,2-dioxaborolane (0.17 g, 0.36 mmol) in 1,4-dioxane (5 mL). 2(M) Na$_2$CO$_3$ solution (0.23 mL) and Pd(PPh$_3$)$_4$(0.017 g, 0.014 mmol) were added to the mixture and the reaction was performed according to Example 1. The residue was purified by silica gel column chromatography, eluting with 2% methanol in CHCl$_3$ to produce compound 14 (0.025 g, 31%) as an off-white solid. mp 160° C. $^1$H NMR (300 MHz, CDCl$_3$) δ ppm 9.14 (br. s, —NH), 8.99 (s, 1H), 8.44 (d, J=1.5 Hz, 1H), 8.05 (d, J=8.7 Hz, 1H), 7.92 (dd, J=8.7, 1.5 Hz, 1H), 7.63 (d, J=8.7 Hz, 2H), 7.05 (d, J=8.7 Hz, 2H), 4.09-4.04 (m, 2H), 3.90 (s, 3H), 3.76 (t, J=4.5 Hz, 4H), 2.75 (t, J=6 Hz, 2H), 2.69 (s, 3H), 2.57 (t, J=4.2 Hz, 4H). ESI-MS m/z 432.42 (M+H$^+$).

Example 7A

Synthesis of ethyl 4-((3-(1H-imidazol-1-yl)propyl)amino)-6-bromoquinoline-3-carboxylate (compound 15): Compound 4 (1 g, 3.18 mmol) was dissolved in 1,4-dioxane (5 mL) under N$_2$ atmosphere. To the reaction mixture dry DIPEA (1.11 mL, 6.36 mmol) and 3-(1H-imidazol-1-yl)propan-1-amine (0.57 mL, 4.77 mmol) were added respectively. The reaction mixture was allowed to stir for 12 hours at room temperature. Then it was poured into 50 mL water. The solid obtained was filtered and dried to give compound 15 (1.2 g, 94%) as a white solid. $^1$H NMR (600 MHz, CDCl$_3$) δ ppm 9.29 (t, J=4.8 Hz, —NH), 9.10 (s, 1H), 8.23 (d, J=2.4 Hz, 1H), 7.82 (d, J=9 Hz, 1H), 7.73 (dd, J=9, 1.8 Hz, 1H), 7.46 (s, 1H), 7.06 (s, 1H), 6.90 (s, 1H), 4.41 (q, J=7.2 Hz, 2H), 4.15 (t, J=7.2 Hz, 2H), 3.78-3.75 (m, 2H), 2.28-2.23 (m, 2H), 1.43 (t, J=7.2 Hz, 3H). ESI-MS m/z 403.32 (M+H$^+$).

Example 7B

Synthesis of 4-(3-(1H-imidazol-1-yl)propylamino)-6-bromoquinoline-3-carbohydrazide (compound 16): Compound 15 (1 g, 2.48 mmol) was dissolved in ethanol (10 mL). To the solution hydrazine hydrate (10 mL) was added. The reaction mixture was stirred for 10 hours at room temperature. Ethanol was removed under vacuum. The residue was then dissolved in CHCl$_3$ and the organic layer was washed with water and brine, dried and concentrated to give compound 16 (0.75 g, 78%) as a light green solid. $^1$H NMR (300 MHz, CDCl$_3$) δ ppm 9.68 (br. s, —NH), 8.59 (d, J=1.2 Hz, 1H), 8.31 (s, 1H), 7.78 (dd, J=8.7, 1.5 Hz, 1H), 7.72 (d, J=8.7 Hz, 1H), 7.60 (s, 1H), 7.42 (t, J=5.1 Hz, —CONH), 7.16 (s, 1H), 6.88 (s, 1H), 4.52 (br. s, —NH$_2$), 4.02 (t, J=6.9 Hz, 2H), 3.32-3.26 (m, 2H), 2.10-2.01 (m, 2H). ESI-MS m/z 389.28 (M+H$^+$).

Example 7C

Synthesis of N-(3-(1H-imidazol-1-yl)propyl)-6-bromo-3-(1,3,4-oxadiazol-2-yl)quinolin-4-amine (compound 17): Compound 16 (1 g, 2.57 mmol) was taken in triethylorthoformate (5 mL, 30.06 mmol) and the mixture was heated for 12 hours at 100° C. The compound was purified by column chromatography, eluting with 3% methanol in CHCl$_3$ to afford compound 7 (0.2 g, 19%) as a yellow solid. $^1$H NMR (300 MHz, CDCl$_3$) δ ppm 9.08 (s, 1H), 8.82 (br. s, —NH), 8.53 (s, 1H), 8.33 (d, J=1.5 Hz, 1H), 7.88 (d, J=9 Hz, 1H), 7.77 (dd, J=9, 1.8 Hz, 1H), 7.47 (s, 1H), 7.06 (s, 1H), 6.92 (s, 1H), 4.23 (t, J=7.2 Hz, 2H), 3.93-3.87 (m, 2H), 2.40-2.31 (m, 2H). ESI-MS m/z 399.37 (M+H$^+$).

Example 7

Synthesis of N-(3-(1H-imidazol-1-yl)propyl)-6-(4-methoxyphenyl)-3-(1,3,4-oxadiazol-2-yl)quinolin-4-amine (compound 18): Compound 17 (0.10 g, 0.25 mmol) was dissolved in 1,4-dioxane (4 mL) and DMF (1 mL) under Ar atmosphere. Then 2-(4-methoxyphenyl)-4,4,5,5-tetramethyl-1,3,2-dioxaborolane (0.12 g, 0.5 mmol) was added to the solution. 2(M) Na$_2$CO$_3$ solution (0.3 mL) was added to the reaction mixture and Ar was purged for 5 minutes. Then Pd(PPh$_3$)$_4$(0.023 g, 0.02 mmol) was added to the reaction mixture and Ar purging was performed for about 10 minutes. Then the mixture was heated for 12 hours at 100° C. 1,4-Dioxane and DMF were removed under vacuum, the residue then dissolved in CHCl$_3$ and the organic layer was washed with water and brine, dried and concentrated. The residue was purified by silica gel column chromatography, eluting with 7% methanol in CHCl$_3$ to produce compound 18 (0.035 g, 33%) as a yellow solid. mp 202° C. $^1$H NMR (300 MHz, CDCl$_3$) δ ppm 9.15 (s, 1H), 8.97 (s, 1H), 8.53 (s, 1H), 8.50 (s, 1H), 8.30 (d, J=8.7 Hz, 1H), 7.98 (d, J=8.4 Hz, 1H), 7.70 (d, J=8.7 Hz, 2H), 7.50 (s, 1H), 7.32 (s, 1H), 7.10 (d, J=8.4 Hz, 2H), 4.43 (t, J=7.2 Hz, 2H), 4.13 (t, J=6.3 Hz, 2H), 3.89 (s, 3H), 2.53-2.45 (m, 2H). ESI-MS m/z 427.52 (M+H$^+$).

Example 8

Synthesis of N-(3-(1H-imidazol-1-yl)propyl)-6-(3,4-dimethoxyphenyl)-3-(1,3,4-oxadiazol-2-yl)quinolin-4-amine (compound 19): Compound 17 (0.10 g, 0.25 mmol) was taken along with 3,4-dimethoxyphenylboronic acid (0.091 g, 0.5 mmol) in 1,4-dioxane (4 mL) and DMF (1 mL). 2(M) Na$_2$CO$_3$ solution (0.3 mL) and Pd(PPh$_3$)$_4$(0.023 g, 0.02 mmol) were added to the mixture and the reaction was performed according to Example 7. It took 24 hours to complete the reaction. The residue was purified by silica gel column chromatography, eluting with 7% methanol in CHCl₃ to produce compound 19 (0.04 g, 35%) as an off-white solid. mp 205° C. ¹H NMR (300 MHz, CDCl₃) δ ppm 9.09 (s, 1H), 8.72 (br. s, —NH), 8.53 (s, 1H), 8.31 (s, 1H), 8.07 (d, J=8.7 Hz, 1H), 7.94 (dd, J=8.7, 1.2 Hz, 1H), 7.46 (s, 1H), 7.18-7.14 (m, 2H), 7.02 (d, J=7.8 Hz, 2H), 6.90 (s, 1H). ESI-MS m/z 457.45 (M+H⁺).

Example 9

Synthesis of N-(3-(1H-imidazol-1-yl)propyl)-6-(4-aminophenyl)-3-(1,3,4-oxadiazol-2-yl)quinolin-4-amine (compound 20): Compound 17 (0.08 g, 0.20 mmol) was taken along with 4-(4,4,5,5-tetramethyl-1,3,2-dioxaborolan-2-yl)aniline (0.088 g, 0.4 mmol) in 1,4-dioxane (4 mL) and DMF (1 mL). 2(M) Na₂CO₃ solution (0.25 mL) and Pd(PPh₃)₄ (0.018 g, 0.016 mmol) were added to the mixture and the reaction was performed according to Example 7. The residue was purified by silica gel column chromatography, eluting with 5% methanol in CHCl₃ to produce compound 20 (0.03 g, 36%) as a brown solid. mp 202° C. ¹H NMR (600 MHz, CDCl₃) δ ppm 8.97 (s, 1H), 8.67 (s, 1H), 8.11 (s, 1H), 7.81 (d, J=8.4 Hz, 1H), 7.72 (d, J=8.4 Hz, 1H), 7.61 (s, 1H), 7.34 (d, J=8.4 Hz, 2H), 7.10 (s, 1H), 6.93 (s, 1H), 6.80 (d, J=8.4 Hz, 2H), 4.17 (t, J=7.2 Hz, 2H), 3.75 (t, J=6.6 Hz, 2H), 2.25-2.21 (m, 2H). ESI-MS m/z 412.33 (M+H⁺).

Example 10

Synthesis of 4-(4-(3-(1H-imidazol-1-yl)propylamino)-3-(1,3,4-oxadiazol-2-yl)quinolin-6-yl)benzonitrile (compound 21): Compound 17 (0.08 g, 0.20 mmol) was taken along with 4-(4,4,5,5-tetramethyl-1,3,2-dioxaborolan-2-yl)benzonitrile (0.092 g, 0.40 mmol) in 1,4-dioxane (4 mL) and DMF (1 mL). 2(M) Na₂CO₃ solution (0.25 mL) and Pd(PPh₃)₄ (0.018 g, 0.016 mmol) were added to the mixture and the reaction was performed according to Example 7. The residue was purified by silica gel column chromatography, eluting with 4% methanol in CHCl₃ to produce compound 21 (0.035 g, 41%) as a bright yellow solid. mp 238° C. ¹H NMR (300 MHz, CDCl₃+1 drop CD₃OD) δ ppm 8.86 (s, 1H), 8.56 (s, 1H), 8.22 (s, 1H), 7.88 (d, J=8.7 Hz, 1H), 7.78 (dd, J=8.7, 1.5 Hz, 1H), 7.64 (d, J=8.4 Hz, 2H), 7.56 (d, J=8.1 Hz, 2H), 7.31 (s, 1H), 6.77 (d, J=4.8 Hz, 2H), 4.06 (t, J=6.9 Hz, 2H), 3.76 (m, 2H), 2.24-2.15 (m, 2H). ESI-MS m/z 421.17 (M+H⁺).

Example 11

Synthesis of 4-(4-((3-(1H-imidazol-1-yl)propyl)amino)-3-(1,3,4-oxadiazol-2-yl)quinolin-6-yl)phenol (compound 22): Compound 17 (0.10 g, 0.25 mmol) was taken along with 4-(4,4,5,5-tetramethyl-1,3,2-dioxaborolan-2-yl)phenol (0.11 g, 0.5 mmol) in 1,4-dioxane (4 mL) and DMF (1 mL). 2(M) Na₂CO₃ solution (0.3 mL) and Pd(PPh₃)₄(0.023 g, 0.02 mmol) were added to the mixture and the reaction was performed according to Example 7. It took 7 hours to complete the reaction. The residue was purified by silica gel column chromatography, eluting with 10% methanol in CHCl₃ to produce compound 22 (0.04 g, 39%) as a pale yellow solid. ¹H NMR (300 MHz, CD₃OD) δ ppm 9.09 (s, 1H), 8.93 (s, 1H), 8.44 (d, J=1.5 Hz, 1H), 8.02 (dd, J=8.7, 1.8 Hz, 1H), 7.94 (d, J=8.7 Hz, 1H), 7.65 (s, 1H), 7.57 (d, J=8.7 Hz, 2H), 7.15 (s, 1H), 6.97 (s, 1H), 6.94 (s, 2H), 4.27 (t, J=6.9 Hz, 2H), 3.98 (t, J=6.6 Hz, 2H), 2.42-2.33 (m, 2H). ESI-MS m/z 413.31 (M+H⁺).

Example 12

Synthesis of N-(3-(1H-imidazol-1-yl)propyl)-6-(4-fluorophenyl)-3-(1,3,4-oxadiazol-2-yl)quinolin-4-amine (compound 23): Compound 17 (0.08 g, 0.20 mmol) was taken along with 4-fluorophenylboronic acid (0.056 g, 0.40 mmol) in 1,4-dioxane (4 mL) and DMF (1 mL). 2(M) Na₂CO₃ solution (0.25 mL) and Pd(PPh₃)₄(0.018 g, 0.016 mmol) were added to the mixture and the reaction was performed according to Example 7. It took 8 hours to complete the reaction. The residue was purified by silica gel column chromatography, eluting with 4% methanol in CHCl₃ to produce compound 23 (0.025 g, 30%) as a pale yellow solid. ¹H NMR (600 MHz, CDCl₃) δ ppm 9.09 (s, 1H), 8.80 (t, J=4.8 Hz, —NH), 8.53 (s, 1H), 8.29 (d, J=1.8 Hz, 1H), 8.07 (d, J=9 Hz, 1H), 7.90 (dd, J=9, 1.8 Hz, 1H), 7.58-7.55 (m, 2H), 7.46 (s, 1H), 7.20 (t, J=9 Hz, 2H), 7.03 (s, 1H), 6.89 (s, 1H), 4.22 (t, J=6.6 Hz, 2H), 3.98-3.96 (m, 2H), 2.37-2.33 (m, 2H). ESI-MS m/z 415.16 (M+H⁺).

Example 13

Synthesis of N-(3-(1H-imidazol-1-yl)propyl)-6-(6-aminopyridin-3-yl)-3-(1,3,4-oxadiazol-2-yl)quinolin-4-amine (compound 24): Compound 17 (0.08 g, 0.20 mmol) was taken along with 5-(4,4,5,5-tetramethyl-1,3,2-dioxaborolan-2-yl)pyridin-2-amine (0.088 g, 0.40 mmol) in 1,4-dioxane (4 mL) and DMF (1 mL). 2(M) Na₂CO₃ solution (0.25 mL) and Pd(PPh₃)₄(0.018 g, 0.016 mmol) were added to the mixture and the reaction was performed according to Example 7. The residue was purified by silica gel column chromatography, eluting with 10% methanol in CHCl₃ to produce compound 24 (0.025 g, 30%) as a yellow solid. ¹H NMR (300 MHz, CD₃OD) δ ppm 9.04 (s, 1H), 8.84 (s, 1H), 8.31 (s, 1H), 8.24 (d, J=2.1 Hz, 1H), 7.92-7.90 (m, 2H), 7.79 (dd, J=9, 2.4 Hz, 1H), 7.62 (s, 1H), 7.11 (s, 1H), 6.91 (s, 1H), 6.71 (d, J=8.7 Hz, 1H), 4.22 (t, J=7.2 Hz, 2H), 3.90 (t, J=6.6 Hz, 2H), 2.36-2.69 (m, 2H). ESI-MS m/z 413.38 (M+H⁺).

Example 14

Synthesis of N-(3-(1H-imidazol-1-yl)propyl)-6-(2,6-difluoro-4-methoxyphenyl)-3-(1,3,4-oxadiazol-2-yl)quinolin-4-amine (compound 25): Compound 17 (0.08 g, 0.20 mmol) was taken along with 2,6-difluoro-4-methoxyphenylboronic acid (0.094 g, 0.50 mmol) in 1,4-dioxane (4 mL) and DMF (1 mL). 2(M) Na₂CO₃ solution (0.25 mL) and Pd(PPh₃)₄ (0.018 g, 0.016 mmol) were added to the mixture and the reaction was performed according to Example 7. The residue was purified by silica gel column chromatography, eluting with 4% methanol in CHCl₃ to produce compound 25 (0.023 g, 25%) as a yellow solid. ¹H NMR (600 MHz, CDCl₃) δ ppm 9.14 (s, 1H), 8.88 (br. s, —NH), 8.55 (s, 1H), 8.33 (s, 1H), 8.10 (d, J=8.4 Hz, 1H), 7.84 (d, J=8.4 Hz, 1H), 7.54 (s, 1H), 7.07 (s, 1H), 6.96 (s, 1H), 6.66 (s, 1H), 6.65 (s, 1H), 4.23 (t, J=7.2 Hz, 2H), 3.99-3.96 (m, 2H), 3.90 (s, 3H), 2.39-2.35 (m, 2H). ESI-MS m/z 463.44 (M+H⁺).

Example 15

Synthesis of N-(3-(1H-imidazol-1-yl)propyl)-3-(1,3,4-oxadiazol-2-yl)-6-phenylquinolin-4-amine (compound 26): Compound 17 (0.08 g, 0.20 mmol) was taken along with phenylboronic acid (0.049 g, 0.40 mmol) in 1,4-dioxane (4 mL) and DMF (1 mL). 2(M) Na₂CO₃ solution (0.25 mL) and Pd(PPh₃)₄(0.018 g, 0.016 mmol) were added to the mixture and the reaction was performed according to Example 7. The residue was purified by silica gel column chromatography, eluting with 4% methanol in CHCl₃ to produce compound 26 (0.032 g, 40%) as a white solid. ¹H NMR (300 MHz, CDCl₃) δ ppm 9.11 (s, 1H), 8.82 (br. s, —NH), 8.53 (s, 1H), 8.38 (s, 1H), 8.09 (d, J=9 Hz, 1H), 7.98 (d, J=8.4 Hz, 1H), 7.63 (d, J=7.5 Hz, 2H), 7.53 (t, J=7.5 Hz, 2H), 7.46-7.41 (m, 2H), 7.04 (s, 1H), 6.91 (s, 1H), 4.22 (t, J=6.9 Hz, 2H), 4.03-3.98 (m, 2H), 2.41-2.32 (m, 2H). ESI-MS m/z 397.43 (M+H$^+$).

Example 16

Synthesis of N-(3-(1H-imidazol-1-yl)propyl)-6-(2,4-dimethoxyphenyl)-3-(1,3,4-oxadiazol-2-yl)quinolin-4-amine (compound 27): Compound 17 (0.07 g, 0.18 mmol) was taken along with 2,4-dimethoxyphenylboronic acid (0.064 g, 0.36 mmol) in 1,4-dioxane (4 mL) and DMF (1 mL). 2(M) Na$_2$CO$_3$ solution (0.23 mL) and Pd(PPh$_3$)$_4$(0.017 g, 0.014 mmol) were added to the mixture and the reaction was performed according to Example 7. The crude product was purified by silica gel column chromatography, eluting with 7% methanol in CHCl$_3$ to afford compound 27 (0.035 g, 44%) as a yellow solid. $^1$H NMR (300 MHz, CDCl$_3$) δ ppm 9.07 (s, 1H), 8.80 (br. s, —NH), 8.52 (s, 1H), 8.37 (d, J=1.2 Hz, 1H), 8.02 (d, J=8.4 Hz, 1H), 7.88 (dd, J=9, 1.8 Hz, 1H), 7.47 (s, 1H), 7.30 (d, J=8.4 Hz, 1H), 7.03 (s, 1H), 6.90 (s, 1H), 6.66-6.61 (m, 2H), 4.21 (t, J=6.9 Hz, 2H), 4.00-3.93 (m, 2H), 3.89 (s, 3H), 3.80 (s, 3H), 2.37-2.28 (m, 2H). ESI-MS m/z 457.51 (M+H$^+$).

Example 17

Synthesis of N-(3-(1H-imidazol-1-yl)propyl)-6-(4-methoxy-3-methylphenyl)-3-(1,3,4-oxadiazol-2-yl)quinolin-4-amine (compound 28): Compound 17 (0.07 g, 0.18 mmol) was taken along with 4-methoxy-3-methylphenylboronic acid (0.058 g, 0.36 mmol) in 1,4-dioxane (4 mL) and DMF (1 mL). 2(M) Na$_2$CO$_3$ solution (0.23 mL) and Pd(PPh$_3$)$_4$(0.017 g, 0.014 mmol) were added to the mixture and the reaction was performed according to Example 7. The residue was purified by silica gel column chromatography, eluting with 7% methanol in CHCl$_3$ to produce compound 28 (0.031 g, 40%) as a pale yellow solid. H NMR (300 MHz, CDCl$_3$) δ ppm 9.07 (s, 1H), 8.75 (br. s, —NH), 8.52 (s, 1H), 8.29 (s, 1H), 8.04 (d, J=8.7 Hz, 1H), 7.93 (dd, J=8.7, 1.2 Hz, 1H), 7.46 (s, 1H), 7.43-7.41 (m, 2H), 7.03 (s, 1H), 6.96 (d, J=9.3 Hz, 1H), 6.90 (s, 1H), 4.21 (t, J=6.9 Hz, 2H), 4.02-3.96 (m, 2H), 3.90 (s, 3H), 2.39-2.34 (m, 2H), 2.33 (s, 3H). ESI-MS m/z 441.41 (M+H$^+$).

Example 18

Synthesis of N-(3-(1H-imidazol-1-yl)propyl)-3-(1,3,4-oxadiazol-2-yl)-6-p-tolylquinolin-4-amine (compound 29): Compound 17 (0.07 g, 0.18 mmol) was taken along with p-tolylboronic acid (0.037 g, 0.27 mmol) in 1,4-dioxane (4 mL) and DMF (1 mL). 2(M) Na$_2$CO$_3$ solution (0.23 mL) and Pd(PPh$_3$)$_4$(0.017 g, 0.014 mmol) were added to the mixture and the reaction was performed according to Example 7. It took 8 hours to complete the reaction. The residue was purified by silica gel column chromatography, eluting with 6% methanol in CHCl$_3$ to produce compound 29 (0.037 g, 51%) as a yellow solid. $^1$H NMR (600 MHz, CDCl$_3$) δ ppm 9.07 (s, 1H), 8.77 (t, J=4.2 Hz, —NH), 8.51 (s, 1H), 8.33 (d, J=1.8 Hz, 1H), 8.05 (d, J=9 Hz, 1H), 7.94 (dd, J=9, 1.8 Hz, 1H), 7.51 (d, J=7.8 Hz, 2H), 7.46 (s, 1H), 7.32 (d, J=7.8 Hz, 2H), 7.04 (s, 1H), 6.90 (s, 1H), 4.21 (t, J=7.2 Hz, 2H), 3.99-3.96 (m, 2H), 2.43 (s, 3H), 2.36-2.32 (m, 2H). ESI-MS m/z 411.65 (M+H$^+$).

Example 19

Synthesis of N-(3-(1H-imidazol-1-yl)propyl)-3-(1,3,4-oxadiazol-2-yl)-6-(pyridin-3-yl)quinolin-4-amine (compound 30): Compound 17 (0.07 g, 0.18 mmol) was taken along with pyridin-3-ylboronic acid (0.043 g, 0.36 mmol) in 1,4-dioxane (4 mL) and DMF (1 mL). 2(M) Na$_2$CO$_3$ solution (0.23 mL) and Pd(PPh$_3$)$_4$(0.017 g, 0.014 mmol) were added to the mixture and the reaction was performed according to Example 7. It took 24 hours to complete the reaction. The residue was purified by silica gel column chromatography, eluting with 4% methanol in CHCl$_3$ to produce compound 30 (0.025 g, 36%) as a yellow solid. $^1$H NMR (600 MHz, CDCl$_3$) δ ppm 9.12 (s, 1H), 8.90 (br. s, 1H), 8.85 (br. s, —NH), 8.66 (d, J=4.2 Hz, 1H), 8.54 (s, 1H), 8.36 (d, J=1.8 Hz, 1H), 8.12 (d, J=8.4 Hz, 1H), 7.93-7.90 (m, 2H), 7.46-7.44 (m, 2H), 7.02 (s, 1H), 6.90 (s, 1H), 4.23 (t, J=7.2 Hz, 2H), 3.99-3.96 (m, 2H), 2.39-2.34 (m, 2H). ESI-MS m/z 398.66 (M+H$^+$).

Example 20

Synthesis of N-(3-(1H-imidazol-1-yl)propyl)-6-(4-methoxy-2-methylphenyl)-3-(1,3,4-oxadiazol-2-yl)quinolin-4-amine (compound 31): Compound 17 (0.08 g, 0.20 mmol) was taken along with 4-methoxy-2-methylphenylboronic acid (0.067 g, 0.40 mmol) in 1,4-dioxane (4 mL) and DMF (1 mL). 2(M) Na$_2$CO$_3$ solution (0.30 mL) and Pd(PPh$_3$)$_4$(0.018 g, 0.016 mmol) were added to the mixture and the reaction was performed according to Example 7. It took 7 hours to complete the reaction. The residue was purified by silica gel column chromatography, eluting with 6% methanol in CHCl$_3$ to produce compound 31 (0.040 g, 45%) as a yellow gummy liquid. $^1$H NMR (600 MHz, CDCl$_3$) δ ppm 9.07 (s, 1H), 8.76 (br. s, —NH), 8.52 (d, J=1.8 Hz, 1H), 8.06 (s, 1H), 8.00 (d, J=7.2 Hz, 1H), 7.66 (d, J=8.4 Hz, 1H), 7.41 (s, 1H), 7.17 (d, J=6.6 Hz, 1H), 6.98 (s, 1H), 6.84-6.83 (m, 3H), 4.16 (t, J=4.8 Hz, 2H), 3.88-3.87 (m, 2H), 3.84 (s, 3H), 2.28 (m, 2H), 2.26 (s, 3H). ESI-MS m/z 441.15 (M+H$^+$).

Example 21

Synthesis of N-(3-(1H-imidazol-1-yl)propyl)-6-(4-methoxy-2,6-dimethylphenyl)-3-(1,3,4-oxadiazol-2-yl)quinolin-4-amine (compound 32): Compound 17 (0.1 g, 0.25 mmol) and 4-methoxy-2,6-dimethylphenylboronic acid (0.067 g, 0.37 mmol) were dissolved in 1,4-dioxane (5 mL). 2(M) Na$_2$CO$_3$ solution (0.3 mL) and Pd(PPh$_3$)$_4$(0.023 g, 0.02 mmol) were added to the mixture and the reaction was performed according to Example 7. It took 12 hours to complete the reaction. The crude product was purified by silica gel column chromatography, eluting with 4% methanol in CHCl$_3$ to afford compound 32 (0.037 g, 32%) as a pale yellow solid. $^1$H NMR (300 MHz, CDCl$_3$) δ ppm 9.11 (s, 1H), 8.78 (t, J=3.9 Hz, —NH), 8.53 (s, 1H), 8.06 (d, J=8.7 Hz, 1H), 7.94 (d, J=0.9 Hz, 1H), 7.51 (dd, J=8.4, 1.5 Hz, 1H), 7.38 (s, 1H), 6.98 (s, 1H), 6.81 (s, 1H), 6.72 (s, 2H), 4.16 (t, J=6.9 Hz, 2H), 3.86-3.81 (m, 5H), 2.33-2.24 (m, 2H), 2.02 (s, 6H). ESI-MS m/z 455.22 (M+H$^+$).

Example 22

Synthesis of N-(3-(1H-imidazol-1-yl)propyl)-6-(6-methoxypyridin-3-yl)-3-(1,3,4-oxadiazol-2-yl)quinolin-4-amine (compound 33): Compound 17 (0.1 g, 0.25 mmol) was taken along with 2-methoxy-5-(4,4,5,5-tetramethyl-1,3,2-dioxaborolan-2-yl)pyridine (0.118 g, 0.5 mmol) in 1,4-dioxane (4 mL) and DMF (1 mL). 2(M) Na$_2$CO$_3$ solution (0.3 mL) and Pd(PPh$_3$)$_4$(0.023 g, 0.02 mmol) were added to the mixture and the reaction was performed according to Example 7. The reaction mixture was heated at 120° C. for 24 hours. The residue was purified by silica gel column chromatography, eluting with 8% methanol in CHCl₃ to produce compound 33 (0.031 g, 29%) as a white solid. ¹H NMR (300 MHz, CDCl₃) δ ppm 9.11 (s, 1H), 8.85 (t, J=3.9 Hz, —NH), 8.54 (s, 1H), 8.44 (d, J=2.1 Hz, 1H), 8.31 (d, J=1.5 Hz, 1H), 8.11 (d, J=8.7 Hz, 1H), 7.89 (dd, J=9, 2.1 Hz, 1H), 7.83 (dd, J=9, 2.4 Hz, 1H), 7.49 (s, 1H), 7.05 (s, 1H), 6.91-6.89 (m, 2H), 4.24 (t, J=6.9 Hz, 2H), 4.01 (s, 3H), 3.99-3.95 (m, 2H), 2.41-2.32 (m, 2H). ESI-MS m/z 428.14 (M+H⁺).

Example 23

Synthesis of N-(3-(1H-imidazol-1-yl)propyl)-6-(4-ethoxyphenyl)-3-(1,3,4-oxadiazol-2-yl)quinolin-4-amine (compound 34): Compound 17 (0.08 g, 0.2 mmol) was taken along with (4-ethoxyphenyl)boronic acid (0.066 g, 0.4 mmol) in 1,4-dioxane (4 mL) and DMF (1 mL). 2(M) Na₂CO₃ solution (0.25 mL) and Pd(PPh₃)₄(0.023 g, 0.02 mmol) were added to the mixture and the reaction was performed according to Example 7. It took 12 hours to complete the reaction. The residue was purified by silica gel column chromatography, eluting with 4% methanol in CHCl₃ to produce compound 34 (0.035 g, 40%) as a yellow solid. ¹H NMR (600 MHz, CDCl₃) δ ppm 9.08 (s, 1H), 8.80 (br. s, —NH), 8.52 (s, 1H), 8.31 (d, J=1.8 Hz, 1H), 8.07 (d, J=9.0 Hz, 1H), 7.94 (dd, J=8.4, 1.8 Hz, 1H), 7.55 (d, J=8.4 Hz, 2H), 7.49 (s, 1H), 7.05-7.03 (m, 3H), 6.92 (s, 1H), 4.22 (t, J=7.2 Hz, 2H), 4.12 (q, J=7.2 Hz, 2H), 4.01-3.98 (m, 2H), 2.38-2.34 (m, 2H), 1.47 (t, J=7.2 Hz, 3H). ESI-MS m/z 441.21 (M+H⁺).

Example 24

Synthesis of N-(3-(1H-imidazol-1-yl)propyl)-6-(4-ethylphenyl)-3-(1,3,4-oxadiazol-2-yl)quinolin-4-amine(compound 35): Compound 17 (0.08 g, 0.20 mmol) was taken along with 4-ethylphenylboronic acid (0.04 g, 0.24 mmol) in 1,4-dioxane (2 mL) and DMF (0.5 mL). 2(M) Na₂CO₃ solution (0.1 mL) and Pd(PPh₃)₄(0.023 g, 0.01 mmol) were added to the mixture and the reaction was performed according to Example 7. It took 12 hours to complete the reaction. The residue was purified by silica gel column chromatography, eluting with 5% methanol in CHCl₃ to produce compound 35 (0.035 g, 33%) as a yellow solid. ¹H NMR (CDCl₃+1 drop CD₃OD, 400 MHz) δ ppm 9.06 (s, 1H), 8.78 (1H, t, J=4 Hz), 8.50 (s, 1H), 8.33 (d, J=1.2 Hz, 1H), 8.05 (d, J=8.8 Hz, 1H), 7.94 (dd, J=8.8, 1.6 Hz, 1H), 7.53 (s, 1H), 7.52 (s, 1H), 7.46 (s, 1H), 7.34 (s, 1H), 7.32 (s, 1H), 7.01 (s, 1H), 6.89 (s, 1H), 4.19 (t, J=6.8 Hz, 2H), 4.00-3.96 (m, 2H), 2.72 (q, J=7.6 Hz, 2H), 2.37-2.30 (m, 2H), 1.29 (t, J=7.6 Hz, 3H). ESI-MS m/z 425.21 (M+H⁺).

Example 25

Synthesis of N-(3-(1H-imidazol-1-yl)propyl)-6-(4-isopropoxyphenyl)-3-(1,3,4-oxadiazol-2-yl)quinolin-4-amine (compound 36): Compound 17 (0.08 g, 0.20 mmol) was taken along with 4-isopropoxyphenylboronic acid (0.043 g, 0.24 mmol) in 1,4-dioxane (2 mL) and DMF (0.5 mL). 2(M) Na₂CO₃ solution (0.1 mL) and Pd(PPh₃)₄(0.023 g, 0.01 mmol) were added to the mixture and the reaction was performed according to Example 7. It took 12 hours to complete the reaction. The residue was purified by silica gel column chromatography, eluting with 5% methanol in CHCl₃ to produce compound 36 (0.04 g, 35%) as a yellow solid. ¹H NMR (CDCl₃+1 drop CD₃OD, 400 MHz) δ ppm 9.04 (s, 1H), 8.53 (s, 1H), 8.29 (d, J=1.6 Hz, 1H), 8.12 (d, J=8.8 Hz, 1H), 7.94 (dd, J=8.8 Hz, 2 Hz, 1H), 7.67 (s, 1H), 7.51 (d, J=8.4 Hz, 2H), 7.04 (s, 1H), 7.00 (d, J=8.8 Hz, 2H), 6.94 (s, 1H), 4.66-4.56 (m, 1H), 4.25 (t, J=7.2 Hz, 2H), 4.01 (t, J=7.2 Hz, 2H), 2.40-2.34 (m, 2H), 1.36 (d, J=6 Hz, 6H). ESI-MS m/z 455.22 (M+H⁺).

Example 26

Synthesis of N-(3-(1H-imidazol-1-yl)propyl)-6-(4-isopropylphenyl)-3-(1,3,4-oxadiazol-2-yl)quinolin-4-amine (compound 37): Compound 17 (0.08 g, 0.20 mmol) was taken along with 4-isopropylphenylboronic acid (0.04 g, 0.24 mmol) in 1,4-dioxane (2 mL) and DMF (0.5 mL). 2(M) Na₂CO₃ solution (0.1 mL) and Pd(PPh₃)₄(0.023 g, 0.01 mmol) were added to the mixture and the reaction was performed according to Example 7. It took 12 hours to complete the reaction. The residue was purified by silica gel column chromatography, eluting with 5% methanol in CHCl₃ to produce compound 37 (0.036 g, 34%) as a yellow solid. H NMR (CDCl₃+1 drop CD₃OD, 400 MHz) δ ppm 9.05 (s, 1H), 8.52 (1H, s), 8.34 (d, J=1.6 Hz, 1H), 8.08 (d, J=8.4 Hz, 1H), 7.95 (dd, J=8.8 Hz, 2 Hz, 1H), 7.55 (s, 1H), 7.54 (s, 1H), 7.52 (s, 1H), 7.37 (s, 1H), 7.35 (s, 1H), 7.02 (s, 1H), 6.91 (s, 1H), 4.22 (t, J=7.2 Hz, 2H), 4.02-3.97 (m, 2H), 3.01-2.94 (m, 1H), 2.38-2.31 (m, 2H), 1.30 (d, J=7.2 Hz, 6H). ESI-MS m/z 439.22 (M+H⁺).

Example 27

Synthesis of N-(3-(1H-imidazol-1-yl)propyl)-6-(6-methylpyridin-3-yl)-3-(1,3,4-oxadiazol-2-yl)quinolin-4-amine (compound 38): Compound 17 (0.08 g, 0.20 mmol) was taken along with 2-methylpyridine-5-boronic acid (0.033 g, 0.24 mmol) in 1,4-dioxane (2 mL) and DMF (0.5 mL). 2(M) Na₂CO₃ solution (0.1 mL) and Pd(PPh₃)₄(0.023 g, 0.01 mmol) were added to the mixture and the reaction was performed according to Example 7. It took 12 hours to complete the reaction. The residue was purified by silica gel column chromatography, eluting with 5% methanol in CHCl₃ to produce compound 38 (0.039 g, 39%) as a yellow solid. H NMR (CDCl₃+1 drop CD₃OD, 400 MHz) δ ppm 9.05 (s, 1H), 8.71 (s, 1H), 8.54 (s, 1H), 8.30 (s, 1H), 8.07 (d, J=10 Hz, 1H), 7.84 (d, J=8.4 Hz, 1H), 7.79 (d, J=8 Hz, 1H), 7.52 (s, 1H), 7.29 (d, J=8 Hz, 1H), 6.98 (s, 1H), 6.89 (s, 1H), 4.21 (t, J=6.8 Hz, 2H), 3.96 (t, J=6.4 Hz, 2H), 2.61 (s, 3H), 2.33 (m, 2H). ESI-MS m/z 412.19 (M+H⁺).

Example 28

5-(4-((3-(1H-imidazol-1-yl)propyl)amino)-3-(1,3,4-oxadiazol-2-yl)quinolin-6-yl)pyridin-2-ol (compound 39): Compound 17 (0.08 g, 0.2 mmol) was taken along with (4-ethoxyphenyl)boronic acid (0.066 g, 0.4 mmol) in 1,4-dioxane (4 mL) and DMF (1 mL). 2(M) Na₂CO₃ solution (0.25 mL) and Pd(PPh₃)₄(0.023 g, 0.02 mmol) were added to the mixture and the reaction was performed according to Example 7. It took 12 hours to complete the reaction. The residue was purified by silica gel column chromatography, eluting with 70% CMA [a mixture of chloroform (80%), methanol (15%) and ammonia (5%)] solution to afford compound 39 (0.03 g, 36%) as a light yellow solid. ¹H NMR (600 MHz, CDCl₃+1 drop CD₃OD) δ ppm 8.97 (s, 1H), 8.59 (s, 1H), 8.09 (s, 1H), 7.97 (d, J=8.4 Hz, 1H), 7.74-7.71 (m, 2H), 7.49 (s, 1H), 7.45 (d, J=2.4 Hz, 1H), 6.97 (s, 1H), 6.90

(s, 1H), 6.67 (d, J=9.6 Hz, 1H), 4.20 (t, J=6.6 Hz, 2H), 3.85 (t, J=6.6 Hz, 2H), 2.34-2.30 (m, 2H). ESI-MS m/z 414.17 (M+H$^+$).

Example 29A

Synthesis of ethyl 6-bromo-4-(3-morpholinopropylamino)quinoline-3-carboxylate (compound 40): Compound 4 (1 g, 3.18 mmol) was dissolved in 1,4-dioxane (5 mL) under N$_2$ atmosphere. To the reaction mixture dry DIPEA (1.11 mL, 6.36 mmol) and 3-morpholinopropan-1-amine (0.63 mL, 4.77 mmol) were added respectively. The reaction mixture was allowed to stir for 24 hours at room temperature. Then it was poured into 50 mL water. The solid obtained was filtered and dried to give compound 40 (1.2 g, 90%) as a white solid. $^1$H NMR (300 MHz, CDCl$_3$) δ ppm 9.23 (br. s, —NH), 9.06 (s, 1H), 8.36 (d, J=2.1 Hz, 1H), 7.81 (d, J=9 Hz, 1H), 7.72 (dd, J=9, 2.1 Hz, 1H), 4.38 (q, J=7.2 Hz, 2H), 3.87-3.81 (m, 2H), 3.69 (t, J=4.5 Hz, 4H), 2.50 (t, J=7.2 Hz, 2H), 2.44 (t, J=4.5 Hz, 4H), 1.99-1.90 (m, 2H), 1.42 (t, J=7.2 Hz, 3H). ESI-MS m/z 422.30 (M+H$^+$).

Example 29B

Synthesis of 6-bromo-4-(3-morpholinopropylamino)quinoline-3-carbohydrazide (compound 41): Compound 40 (1 g, 2.37 mmol) was dissolved in ethanol (10 mL). To the solution hydrazine hydrate (10 mL) was added. The reaction mixture was stirred for 12 hours at room temperature. Ethanol was removed under vacuum. The residue was then dissolved in CHCl$_3$ and the organic layer was washed with water and brine, dried and concentrated to give compound 41 (0.85 g, 88%) as a pale yellow solid. $^1$H NMR (300 MHz, CDCl$_3$) δ ppm 8.48 (d, J=2.1 Hz, 1H), 8.40 (s, 1H), 7.82 (dd, J=8.7 Hz, 1H), 7.74 (d, J=9 Hz, 1H), 3.76 (t, J=4.5 Hz, 4H), 3.71 (t, J=4.8 Hz, 2H), 2.52-2.50 (m, 4H), 1.96-1.87 (m, 2H). ESI-MS m/z 408.20 (M+H$^+$).

Example 29C

Synthesis of 6-bromo-N-(3-morpholinopropyl)-3-(1,3,4-oxadiazol-2-yl)quinolin-4-amine (compound 42): Compound 41(1 g, 2.45 mmol) was taken in triethylorthoformate (5 mL, 30.06 mmol) and the mixture was heated for 12 hours at 110° C. The compound was purified by column chromatography, eluting with 4% methanol in CHCl$_3$ to give compound 42 (0.25 g, 25%) as a yellow solid. $^1$H NMR (300 MHz, CDCl$_3$) δ ppm 9.03 (s, 1H), 8.82 (br. s, —NH), 8.49 (s, 1H), 8.46 (d, J=0.9 Hz, 1H), 7.86 (d, J=8.7 Hz, 1H), 7.76 (dd, J=9, 1.8 Hz, 1H), 3.99-3.93 (m, 2H), 3.70 (t, J=4.5 Hz, 4H), 2.54 (t, J=6.9 Hz, 2H), 2.45 (t, J=3.9 Hz, 4H), 2.08-1.99 (m, 2H). ESI-MS m/z 418.25 (M+H$^+$).

Example 29

Synthesis of 6-(4-methoxyphenyl)-N-(3-morpholinopropyl)-3-(1,3,4-oxadiazol-2-yl)quinolin-4-amine (compound 43): Compound 42 (0.10 g, 0.24 mmol) was taken along with 2-(4-methoxyphenyl)-4,4,5,5-tetramethyl-1,3,2-dioxaborolane (0.11 g, 0.48 mmol) in 1,4-dioxane (5 mL). 2(M) Na$_2$CO$_3$ solution (0.3 mL) and Pd(PPh$_3$)$_4$(0.022 g, 0.019 mmol) were added to the mixture and the reaction was performed according to Example 1. The residue was purified by silica gel column chromatography to produce compound 43 (0.037 g, 35%) as a grey solid. $^1$H NMR (600 MHz, CDCl$_3$) δ ppm 9.06 (s, 1H), 8.86 (br. s, —NH), 8.51 (s, 1H), 8.47 (d, J=1.2 Hz, 1H), 8.08 (d, J=9 Hz, 1H), 7.96 (dd, J=9, 1.8 Hz, 1H), 7.64 (d, J=9 Hz, 2H), 7.07 (d, J=8.4 Hz, 2H), 4.13-4.10 (m, 2H), 3.91 (s, 3H), 3.69 (t, J=4.2 Hz, 4H), 2.57 (t, J=7.2 Hz, 2H), 2.47 (s, 4H), 2.12-2.07 (m, 2H). ESI-MS m/z 446.39 (M+H$^+$).

Example 30

Synthesis of 6-(6-methoxypyridin-3-yl)-N-(3-morpholinopropyl)-3-(1,3,4-oxadiazol-2-yl)quinolin-4-amine (compound 44): Compound 42 (0.10 g, 0.24 mmol) was taken along with 2-methoxy-5-(4,4,5,5-tetramethyl-1,3,2-dioxaborolan-2-yl)pyridine (0.085 g, 0.36 mmol) in a mixture of 1,4-dioxane (4 mL) and DMF (1 mL). 2(M) Na$_2$CO$_3$ solution (0.3 mL) and Pd(PPh$_3$)$_4$(0.022 g, 0.019 mmol) were added to the mixture and the reaction was performed according to Example 1. The crude product was purified by silica gel column chromatography to afford compound 44 (0.03 g, 28%) as a white solid. $^1$H NMR (600 MHz, CDCl$_3$) δ ppm 9.06 (s, 1H), 8.50-8.49 (m, 2H), 8.45 (d, J=1.8 Hz, 1H), 8.07 (d, J=9 Hz, 1H), 7.90 (d, J=1.8 Hz, 1H), 7.88 (d, J=2.4 Hz, 1H), 6.90 (d, J=8.4 Hz, 1H), 4.10-4.07 (m, 2H), 4.02 (s, 3H), 3.69 (t, J=4.8 Hz, 2H), 3.66 (t, J=4.8 Hz, 4H), 2.54 (t, J=7.2 Hz, 4H), 2.07-2.04 (m, 2H). ESI-MS m/z 447.21 (M+H$^+$).

Example 31

Synthesis of N-(3-morpholinopropyl)-3-(1,3,4-oxadiazol-2-yl)-6-(p-tolyl)-quinolin-4-amine (compound 44a): Compound 42 (0.10 g, 0.24 mmol) was taken along with p-tolylboronic acid (0.049 g, 0.36 mmol) in 1,4-dioxane (5 mL). 2(M) Na$_2$CO$_3$ solution (0.3 mL) and Pd(PPh$_3$)$_4$(0.023 g, 0.02 mmol) were added to the mixture, and the reaction was performed according to Example 1. The reaction took 8 hours to complete. The residue was purified by silica gel column chromatography to produce compound 44a as a white solid (0.039 g, 38%). mp 168° C. $^1$H NMR (300 MHz, CDCl$_3$) δ ppm 9.04 (s, 1H), 8.82 (br. s, —NH), 8.48 (s, 2H), 8.05 (d, J=8.7 Hz, 1H), 7.95 (d, J=8.4 Hz, 1H), 7.58 (d, J=7.8 Hz, 2H), 7.32 (d, J=7.5 Hz, 2H), 4.11-4.05 (m, 2H), 3.64 (t, J=4.5 Hz, 4H), 2.52 (t, J=7.2 Hz, 2H), 2.44-2.42 (m, 7H), 2.09-2.01 (m, 2H). ESI-MS m/z 430.41 (M+H$^+$).

Example 32

Synthesis of 6-(6-aminopyridin-3-yl)-N-(3-morpholinopropyl)-3-(1,3,4-oxadiazol-2-yl)quinolin-4-amine (compound 45): Compound 42 (0.10 g, 0.24 mmol) was taken along with 5-(4,4,5,5-tetramethyl-1,3,2-dioxaborolan-2-yl) pyridin-2-amine (0.11 g, 0.48 mmol) in 1,4-dioxane (4 mL) and DMF (1 mL). 2(M) Na$_2$CO$_3$ solution (0.3 mL) and Pd(PPh$_3$)$_4$(0.022 g, 0.019 mmol) were added to the mixture and the reaction was performed according to Example 1. It took 6 hours to complete the reaction. The residue was purified by silica gel column chromatography to produce compound 45 (0.031 g, 30%) as a light brown solid. $^1$H NMR (600 MHz, CDCl$_3$) δ ppm 9.04 (s, 1H), 8.83 (t, J=4.2 Hz, —NH), 8.49 (s, 1H), 8.42 (d, J=2.4 Hz, 1H), 8.41 (d, J=1.2 Hz, 1H), 8.05 (d, J=9 Hz, 1H), 7.86 (dd, J=9, 1.8 Hz, 1H), 7.76 (dd, J=8.4, 2.4 Hz, 1H), 6.65 (d, J=8.4 Hz, 1H), 4.61 (br. s, —NH$_2$), 4.09-4.06 (m, 2H), 3.66 (t, J=4.2 Hz, 4H), 2.53 (t, J=7.2 Hz, 2H), 2.43 (s, 4H), 2.05 (m, 2H). ESI-MS m/z 432.11 (M+H$^+$).

Example 33

Synthesis of 6-(3,4-dimethoxyphenyl)-N-(3-morpholinopropyl)-3-(1,3,4-oxadiazol-2-yl)quinolin-4-amine (compound 45a): Compound 42 (0.10 g, 0.24 mmol) was taken along with 3,4 dimethoxyphenylboronic acid (0.087 g, 0.48 mmol) in a mixture of 1,4-dioxane (4 mL) and DMF (1 mL). 2(M) $Na_2CO_3$ solution (0.3 mL) and $Pd(PPh_3)_4$(0.022 g, 0.02 mmol) were added to the mixture, and the reaction was performed according to Example 1. The residue was purified by silica gel column chromatography to afford compound 45a as a white solid (0.033 g, 30% yield). mp 182° C. $^1H$ NMR (300 MHz, $CD_3OD$) δ ppm 9.08 (s, 1H), 8.93 (s, 1H), 8.58 (s, 1H), 8.08 (dd, J=9.0, 1.5 Hz, 1H), 7.97 (d, J=8.7 Hz, 1H), 7.35-7.34 (m, 2H), 7.12 (d, J=9.3 Hz, 1H), 4.09 (t, J=6.9 Hz, 2H), 3.97 (s, 3H), 3.92 (s, 3H), 3.64 (t, J=4.8 Hz, 4H), 2.60 (t, J=6.9 Hz, 2H), 2.49 (t, J=3.9 Hz, 4H), 2.11-2.07 (m, 2H). ESI-MS m/z 476.37 $(M+H^+)$.

Example 34A

Synthesis of ethyl 4-(2-(1H-imidazol-1-yl)ethylamino)-6-bromoquinoline-3-carboxylate (compound 46): Compound 4 (0.5 g, 1.59 mmol) was dissolved in 1,4-dioxane (2.5 mL) and DMF (1 mL) under $N_2$ atmosphere. To the reaction mixture dry DIPEA (0.55 mL, 3.18 mmol) and 2-(1H-imidazol-1-yl)ethanamine (0.27 g, 2.39 mmol) were added respectively. The reaction mixture was heated for 12 hours at 100° C. Then 1,4-Dioxane and DMF were removed under vacuum, the residue then dissolved in $CHCl_3$/MeOH mixture and the organic layer was washed with water and brine, dried and concentrated. The residue was purified by silica gel column chromatography, eluting with 4% methanol in $CHCl_3$ to produce compound 46 (0.35 g, 57%) as a yellow solid. $^1H$ NMR (300 MHz, $CDCl_3$) δ ppm 9.15 (t, J=4.8 Hz, —NH), 9.09 (s, 1H), 8.14 (d, J=1.8 Hz, 1H), 7.85 (d, J=8.7 Hz, 1H), 7.75 (dd, J=9, 2.1 Hz, 1H), 7.57 (s, 1H), 7.07 (s, 1H), 6.98 (s, 1H), 4.40 (q, J=6.9 Hz, 2H), 4.30 (t, J=6 Hz, 2H), 4.17-4.11 (m, 2H), 1.43 (t, J=6.9 Hz, 3H). ESI-MS m/z 389.29 $(M+H^+)$.

Example 34B

Synthesis of 4-(2-(1H-pyrrol-1-yl)ethylamino)-6-bromo-quinoline-3-carbohydrazide (compound 47): Compound 46 (1 g, 2.58 mmol) was dissolved in ethanol (10 mL). To the solution hydrazine hydrate (10 mL) was added. The reaction mixture was stirred for 10 hours at room temperature. Ethanol was removed under vacuum. The residue was then dissolved in $CHCl_3$ and the organic layer was washed with water and brine, dried and concentrated to give compound 47 (0.82 g, 85%) as a yellow solid. $^1H$ NMR (600 MHz, $CD_3OD$) δ ppm 8.40 (s, 1H), 8.31 (d, J=1.8 Hz, 1H), 7.78 (dd, J=9.0, 1.8 Hz, 1H), 7.71 (d, J=8.4 Hz, 1H), 7.59 (s, 1H), 7.09 (s, 1H), 6.91 (s, 1H), 4.31 (t, J=6.0 Hz, 2H), 3.83 (t, J=6.0 Hz, 2H), 1.81 (s, —$CONHNH_2$, 2H). ESI-MS m/z 375.05 $(M+H^+)$.

Example 34C

Synthesis of N-(2-(1H-imidazol-1-yl)ethyl)-6-bromo-3-(1,3,4-oxadiazol-2-yl)quinolin-4-amine (compound 48): Compound 47 (1 g, 2.67 mmol) was taken in triethylorthoformate (5 mL, 30.06 mmol) and the mixture was heated for 12 hours at 100° C. The compound was purified by column chromatography, eluting with 4% methanol in $CHCl_3$ to give compound 48 (0.22 g, 43%) as a yellow solid. $^1H$ NMR (300 MHz, $CDCl_3$) δ ppm 9.05 (s, 1H), 8.68 (br. s, —NH), 8.52 (s, 1H), 8.22 (d, J=1.5 Hz, 1H), 7.90 (d, J=8.7 Hz, 1H), 7.79 (dd, J=9.3, 2.1 Hz, 1H), 7.49 (s, 1H), 6.99 (s, 1H), 6.94 (s, 1H), 4.37 (t, J=5.7 Hz, 2H), 4.29-4.23 (m, 2H).
ESI-MS m/z 385.27 $(M+H^+)$.

Example 34

Synthesis of N-(2-(1H-imidazol-1-yl)ethyl)-6-(4-methoxyphenyl)-3-(5-(4-methoxyphenyl)-1,3,4-oxadiazol-2-yl)quinolin-4-amine (compound 49): Compound 48 (0.065 g, 0.17 mmol) was taken along with 2-(4-methoxyphenyl)-4,4,5,5-tetramethyl-1,3,2-dioxaborolane (0.08 g, 0.34 mmol) in 1,4-dioxane (4 mL) and DMF (1 mL). 2(M) $Na_2CO_3$ solution (0.22 mL) and $Pd(PPh_3)_4$(0.016 g, 0.014 mmol) were added to the mixture and the reaction was performed according to Example 7. The residue was purified by silica gel column chromatography, eluting with 3% methanol in $CHCl_3$ to produce compound 49 (0.027 g, 31%) as a brown solid. $^1H$ NMR (600 MHz, $CDCl_3$+1 drop $CD_3OD$) δ ppm 9.01 (s, 1H), 8.20 (s, 1H), 8.05 (d, J=9 Hz, 2H), 7.99 (d, J=8.4 Hz, 1H), 7.91 (d, J=8.4 Hz, 1H), 7.65 (s, 1H), 7.53 (d, J=8.4 Hz, 2H), 7.03 (d, J=8.4 Hz, 2H), 7.01-7.00 (m, 3H), 6.91 (s, 1H), 4.40 (t, J=5.4 Hz, 2H), 4.33 (t, J=5.4 Hz, 2H), 3.86 (s, 3H), 3.83 (s, 3H). ESI-MS m/z 519.29 $(M+H^+)$.

Example 35

Synthesis of N-(2-(1H-imidazol-1-yl)ethyl)-6-(4-methoxyphenyl)-3-(1,3,4-oxadiazol-2-yl)quinolin-4-amine (compound 50): Compound 48 (0.07 g, 0.18 mmol) was taken along with 2-(4-methoxyphenyl)-4,4,5,5-tetramethyl-1,3,2-dioxaborolane (0.043 g, 0.18 mmol) in 1,4-dioxane (4 mL) and DMF (1 mL). 2(M) $Na_2CO_3$ solution (0.24 mL) and $Pd(PPh_3)_4$(0.017 g, 0.014 mmol) were added to the mixture and the reaction was performed according to Example 7. The residue was purified by silica gel column chromatography, eluting with 5% methanol in $CHCl_3$ to produce compound 50 (0.02 g, 27%) as a yellow solid. $^1H$ NMR (600 MHz, $CDCl_3$) δ ppm 9.05 (s, 1H), 8.62 (t, J=4.2 Hz, 1H), 8.52 (s, 1H), 8.21 (d, J=1.8 Hz, 1H), 8.08 (d, J=9 Hz, 1H), 7.95 (dd, J=9, 1.8 Hz, 1H), 7.58 (d, J=8.4 Hz, 2H), 7.46 (s, 1H), 7.06 (d, J=8.4 Hz, 2H), 6.98 (s, 1H), 6.91 (s, 1H), 4.36-4.33 (m, 4H), 3.90 (s, 3H). ESI-MS m/z 413.16 $(M+H^+)$.

Example 36A

Synthesis of 5-(4-(3-(1H-imidazol-1-yl)propylamino)-6-bromoquinolin-3-yl)-1,3,4-oxadiazol-2-amine (compound 51): Compound 16 (0.5 g, 1.28 mmol) was dissolved in methanol (5 mL) and to it cyanogen bromide (0.163 g, 1.54 mmol) was added. The mixture was refluxed for 4 hours. Excess solvent was evaporated and the organic part was extracted with $CHCl_3$, washed with saturated $NaHCO_3$ solution, dried and concentrated to give compound 51 (0.1 g, 19%). $^1H$ NMR (300 MHz, $CD_3OD$) δ ppm 8.81, (s, 1H), 8.48 (d, J=1.5 Hz, 1H), 7.97 (s, 1H), 7.83 (d, J=1.8 Hz, 1H), 7.82 (s, 1H), 7.29 (d, J=0.9 Hz, 1H), 7.11 (s, 1H), 4.31 (t, J=7.2 Hz, 2H), 3.89 (t, J=6.3 Hz, 2H), 2.37-2.33 (m, 2H). ESI-MS m/z 414.23$(M+H^+)$.

Example 36

Synthesis of 5-(4-(3-(1H-imidazol-1-yl)propylamino)-6-(4-methoxyphenyl)quinolin-3-yl)-1,3,4-oxadiazol-2-amine (compound 52): Compound 51 (0.07 g, 0.17 mmol) was taken along with 2-(4-methoxyphenyl)-4,4,5,5-tetramethyl-1,3,2-dioxaborolane (0.08 g, 0.34 mmol) in 1,4-dioxane (4 mL) and DMF (2 mL). 2(M) Na₂CO₃ solution (0.25 mL) and Pd(PPh₃)₄ (0.016 g, 0.014 mmol) were added to the mixture and the reaction was performed according to Example 7. The residue was purified by silica gel column chromatography, eluting with 6% methanol in CHCl₃ to produce compound 52 (0.017 g, 23%) as a brown solid. $^1$H NMR (600 MHz, DMSO-$d_6$) δ ppm 8.72 (s, 1H), 8.49 (s, 1H), 8.09 (d, J=8.4 Hz, 1H), 7.96 (d, J=8.4 Hz, 1H), 7.77 (d, J=8.4 Hz, 2H), 7.57 (s, 1H), 7.43 (s, 1H), 7.40 (s, 1H), 7.12 (d, J=9 Hz, 2H), 4.26 (t, J=7.2 Hz, 2H), 3.85 (s, 3H), 3.82-3.80 (m, 2H), 2.30-2.25 (m, 2H). ESI-MS m/z 442.29 (M+H⁺).

Example 37A

Synthesis of N-(3-(1H-imidazol-1-yl)propyl)-6-bromo-3-(5-methyl-1,3,4-oxadiazol-2-yl)quinolin-4-amine (compound 53): Compound 16 (1 g, 2.57 mmol) was dissolved in ethanol (5 mL) and to the solution triethyl orthoacetate (5 mL, 27.27 mmol) was added. The reaction mixture was heated for 6 hours at 100° C. The compound was purified by column chromatography, eluting with 4% methanol in CHCl₃ to give 53 (0.25 g, 24%) as a yellow gummy compound. $^1$H NMR (300 MHz, CD₃OD) δ ppm 8.46 (s, 1H), 7.79-7.73 (m, 2H), 7.71 (s, 1H), 7.63 (d, J=4.8 Hz, 1H), 7.13 (d, J=3.6 Hz, 1H), 6.94 (s, 1H). 4.32-4.21 (m, 2H), 3.49 (t, J=6.9 Hz, 2H), 3.36 (s, 3H), 2.23-2.19 (m, 2H). (ESI-MS m/z 413.24 (M+H⁺).

Example 37

Synthesis of N-(3-(1H-imidazol-1-yl)propyl)-6-(4-methoxyphenyl)-3-(5-methyl-1,3,4-oxadiazol-2-yl)quinolin-4-amine (compound 54): Compound 53 (0.10 g, 0.24 mmol) was taken along with 2-(4-methoxyphenyl)-4,4,5,5-tetramethyl-1,3,2-dioxaborolane (0.11 g, 0.5 mmol) in 1,4-dioxane (4 mL) and DMF (1 mL). 2(M) Na₂CO₃ solution (0.3 mL) and Pd(PPh₃)₄ (0.023 g, 0.02 mmol) were added to the mixture and the reaction was performed according to Example 7. It took 6 hours to complete the reaction. The residue was purified by silica gel column chromatography, eluting with 4% methanol in CHCl₃ to produce compound 54 (0.033 g, 31%) as a white solid. $^1$H NMR (600 MHz, CDCl₃) δ ppm 9.02 (s, 1H), 8.73 (t, J=4.8 Hz, —NH), 8.29 (d, J=1.8 Hz, 1H), 8.04 (d, J=9 Hz, 1H), 7.91 (dd, J=8.4, 1.8 Hz, 1H), 7.55 (d, J=8.4 Hz, 2H), 7.45 (s, 1H), 7.04 (d, J=8.4 Hz, 2H), 7.03 (s, 1H), 6.90 (s, 1H), 4.20 (t, J=7.2 Hz, 2H), 3.97-3.93 (m, 2H), 3.88 (s, 3H), 2.69 (s, 3H), 2.34-2.30 (m, 2H). ESI-MS m/z 441.72 (M+H⁺).

Example 38A

Synthesis of ethyl 4-((3-(1H-pyrrol-1-yl)propyl)amino)-6-bromoquinoline-3-carboxylate (compound 55): Compound 4 (1 g, 3.18 mmol) was dissolved in 1,4-dioxane (5 mL) under N₂ atmosphere. To the reaction mixture dry DIPEA (1.3 mL, 7.98 mmol) and 3-(1H-pyrrol-1-yl)propan-1-amine (0.793 g, 6.39 mmol) were added respectively. The reaction mixture was allowed to stir for 12 hours at 60° C. The reaction mixture was cooled to room temperature and extracted with ethyl acetate. The crude mass obtained was purified by column chromatography by 50% Ethyl acetate in pet ether to give compound 55 (0.1 g, 10%) as a white solid. $^1$H NMR (DMSO-$d_6$, 300 MHz) δ ppm 8.78 (s, 1H), 8.53 (d, J=1.5 Hz, 1H), 8.36 (t, J=4.8 Hz, —NH), 7.85 (dd, J=8.8, 1.8 Hz, 1H), 7.76 (d, J=9 Hz, 1H), 6.67 (t, J=1.8 Hz, 2H), 5.95 (t, J=1.8 Hz, 2H), 4.31 (q, J=7.2 Hz, 2H), 3.97 (t, J=6.6 Hz, 2H), 3.44-3.38 (m, 2H), 2.15-2.06 (m, 2H), 1.32 (t, J=7.2 Hz, 3H).

Example 38B

Synthesis of 4-((3-(1H-pyrrol-1-yl)propyl)amino)-6-bromoquinoline-3-carbohydrazide (compound 56): Compound 55 (0.2 g, 0.498 mmol) was dissolved in ethanol (4 mL). To the solution hydrazine hydrate (4 mL) was added. The reaction mixture was stirred for 12 hours at room temperature. Ethanol was removed under vacuum. The residue was then dissolved in CHCl₃ and the organic layer was washed with water and brine, dried and concentrated to give compound 56 (0.150 g, 78%) as a yellow solid. $^1$H NMR (CDCl₃+1 drop CD₃OD, 300 MHz) δ ppm 8.70 (br. s, —NH), 8.62 (s, 1H), 8.16 (s, 1H), 7.82 (d, J=9 Hz), 7.70 (d, J=10.8 Hz, 1H), 6.63 (t, J=1.8 Hz, 2H), 6.15 (t, J=1.8 Hz, 2H), 4.08 (t, J=6.6 Hz, 2H), 3.67-3.61 (m, 2H), 2.25-2.16 (m, 2H). ESI-MS m/z 388.01 (M+H⁺).

Example 38C

Synthesis of N-(3-(1H-pyrrol-1-yl)propyl)-6-bromo-3-(1,3,4-oxadiazol-2-yl)quinolin-4-amine (compound 57): Compound 56 (0.190 g, 0.490 mmol) was taken in triethyl orthoformate (4 mL) and the mixture was heated for 12 hours at 110° C. Then the reaction mixture was allowed to come to room temperature. Excess hexane was added to the mixture. A precipitation formed which was filtered and purified by column chromatography, eluting with 1% methanol in CHCl₃ to give compound 57 (0.07 g, 39%) as a light yellow solid. $^1$H NMR (CDCl₃, 400 MHz) δ ppm 9.29 (br. s, —NH), 8.69 (s, 1H), 8.17 (s, 1H), 7.79 (d, J=9 Hz, 1H), 7.74 (dd, J=9 Hz, 1.8 Hz, 1H), 6.67 (br. s, 1H), 6.63 (t, J=1.8 Hz, 2H), 6.13 (t, J=1.8 Hz, 2H), 4.27-4.20 (m, 2H), 4.11 (t, J=6.6 Hz, 2H), 2.24-2.16 (m, 2H).

Example 38

Synthesis of N-(3-(1H-pyrrol-1-yl)propyl)-6-(4-methoxyphenyl)-3-(1,3,4-oxadiazol-2-yl)quinolin-4-amine (compound 58): Compound 57 (0.053 g, 0.133 mmol) was dissolved in 1,4-dioxane (2 mL) and DMF (0.5 mL) under argon atmosphere. 4-[4,4,5,5-Tetramethyl-1,3,2-dioxaborolan-2-yl]anisole (0.046 g, 0.20 mmol) was added to the mixture. 2(M) Na₂CO₃ solution (0.1 mL) was added to the reaction mixture and argon (Ar) was purged for 15 minutes. Then Pd(PPh₃)₂Cl₂ (0.009 g, 0.01 mmol) was added to the reaction mixture and Ar purging was performed for about 10 minutes. Then the mixture was heated for 12 hours at 100° C. 1,4-Dioxane was removed under vacuum, the residue then dissolved in CHCl₃ and the organic layer was washed with water and brine, dried and concentrated. The residue was purified by column chromatography, eluting with 80% ethyl acetate in pet ether to give compound 58 (0.021 g, 37%) as a brown solid. $^1$H NMR (CDCl₃, 400 MHz) δ ppm 9.06 (s, 1H), 8.82 (br. s, —NH), 8.50 (s, 1H), 8.34 (s, 1H), 8.04 (d, J=9 Hz, 1H), 7.91 (d, J=9 Hz, 2H), 7.57 (d, J=9 Hz, 2H), 7.05 (d, J=9 Hz, 1H), 6.63 (s, 2H), 6.12 (s, 2H), 4.14 (t, J=6 Hz, 2H), 3.97-3.92 (m, 2H), 3.89 (s, 3H), 2.38-2.29 (m, 2H). ESI-MS m/z 426.02 (M+H⁺).

Example 39A

Synthesis of ethyl 6-bromo-4-((3-(pyrrolidin-1-yl)propyl)amino)quinoline-3-carboxylate (compound 59): Compound 4 (1 g, 3.19 mmol) was dissolved in 1,4-dioxane (5 mL) under N$_2$ atmosphere. To the reaction mixture dry DIPEA (1.3 mL, 7.98 mmol) and 3-(pyrrolidin-1-yl)propan-1-amine (0.818 g, 6.39 mmol) were added respectively. The reaction mixture was allowed to stir for 12 hours at 60° C. The reaction mixture was cooled to room temperature and extracted with Chloroform. The crude mass obtained was purified by column chromatography by 10% MeOH in CHCl$_3$ to give compound 59 (220 mg, 17%) as a white solid. $^1$H NMR (CDCl$_3$, 400 MHz) δ ppm 9.24 (t, J=4 Hz, 1H), 9.02 (s, 1H), 8.31 (d, J=4 Hz, 1H), 7.78 (d, J=8.8 Hz, 1H), 7.70 (dd, J=8.8, 2 Hz, 1H), 4.37 (q, J=7.2 Hz, 2H), 3.81-3.76 (m, 2H), 2.67 (t, J=6.8 Hz, 2H), 2.57 (t, J=7.2 Hz, 4H), 2.00-1.94 (m, 2H), 1.84-1.81 (m, 4H), 1.40 (t, J=7.2 Hz, 3H).

Example 39B

Synthesis of 6-bromo-4-((3-(pyrrolidin-1-yl)propyl) amino)quinoline-3-carbohydrazide (compound 60): Compound 59 (0.3 g, 0.96 mmol) was dissolved in ethanol (4 mL). To the solution hydrazine hydrate (4 mL) was added. The reaction mixture was stirred for 10 hours at room temperature. Ethanol was removed under vacuum. The residue was then dissolved in CHCl$_3$ and the organic layer was washed with water and brine, dried and concentrated to give compound 60 (0.19 g, 66%) as a yellow solid. $^1$H NMR (CDCl$_3$+1 drop CD$_3$OD, 400 MHz) δ ppm 8.70 (br. s, —NH), 8.39 (s, 1H), 7.93 (s, 1H), 7.83 (br. s, 1H), 7.74 (d, J=9.2 Hz, 1H), 7.65 (dd, J=8.8, 2 Hz, 1H), 3.49-3.45 (m, 2H), 2.74 (t, J=5.6 Hz, 2H), 2.63 (t, J=5.2 Hz, 4H), 1.99-1.95 (m, 4H), 1.87-1.81 (m, 2H).

Example 39C

Synthesis of 6-bromo-3-(1,3,4-oxadiazol-2-yl)-N-(3-(pyrrolidin-1-yl)propyl)quinolin-4-amine (compound 61): Compound 60 (0.19 g, 0.485 mmol) was taken in triethyl orthoformate (3 mL) and the mixture was heated for 12 hours at 110° C. Then the reaction mixture was allowed to come to room temperature. Excess hexane was added to the mixture. A precipitation formed which was filtered and purified by column chromatography, eluting with 2% methanol in CHCl$_3$ to give compound 61 (0.06 g, 31%) as a light yellow solid. $^1$H NMR (CDCl$_3$+1 drop CD$_3$OD, 400 MHz) δ ppm 8.97 (s, 1H), 8.85 (t, J=6.4 Hz, 1H), 8.47 (s, 1H), 8.41 (d, J=2 Hz, 1H), 7.83 (d, J=8.8 Hz, 1H), 7.73 (dd, J=8.8, 2 Hz, 1H), 3.90-3.86 (m, 2H), 2.72 (t, J=6.8 Hz, 2H), 2.60 (t, J=7.6 Hz, 4H), 2.09-2.03 (m, 2H), 1.85-1.81 (m, 4H).

Example 39

Synthesis of 6-(4-methoxyphenyl)-3-(1,3,4-oxadiazol-2-yl)-N-(3-(pyrrolidin-1-yl)propyl)quinolin-4-amine (compound 62): Compound 61 (0.053 g, 0.132 mmol) was dissolved in 1,4-dioxane (2 mL) and DMF (0.5 mL) under Ar atmosphere. Then 4-[4,4,5,5-tetramethyl-1,3,2-dioxaborolan-2-yl]anisole (0.046 g, 0.198 mmol) was added to the mixture. 2(M) Na$_2$CO$_3$ solution (0.1 mL) was added to the reaction mixture and Ar was purged for 15 minutes. Then Pd(PPh$_3$)$_2$Cl$_2$ (0.009 g, 0.01 mmol) was added to the reaction mixture and Ar purging was performed for about 10 minutes. Then the mixture was heated for 12 hours at 100° C. 1,4-Dioxane was removed under vacuum, the residue then dissolved in CHCl$_3$ and the organic layer was washed with water and brine, dried and concentrated. The residue was purified by column chromatography, eluting with 5% MeOH in CHCl$_3$ to give compound 62 (0.021 g, 37%) as a brown solid. $^1$H NMR (CDCl$_3$, 400 MHz) δ ppm 9.00 (s, 1H), 8.72 (t, J=4 Hz, —NH), 8.50 (s, 1H), 8.38 (d, J=2 Hz, 1H), 8.00 (d, J=8.4 Hz, 1H), 7.90 (dd, J=8.8 Hz, 1.6 Hz, 1H), 7.59 (d, J=8.8 Hz, 2H), 7.02 (d, J=8.4 Hz, 2H), 4.07-4.03 (m, 2H), 3.86 (s, 3H), 2.83 (t, J=7.2 Hz, 2H), 2.73 (t, J=6.8 Hz, 4H), 2.21-2.14 (m, 2H), 1.86-1.83 (m, 4H). ESI-MS m/z 430.01 (M+H$^+$).

Example 40A

Synthesis of 5-((4-bromophenylamino)methylene)-2,2-dimethyl-1,3-dioxane-4,6-dione (compound 63): Compound 1 (10 g, 58.13 mmol) and 2,2-dimethyl-1,3-dioxane-4,6-dione (10.05 g, 69.76 mmol) were dissolved in ethanol (30 mL). Triethyl orthoformate (10.65 mL, 63.94 mmol) was added to the mixture and heated for 2 hours at 80° C. The solid was filtered and washed with cold ethanol to get compound 63 as a white solid. $^1$H NMR (300 MHz, CDCl$_3$) δ ppm 8.59 (d, J=14.4 Hz, 1H), 7.56 (d, J=9 Hz, 2H), 7.14 (d, J=8.7 Hz, 2H), 1.75 (s, 6H). ESI-MS m/z 349.96 (M+Na$^+$).

Example 40B

Synthesis of 6-bromoquinolin-4-ol (compound 64): A solution of compound 63(4 g, 12.26 mmol) in dowtherm (20 mL) was heated for 2 hours at 180° C. The reaction mixture was allowed to come to room temperature. Then excess hexane was added to the reaction mixture. A solid formed which was allowed to settle down for 30 minutes. Then the solid was filtered and washed with hexane and tert-butyl methyl ether to give compound 64 (1.6 g, 58%) as a brown solid. $^1$H NMR (300 MHz, DMSO-d$_6$) δ ppm 7.63 (s, 1H), 7.60 (s, 1H), 7.56 (s, 1H), 7.53 (s, 1H), 7.44 (s, 1H). ESI-MS m/z 224.04 (M+H$^+$).

Example 40C

Synthesis of 6-bromo-3-iodoquinolin-4-ol (compound 65): Compound 64 (0.5 g, 2.23 mmol) was dissolved in 2(N) NaOH solution (10 mL). I$_2$ (0.34 g, 2.7 mmol) in 20% KI solution in H$_2$O (10 mL) was added dropwise to the mixture and allowed to stir for 3 hours at room temperature. The reaction mixture was acidified with AcOH. The solid obtained was filtered and washed several times with water to give compound 65 (0.35 g, 45%) as a grey solid. NMR (300 MHz, CDCl$_3$) δ ppm 7.76 (d, J=8.7 Hz, 1H), 7.62 (d, J=9 Hz, 1H), 7.51 (s, 1H), 7.41 (d, J=5.4 Hz, 1H). ESI-MS m/z 371.89 (M+H$^+$).

Example 40D

Synthesis of 6-bromo-4-chloro-3-iodoquinoline (compound 66): Compound 65 (0.5 g, 1.43 mmol) was taken in POCl$_3$ (5 mL) in ice-cold condition. The reaction mixture was allowed to come to room temperature and then heated for 7 hours at 100° C. Then the reaction mixture was poured into crushed ice and neutralised with saturated sodium bicarbonate solution. The organic part was extracted with ethyl acetate, washed with water and brine, concentrated and dried. The solid was purified by silica gel flash column chromatography, eluting with 1% ethyl acetate in hexane to give compound 66 (0.3 g, 57%) as an off-white solid. $^1$H NMR (300 MHz, CDCl$_3$) δ ppm 9.14 (s, 1H), 8.46 (s, 1H), 7.99 (d, J=9 Hz, 1H), 7.88 (d, J=9 Hz, 1H). ESI-MS m/z 369.94 (M+H$^+$).

Example 40E

Synthesis of N-(3-(1H-imidazol-1-yl)propyl)-6-bromo-3-iodoquinolin-4-amine (compound 67): Compound 66 (0.3 g, 0.8 mmol) was dissolved in 1,4-dioxane (4 mL) and DMF (1 mL) under $N_2$ atmosphere. To the reaction mixture dry DIPEA (0.28 mL, 1.6 mmol) and 3-(1H-imidazol-1-yl)propan-1-amine (0.14 mL, 1.2 mmol) were added respectively. The reaction mixture was heated for 12 hours at 70° C. Then solvent was evaporated and the organic part was extracted by $CHCl_3$ and purified by column chromatography to give compound 67 (0.15 g, 40%) as a brown solid. $^1H$ NMR (300 MHz, $CD_3OD$) δ ppm 8.79 (s, 1H), 8.28 (br. s, —NH), 7.91 (s, 1H), 7.79 (d, J=2.1 Hz, 1H), 7.66 (s, 1H), 7.62 (s, 1H), 7.14 (s, 1H), 7.08 (s, 1H), 4.16-4.13 (m, 2H), 3.69 (t, J=6.9 Hz, 2H), 2.24-2.19 (m, 2H). ESI-MS m/z 457.05 $(M+H^+)$.

Example 40F

Synthesis of N-(3-(1H-imidazol-1-yl)propyl)-6-bromo-3-(furan-2-yl)quinolin-4-amine (compound 68): Compound 67 (0.08 g, 0.18 mmol) was taken along with furan-2-ylboronic acid (0.024 g, 0.22 mmol) in DMF (4 mL). 2(M) $Na_2CO_3$ solution (0.23 mL) and $Pd(PPh_3)_4$ (0.017 g, 0.014 mmol) were added to the mixture and the reaction was performed according to Example 7. The residue was purified by silica gel column chromatography, eluting with 4% methanol in $CHCl_3$ to produce compound 68 (0.029 g, 42%) as a brown solid. H NMR (600 MHz, $CDCl_3$) δ ppm 8.72 (s, 1H), 8.14 (d, J=1.8 Hz, 1H), 7.89 (d, J=8.4 Hz, 1H), 7.71 (dd, J=9, 2.4 Hz, 1H), 7.62 (d, J=1.8 Hz, 1H), 7.39 (s, 1H), 7.06 (s, 1H), 6.81 (s, 1H), 6.67 (d, J=3 Hz, 1H), 6.62-6.61 (m, 1H), 3.93 (t, J=7.2 Hz, 2H), 3.36-3.32 (m, 2H), 2.08-2.03 (m, 2H). ESI-MS m/z 397.02 $(M+H^+)$.

Example 40

Synthesis of N-(3-(1H-imidazol-1-yl)propyl)-6-(6-aminopyridin-3-yl)-3-(furan-2-yl)quinolin-4-amine (compound 69): Compound 68 (0.07 g, 0.18 mmol) was taken along with 5-(4,4,5,5-tetramethyl-1,3,2-dioxaborolan-2-yl)pyridin-2-amine (0.079 g, 0.36 mmol) in 1,4-dioxane (4 mL) and DMF (1 mL). 2(M) $Na_2CO_3$ solution (0.3 mL) and $Pd(PPh_3)_4$ (0.017 g, 0.014 mmol) were added to the mixture and the reaction was performed according to Example 7. It took 28 hours to complete the reaction. The residue was purified by silica gel column chromatography to get compound 69 (0.035 g, 48%) as a brown solid. $^1H$ NMR (300 MHz, $CDCl_3$) δ ppm 8.50 (s, 1H), 8.39 (d, J=1.8 Hz, 1H), 8.35 (s, 1H), 8.10 (dd, J=8.7, 1.2 Hz, 1H), 8.00 (dd, J=8.4, 2.7 Hz, 1H), 7.92 (d, J=8.7 Hz, 1H), 7.74-7.63 (m, 2H), 7.10 (s, 1H), 6.99 (s, 1H), 6.78 (d, J=8.7 Hz, 1H), 6.64 (s, 2H), 4.01 (t, J=6.9 Hz, 2H), 3.10 (t, J=7.5 Hz, 2H), 2.15-2.06 (m, 2H). ESI-MS m/z 411.08 $(M+H^+)$.

Example 41A

Synthesis of N-(3-(1H-imidazol-1-yl)propyl)-3-(6-aminopyridin-3-yl)-6-bromoquinolin-4-amine (compound 72): Compound 67 (0.1 g, 0.22 mmol) and 5-(4,4,5,5-tetramethyl-1,3,2-dioxaborolan-2-yl)pyridin-2-amine (0.058 g, 0.26 mmol) were dissolved in DMF (5 mL). 2(M) $Na_2CO_3$ solution (0.22 mL) and $Pd(PPh_3)_4$ (0.02 g, 0.018 mmol) were added to the mixture and the reaction was performed according to Example 7. The reaction mixture was heated at 80° C. for 12 hours. The residue was purified by silica gel column chromatography to get compound 72 (0.065 g, 70%). $^1H$ NMR (300 MHz, $CDCl_3$) δ ppm 8.48 (s, 1H), 8.13 (d, J=2.1 Hz, 1H), 8.03 (d, J=1.8 Hz, 1H), 7.91 (d, J=9 Hz, 1H), 7.73 (dd, J=9, 1.8 Hz, 1H), 7.46 (dd, J=8.4, 2.1 Hz, 1H), 7.32 (s, 1H), 7.06 (s, 1H), 6.78 (s, 1H), 6.63 (d, J=8.4 Hz, 1H), 3.88 (t, J=6.9 Hz, 2H), 3.16-3.09 (m, 2H), 2.00-1.91 (m, 2H). ESI-MS m/z 423.27 $(M+H^+)$.

Example 41

Synthesis of N-(3-(1H-imidazol-1-yl)propyl)-3-(6-aminopyridin-3-yl)-6-(4-methoxyphenyl)quinolin-4-amine (compound 73): Compound 72 (0.05 g, 0.12 mmol) and 2-(4-methoxyphenyl)-4,4,5,5-tetramethyl-1,3,2-dioxaborolane (0.055 g, 0.24 mmol) were dissolved in a mixture of solvent of 1,4-dioxane (4 mL) and DMF (0.5 mL). 2(M) $Na_2CO_3$ solution (0.15 mL) and $Pd(PPh_3)_4$ (0.011 g, 0.01 mmol) were added to the mixture and the reaction was performed according to Example 7. The reaction mixture was heated at 100° C. for 10 hours. The residue was purified by silica gel column chromatography to get compound 73 (0.022 g, 41%) as a brown solid. $^1H$ NMR (300 MHz, $CDCl_3$) δ ppm 8.47 (s, 1H), 8.17 (d, J=1.5 Hz, 1H), 8.09 (d, J=8.7 Hz, 1H), 7.95 (s, 1H), 7.89 (dd, J=8.7, 1.8 Hz, 1H), 7.62 (d, J=8.7 Hz, 2H), 7.50 (dd, J=8.4, 2.4 Hz, 1H), 7.29 (d, J=7.2 Hz, 1H), 7.05 (d, J=8.7 Hz, 2H), 7.01 (s, 1H), 6.75 (s, 1H), 6.64 (d, J=8.4 Hz, 1H), 3.89 (s, 3H), 3.85 (d, J=6.9 Hz, 2H), 3.21-3.15 (m, 2H), 2.00-1.91 (m, 2H). ESI-MS m/z 451.51 $(M+H^+)$.

Example 42A

Synthesis of ethyl 6-bromo-4-(methylamino)quinoline-3-carboxylate (compound 74): Compound 4 (0.5 g, 1.59 mmol) was dissolved in THF (3 mL) under $N_2$ atmosphere in a sealed tube. To the reaction mixture dry DIPEA (0.6 mL, 3.18 mmol) and methylamine (0.7 mL, 15.9 mmol) were added respectively. The reaction mixture was heated for 16 hours at 60° C. Then organic part was extracted with chloroform. The crude was purified by column chromatography to obtain compound 74 (0.2 g, 41%). $^1H$ NMR (300 MHz, $CDCl_3$) δ ppm 9.48 (br. s, —NH), 9.07 (s, 1H), 8.48 (d, J=1.8 Hz, 1H), 7.81 (d, J=9 Hz, 1H), 7.72 (dd, J=8.7, 2.1 Hz, 1H), 4.38 (q, J=7.2 Hz, 2H), 3.50 (d, J=5.4 Hz, 3H), 1.42 (t, J=7.2 Hz, 3H). ESI-MS m/z 309.02 $(M+H^+)$.

Example 42B

Synthesis of 6-bromo-4-(methylamino)quinoline-3-carbohydrazide (compound 75): Compound 74 (0.5 g, 1.62 mmol) was dissolved in ethanol (8 mL). To the solution hydrazine hydrate (8 mL) was added. The reaction mixture was stirred for 12 hours at room temperature. Ethanol was removed under vacuum. The residue was then dissolved in $CHCl_3$ and the organic layer was washed with water and brine, dried and concentrated to give compound 75 (0.34 g, 73%) as a yellow solid. $^1H$ NMR (300 MHz, DMSO-$d_6$) δ ppm 9.60 (s, 1H), 8.52 (s, 1H), 8.27 (s, —CONH—, 1H), 7.76 (dd, J=9, 1.5 Hz, 1H), 7.71 (d, J=9 Hz, 1H), 4.51 (br. s, sec. —NH, 1H), 2.93 (d, J=5.1 Hz, 3H), 1.77 (s, —$CONHNH_2$, 2H). ESI-MS m/z 295.24 $(M+H^+)$.

Example 42C

Synthesis of 6-bromo-N-methyl-3-(1,3,4-oxadiazol-2-yl)quinolin-4-amine (compound 76): Compound 75 (0.5 g, 1.7 mmol) was taken in triethyl orthoformate (5 mL, 30.06 mmol) and the mixture was heated for 12 hours at 160° C. The compound was purified by column chromatography, eluting with 4% methanol in CHCl$_3$ to afford compound 76 (0.15 g, 29%) as a yellow solid. $^1$H NMR (300 MHz, CDCl$_3$) δ ppm 9.02 (s, 1H), 8.57 (s, 1H), 8.48 (s, 1H), 7.86 (d, J=9 Hz, 1H), 7.76 (dd, J=9, 1.5 Hz, 1H), 3.62 (d, J=5.1 Hz, 3H). ESI-MS m/z 304.86 (M+H$^+$).

Example 42

Synthesis of 6-(4-methoxyphenyl)-N-methyl-3-(1,3,4-oxadiazol-2-yl)quinolin-4-amine (compound 77): Compound 76 (0.1 g, 0.33 mmol) was taken along with 2-(4-methoxyphenyl)-4,4,5,5-tetramethyl-1,3,2-dioxaborolane (0.12 g, 0.51 mmol) in 1,4-dioxane (5 mL). 2(M) Na$_2$CO$_3$ solution (0.4 mL) and Pd(PPh$_3$)$_4$ (0.03 g, 0.03 mmol) were added to the mixture and the reaction was performed according to Example 1. The residue was purified by silica gel column chromatography to afford compound 77 (0.038 g, 35%) as a white solid. $^1$H NMR (600 MHz, CDCl$_3$) δ ppm 9.03 (s, —NH), 8.57 (s, 1H), 8.48 (s, 1H), 8.05 (d, J=8.4 Hz, 1H), 7.93 (d, J=8.4 Hz, 1H), 7.62 (d, J=7.8 Hz, 2H), 7.05 (d, J=7.8 Hz, 2H), 6.79 (s, 1H), 3.89 (s, 3H), 3.71 (d, J=4.8 Hz, 3H). ESI-MS m/z 333.13 (M+H$^+$).

Example 43

Synthesis of ethyl 4-((3-(1H-imidazol-1-yl)propyl)amino)-6-(4-methoxyphenyl)quinoline-3-carboxylate (compound 78): Compound 15 (0.1 g, 0.25 mmol) was taken along with 2-(4-methoxyphenyl)-4,4,5,5-tetramethyl-1,3,2-dioxaborolane (0.12 g, 0.51 mmol) in 1,4-dioxane (5 mL). 2(M) Na$_2$CO$_3$ solution (0.3 mL) and Pd(PPh$_3$)$_4$ (0.023 g, 0.02 mmol) were added to the mixture and the reaction was performed according to Example 1. The residue was purified by silica gel column chromatography to afford compound 78 (0.035 g, 33%) as a white solid. $^1$H NMR (600 MHz, CD$_3$OD) δ ppm 8.91 (s, 1H), 8.38 (s, 1H), 8.06 (d, J=8.4 Hz, 1H), 7.87 (d, J=8.4 Hz, 2H), 7.61 (d, J=7.2 Hz, 2H), 7.24 (s, 1H), 7.07-7.06 (m, 3H), 4.42 (q, J=7.2 Hz, 2H), 4.26 (t, J=6.6 Hz, 2H), 3.95 (t, J=6.6 Hz, 2H), 3.86 (s, 3H), 2.35-2.32 (m, 2H), 1.43 (t, J=7.2 Hz, 3H). ESI-MS m/z 431.08 (M+H$^+$).

Example 44

Synthesis of N-(3-(1H-imidazol-1-yl)propyl)-3-(1,3,4-oxadiazol-2-yl)-6-(4-(trifluoromethyl)phenyl)quinolin-4-amine (compound 79): Compound 17 (0.075 g, 0.19 mmol) was taken along with (4-(trifluoromethyl)phenyl)boronic acid (0.053 g, 0.28 mmol) in 1,4-dioxane (4 mL) and DMF (1 mL). 2(M) Na$_2$CO$_3$ solution (0.2 mL) and Pd(PPh$_3$)$_4$ (0.022 g, 0.02 mmol) were added to the mixture and the reaction was performed according to Example 7. It took 12 hours to complete the reaction. The residue was purified by silica gel column chromatography, eluting with 4% methanol in CHCl$_3$ to produce compound 79 (0.025 g, 29%) as a light yellow solid. $^1$H NMR (600 MHz, CDCl$_3$) δ ppm 9.13 (s, 1H), 8.84 (br. s, —NH), 8.53 (s, 1H), 8.37 (s, 1H), 8.12 (d, J=8.4 Hz, 1H), 7.95 (dd, J=9.0, 1.2 Hz, 1H), 7.77 (d, J=7.8 Hz, 2H), 7.72 (d, J=7.8 Hz, 1H), 7.53 (s, 1H), 7.07 (s, 1H), 6.92 (s, 1H), 4.29 (t, J=7.2 Hz, 2H), 4.00-3.98 (m, 2H), 2.39-2.35 (m, 2H). ESI-MS m/z 465.17 (M+H$^+$).

Example 45

Synthesis of N-(3-(1H-imidazol-1-yl)propyl)-6-(4-(dimethylamino)phenyl)-3-(1,3,4-oxadiazol-2-yl)quinolin-4-amine (compound 80): Compound 17 (0.08 g, 0.2 mmol) was taken along with (4-(dimethylamino)phenyl)boronic acid (0.050 g, 0.3 mmol) in 1,4-dioxane (4 mL) and DMF (1 mL). 2(M) Na$_2$CO$_3$ solution (0.25 mL) and Pd(PPh$_3$)$_4$ (0.023 g, 0.02 mmol) were added to the mixture and the reaction was performed according to Example 7. It took 12 hours to complete the reaction. The residue was purified by silica gel column chromatography, eluting with 8% methanol in CHCl$_3$ to produce compound 80 (0.027 g, 31%) as a yellow solid. $^1$H NMR (600 MHz, CDCl$_3$+1 drop CD$_3$OD) δ ppm 8.96 (s, 1H), 8.56 (s, 1H), 8.27 (s, 1H), 7.97 (d, J=9.0 Hz, 1H), 7.92 (d, J=7.8 Hz, 1H), 7.50-7.49 (m, 3H), 6.97 (s, 1H), 6.90 (s, 1H), 6.82 (d, J=8.4 Hz, 2H), 4.19 (t, J=7.2 Hz, 2H), 3.98 (t, J=6.0 Hz, 2H), 2.78 (s, 6H), 2.33-2.31 (m, 2H). ESI-MS m/z 440.22 (M+H$^+$).

Example 46

Synthesis of N-(3-(1H-imidazol-1-yl)propyl)-3-(1,3,4-oxadiazol-2-yl)-6-(4-(trifluoromethoxy)phenyl)quinolin-4-amine (compound 81): Compound 17 (0.08 g, 0.2 mmol) was taken along with (4-(trifluoromethoxy)phenyl)boronic acid (0.082 g, 0.4 mmol) in 1,4-dioxane (4 mL) and DMF (1 mL). 2(M) Na$_2$CO$_3$ solution (0.25 mL) and Pd(PPh$_3$)$_4$ (0.023 g, 0.02 mmol) were added to the mixture and the reaction was performed according to Example 7. It took 12 hours to complete the reaction. The residue was purified by silica gel column chromatography, eluting with 5% methanol in CHCl$_3$ to produce compound 81 (0.033 g, 34%) as an off-white solid. $^1$H NMR (600 MHz, CDCl$_3$+1 drop CD$_3$OD) δ ppm 9.02 (s, 1H), 8.60 (s, 1H), 8.30 (s, 1H), 8.04-8.01 (m, 1H), 7.90 (d, J=9.0 Hz, 1H), 7.60-7.59 (m, 3H), 7.33 (d, J=7.8 Hz, 1H), 6.97 (s, 1H), 6.91 (s, 1H), 4.23-4.20 (m, 2H), 3.97 (t, J=6.0 Hz, 2H), 2.36-2.32 (m, 2H). ESI-MS m/z 481.16 (M+H$^+$).

Example 47

Synthesis of N-(3-(1H-Imidazol-1-yl)propyl)-6-(3-methoxyphenyl)-3-(1,3,4-oxadiazol-2-yl)quinolin-4-amine (compound 82): Compound 17 (0.10 g, 0.25 mmol) was taken along with (3-methoxyphenyl)boronic acid (0.06 g, 0.38 mmol) in 1,4-dioxane (4 mL) and DMF (1 mL). 2(M) Na$_2$CO$_3$ solution (0.3 mL) and Pd(PPh$_3$)$_4$ (0.023 g, 0.02 mmol) were added to the reaction mixture, and the reaction was performed according to Example 7. The residue was purified by silica gel column chromatography, eluting with 9% methanol in CHCl$_3$ to get compound 82 as a pale yellow solid (0.052 g, 49%). mp 96° C. $^1$H NMR (400 MHz, CDCl$_3$) δ ppm 9.07 (s, 1H), 8.78 (t, J=4.0 Hz, —NH), 8.50 (s, 1H), 8.34 (d, J=2.0 Hz, 1H), 8.05 (d, J=8.8 Hz, 1H), 7.93 (dd, J=8.4, 2 Hz, 1H), 7.44 (d, J=4.0 Hz, 1H), 7.41 (d, J=8.0 Hz, 1H), 7.18 (dd, J=7.6, 1.2 Hz, 1H), 7.14 (m, 1H), 7.01 (s, 1H), 6.94 (dd, J=8.4, 1.6 Hz, 1H), 6.89 (s, 1H), 4.19 (t, J=6.8 Hz, 2H), 3.99-3.95 (m, 2H), 3.88 (s, 3H), 2.37-2.30 (m, 2H). ESI-MS m/z 427.37 (M+H$^+$).

Example 48

Synthesis of N-(3-(1H-Imidazol-1-yl)propyl)-6-(2-methoxyphenyl)-3-(1,3,4-oxadiazol-2-yl)quinolin-4-amine (compound 83): Compound 17 (0.08 g, 0.2 mmol) was taken along with (2-methoxyphenyl)boronic acid (0.06 g, 0.4 mmol) in 1,4-dioxane (4 mL) and DMF (1 mL). 2(M) Na$_2$CO$_3$ solution (0.3 mL) and Pd(PPh$_3$)$_4$ (0.018 g, 0.02 mmol) were added to the reaction mixture, and the reaction was performed according to Example 7. The residue was purified by silica gel column chromatography, eluting with 8% methanol in CHCl₃ to get compound 83 as a white solid (0.024 g, 23%). mp 90° C. ¹H NMR (400 MHz, CDCl₃) δ ppm 9.07 (s, 1H), 8.82 (br. s, —NH), 8.50 (s, 1H), 8.39 (s, 1H), 8.03 (d, J=6.6 Hz, 1H), 7.89 (d, J=6.3 Hz, 1H), 7.44 (s, 1H), 7.39-7.35 (m, 2H), 7.09 (t, J=5.4 Hz, 1H), 7.04-7.00 (m, 2H), 6.88 (s, 1H), 4.18 (t, J=5.1 Hz, 2H), 3.97-3.93 (m, 2H), 3.80 (s, 3H), 2.33-2.30 (m, 2H). ESI-MS m/z 427.29 (M+H⁺).

Example 49

Synthesis of tert-butyl (4-(4-((3-(1H-imidazol-1-yl)propyl)amino)-3-(1,3,4-oxadiazol-2-yl)quinolin-6-yl)phenyl)(methyl)carbamate (compound 84): Compound 17 (0.09 g, 0.226 mmol) was taken along with tert-butyl methyl(4-(4,4,5,5-tetramethyl-1,3,2-dioxaborolan-2-yl)phenyl)carbamate (0.09 g, 0.271 mmol) in 1,4-dioxane (2 mL) and DMF (0.5 mL). 2(M) Na₂CO₃ solution (0.1 mL) and Pd(PPh₃)₄ (0.026 g, 0.01 mmol) were added to the mixture and the reaction was performed according to Example 7. It took 12 hours for the reaction to complete. The residue was purified by silica gel column chromatography, eluting with 2% methanol in CHCl₃ to produce compound 84 (0.035 g, 30%) as a yellow solid. ¹H NMR (CDCl₃, 300 MHz) δ ppm 9.06 (s, 1H), 8.86 (t, J=3.3 Hz, —NH), 8.55 (s, 1H), 8.33 (s, 1H), 8.07 (d, J=8.4 Hz, 1H), 7.93 (d, J=8.7 Hz, 1H), 7.62 (s, 1H), 7.58 (s, 1H), 7.55 (s, 1H), 7.39 (d, J=8.4 Hz, 2H), 7.04 (s, 1H), 6.93 (s, 1H), 4.24 (t, J=6.6 Hz, 2H), 4.02-3.96 (m, 2H), 3.69 (s, 9H), 3.23 (s, 3H), 2.41-2.32 (m, 2H). ESI-MS m/z 526.29 (M+H⁺).

Example 50

Synthesis of N-(3-(1H-imidazol-1-yl)propyl)-6-(4-(methylamino)phenyl)-3-(1,3,4-oxadiazol-2-yl)quinolin-4-amine (compound 85): Compound 84 (0.022 g, 0.041 mmol) was taken in 1,4-dioxane (0.2 mL) and 4(M) HCl (0.06 mL) in 1,4-dioxane was added portion wise under cooling condition. After complete addition reaction mixture was allowed to stir at room temperature for 1 hour. The precipitation formed in the reaction mixture was neutralized by saturated NaHCO₃ solution and extracted with CHCl₃. The residue was purified by silica gel column chromatography, eluting with 10% methanol in CHCl₃ to produce compound 85 (0.007 g, 39%) as a yellow solid. ¹H NMR (CDCl₃+1 drop CD₃OD, 300 MHz) δ ppm 8.97 (s, 1H), 8.57 (s, 1H), 8.26 (s, 1H), 8.01 (d, J=8.4 Hz, 1H), 7.93 (dd, J=8.4, 1.8 Hz, 1H), 7.61 (s, 1H), 7.44 (d, J=8.4 Hz, 2H), 7.01 (s, 1H), 6.94 (s, 1H), 6.72 (d, J=9 Hz, 2H), 4.22 (t, J=7.2 Hz, 2H), 3.99 (t, J=6.6 Hz, 2H), 2.87 (s, 3H), 2.37-2.34 (m, 2H). ESI-MS m/z 426.2040 (M+H⁺).

Example 51

Synthesis of N-(4-(4-((3-(1H-imidazol-1-yl)propyl)amino)-3-(1,3,4-oxadiazol-2-yl)quinolin-6-yl)phenyl)acetamide (compound 86): Compound 17 (0.08 g, 0.20 mmol) was taken along with N-(4-(4,4,5,5-tetramethyl-1,3,2-dioxaborolan-2-yl)phenyl)acetamide (0.078 g, 0.30 mmol) in 1,4-dioxane (2 mL) and DMF (0.5 mL). 2(M) Na₂CO₃ solution (0.25 mL) and Pd(PPh₃)₄ (0.023 g, 0.02 mmol) were added to the mixture and the reaction was performed according to Example 7. It took 12 hours for the reaction to complete. The residue was purified by silica gel column chromatography, eluting with 10% methanol in CHCl₃ to afford compound 86 (0.025 g, 27%) as a yellow solid. ¹H NMR (CDCl₃+1 drop CD₃OD, 300 MHz) δ ppm 8.97 (s, 1H), 8.56 (s, 1H), 8.23 (s, 1H), 7.97 (d, J=5.7 Hz, 1H), 7.87 (dd, J=8.7, 1.5 Hz, 1H), 7.66 (d, J=8.4 Hz, 2H), 7.48-7.44 (m, 2H), 6.98 (s, 1H), 6.93 (s, 1H), 4.19 (t, J=6.6 Hz, 2H), 3.90 (t, J=6.6 Hz, 2H), 2.39-2.30 (m, 2H), 2.16 (s, 3H). ESI-MS m/z 454.20 (M+H⁺).

Assay Protocols
Plasma Stability Assay:
Assay Procedure

The stock solution of 10 mM of test compound in DMSO was prepared and stored at 4° C. 25 μM stock of test compound was prepared in acetonitrile: water by diluting from 10 mM stock (i.e. 2.5 μL of 10 mM stock solution was added to 997.5 μL of acetonitrile: water (50:50). The frozen plasma was thawed at room temperature and centrifuged at 1400×RCF (relative centrifugal force) 4° C., for 15 minutes. Approximately 90% of the clear supernatant fraction was transferred to a separate tube and was used for the assay.

For 0 min samples, plasma was heat inactivated at 56° C. for 45 min. To 72 μL of heat inactivated plasma, 3 μL of 25 μM test compound was added. A 25 μL aliquot of the mixture was taken and crashed with 200 μL of acetonitrile containing internal standard and further processed along with other time points. For other time point samples, final working stock of 1 μM was prepared by diluting in plasma (i.e. 8 μL of 25 μM acetonitrile:water stock was added to 192 μL of plasma). 200 μL of plasma containing the test compound was incubated for 2 hrs at 37° C. in shaker water bath with gentle shaking. 25 μL aliquot of sample at 0, 15, 30, 60 and 120 min was precipitated immediately with 200 μL of acetonitrile containing internal standard and centrifuged at 4000×RCF, 4° C. for 20 minutes. 150 μL of supernatant was diluted with 150 μL of water and analyzed on LC-MS/MS.

TABLE 2

Plasma stability of the compounds with general formula I at pH 7.4

| Sr. No. | Compound | Mean % remaining at 2 hrs in human Plasma |
|---|---|---|
| 1 | Camptothecin (CPT) | 15.70 |
| 2 | Topotecan | 11.5 |
| 3 | 18 | 93.34 |
| 4 | 20 | 91.32 |
| 5 | 24 | 84.18 |
| 6 | 43 | 83.38 |
| 7 | 30 | 14.62 |
| 8 | 33 | 102.28 |
| 9 | Propantheline (control) | 0.00 |

From the results of table 2, it is inferred that the compounds of Formula I are highly stable in human plasma at pH 7.4.

Solubility Assay
Assay Procedure

5 μL of 20 mM DMSO stock from the stock plate was added to the reaction deep well plate containing 495 μL of pH 7.4 pION buffer (including DMSO control) respectively and the samples were mixed and incubated for 18 hours. The plate was sealed well during the incubation process. The DMSO content in the sample was <1.0%. The concentration in deep well plates was 200 μM. 4 μL of 20 mM stock (including DMSO control) was added to 996 μL of acetonitrile to prepare the working stock plate. 75 μL of working stock was added to 75 μL of blank buffer and read on spectrophotometer as reference plate at 240 nm. At the end of the incubation period, 100 μL of sample from storage plate was vacuum filtered using a filter plate. This step wets the filters and the filtrate was discarded. Another 200 µL of the sample from deep well plate was vacuum filtered in to a new filter collection plate. 75 µL of the filtrate from the filter collection plate was transferred to a UV sample plate. 75 µL of acetonitrile was added to this UV plate. The solution was mixed and the spectrum was read using the UV spectrophotometer at 240 nm. Plates were read on spectramax using SoftMax Pro software version 5.3.

TABLE 3

Aqueous solubility of the compounds with general formula I at pH 7.4

| Sr. No. | Compound | Avg. Solubility (µg/mL) at pH 7.4 |
|---|---|---|
| 1 | CPT | 2.5 |
| 2 | 18 | 30.09 |
| 3 | 20 | 30.19 |
| 4 | 24 | 27.22 |
| 5 | 43 | 28.08 |
| 6 | 30 | 44.03 |
| 7 | 33 | 27.95 |
| 8 | Albendazole (control) | 3.31 |
| 9 | Flurbiprofen (control) | 53.96 |

| Resultof Solubility in µg/mL | Range* |
|---|---|
| <10 µg/mL | Low solubility |
| 10 to 60 µg/mL | Moderate Solubility |
| >60 µg/mL | High solubility |

*(R. Guha, Bioorg Med Chem. 2011, 19, 4127-4134)

Accordingly the compounds of Formula I are moderately soluble in aqueous solution of pH 7.4.

Caco-2 Permeability

Assay Procedure 5 mL of 100 mM sodium pyruvate, 5 mL of 100× non-essential amino acids, 5 mL of penstrep were added to 100 mL of heat inactivated foetal bovine serum to 385 mL of DMEM aseptically and mixed thoroughly. One vial of Hank's balanced salt (Sigma-H1387) was dissolved in 900 mL of milli Q water; adjusted the pH to 7.4 and made up the volume to 1000 mL with the same. The solution was filter sterilized and stored at 4° C. Stock solution of test compound (10 mM) was prepared in DMSO. 10 mM stock was diluted with HBSS Buffer to a final concentration of 10 µM.

Revival of Caco-2 cells: As per SOP-BIO-IA-TCL-013-00

Sub culturing of Caco-2 cells: As per SOP-BIO-TCL-013-00

250 µL of DMEM was added to the basal compartment of 96 well multi-screen Caco-2 plate and seeded 12000 cells/well (0.16×10$^6$ cells/ml) in all the apical wells required and one well with only media as blank without cells, placed the Caco-2 plate in $CO_2$ incubator at 37° C. for proliferation of cells.

On the day of assay, medium was removed and washed twice with HBSS Buffer and incubated with HBSS buffer for 30 min in an incubator and wells with TEER values >230 ohm·cm$^2$ were selected for the incubation. 75 µL of test compound was added to apical wells and 250 µL of HBSS buffer with 2% BSA was added to basal wells. 25 µL of basal samples was collected at 120 min and processed as stated below. 250 µL of test compound was added to basal wells and 75 µL of HBSS buffer with 2% BSA was added to apical wells. 25 µL of apical samples was collected at 120 min and processed as stated below.

Single point calibration curve in HBSS buffer with 2% BSA was used. Donor samples were diluted 1:1 with HBSS containing 2% BSA and receiver samples were diluted with 1.1 HBSS buffer and precipitated with 200 µL of acetonitrile containing internal standard and vortexed for 5 min @ 1000 rpm, centrifuged at 4000 rpm for 10 min. Finally 100 µL of supernatant was diluted with 200 µL of water and submitted for LC-MS/MS analysis.

TABLE 4

In vitro evaluation of apparent permeability using 21 day culture of Caco-2 cell monolayer

| Sr. No. | Compound | $P_{app}$ ($10^{-6}$ cm/sec) Apical to Basal | Basal to Apical | Efflux Ratio | A to B % Recovery | B to A % Recovery |
|---|---|---|---|---|---|---|
|  | CPT* | 10.5 | 35.8 | 3.4 |  |  |
| 1 | 18 | 7.42 | 11.55 | 1.60 | 33.23 | 44.16 |
| 2 | 20 | 0.63 | 44.22 | 70.05 | 72.67 | 91.66 |
| 3 | 24 | 6.47 | 27.37 | 4.54 | 77.28 | 77.72 |
| 4 | 43 | 10.89 | 10.98 | 1.02 | 42.65 | 58.53 |
| 5 | 30 | 0.95 | 38.30 | 40.05 | 84.85 | 74.19 |
| 6 | 33 | 7.89 | 31.53 | 4.01 | 83.93 | 91.99 |
| 7 | Propranolol | 19.10 | 13.30 | 0.72 | 68.02 | 72.72 |
| 8 | Atenolol | 0.32 | 0.38 | 1.20 | 86.53 | 88.29 |

*(A. K. Lalloo, BMC Medicine, 2004, 2,16)

Lipophilicity Assay

Assay Procedure 1.56 g $NaH_2PO_4 \cdot 2H_2O$ was dissolved in 0.5 L water in a 1 L beaker. After adjusting pH to 7.4 using NaOH solution, the volume was made up to 1 L. Equal volumes of sodium phosphate buffer (10 mM, pH 7.4) and n-octanol were added to a separation funnel and mixed thoroughly by shaking and inverting the funnel several times. The two layers were allowed to separate for 2 days and then dispensed in two separate glass bottles. 10 mM stock solution was prepared in 100% DMSO and stored at 4° C. 500 µL of organic phase (1-octanol) was added to each well of a 2 mL deep well plate, followed by 500 µL of buffer and 15 µL of test substance was added. The plate was vortexed for 1 hr on a plate shaker at 1200 rpm. After incubation, the samples were allowed to equilibrate for 20 min and then centrifuged at 4000 rpm for 30 min for complete phase separation and analysed by LC-UV.

Calculations

Log D=Log (area of octanol/area of buffer)

Mean, SD and % CV for each set of triplicates were calculated

TABLE 5

Log D values of the compounds at physiological pH 7.4

| Sr. No. | Compound | Log D @ pH 7.40 | | |
|---|---|---|---|---|
| | | Mean | SD | % CV |
| 1 | CPT | 1.74* | — | — |
| 2 | 18 | 2.48 | 0.04 | 1.82 |
| 3 | 20 | 2.56 | 0.03 | 1.35 |
| 4 | 24 | 3.51 | 0.01 | 0.01 |
| 5 | 43 | 3.26 | 0.01 | 0.01 |
| 6 | 30 | 3.54 | 0.02 | 0.02 |
| 7 | 33 | 2.79 | 0.00 | 0.00 |
| 8 | Ketoconazole | 3.03 | 0.02 | 0.74 |
| 9 | Metoprolol | −0.29 | 0.00 | 1.34 |
| 10 | Propranolol | 1.16 | 0.01 | 0.5 |

*Log P

Gel Based Plasmid DNA Relaxation Assay:

Human ToPI Inhibition in Plasmid DNA Relaxation Assays with Recombinant TopI (In Vitro) or MCF7 Cell Lysates (Ex Vivo)

Figure 2:
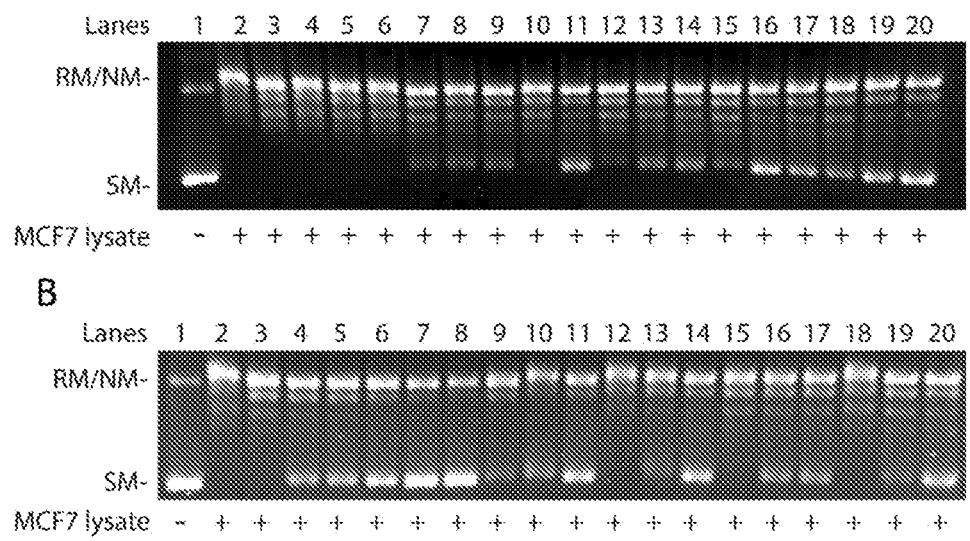
FIG. 2: depicts the inhibitory activity of the bicyclic compounds of Formula I: (A) test Compounds 26, 18, 20, 50, 24, 30 on endogenous TopI activity from carcinogenic cellular extracts of MCF7 cells (each reaction volume contains 0.1 µg protein). Lanes 1:pBS (SK$^+$) DNA (0.3 µg); lane 2: same as lane 1 but DNA was incubated with MCF7 cell lysates; lanes 3-20: same as lane 2 but MCF7 whole lysates were simultaneously incubated with 0.2, 0.3 and 0.5 µM compound 26 (lane 3-5), compound 18 (lane 6-8), compound 20 (lane 9-11), compound 50 (lane 12-14), compound 30 (lane 15-17), compound 24 (lane 18-20) at 37° C. for 30 minutes. Positions of supercoiled monomer (SM), relaxed and nicked monomer (RM/NM) are indicated. (B) Test compounds 68, 15, 17, 33, 24, 18 on endogenous TopI activity from carcinogenic cellular extracts of MCF7 cells. Lanes 1: pBS (SK$^+$) DNA (0.3 µg); lane 2: same as lane 1 but DNA was incubated with MCF7 cell lysates; lanes 3-20: same as lane 2 but MCF7 whole lysates were simultaneously incubated with 0.2, 0.3 and 0.5 µM compound 68 (lane 3-5), compound 15 (lane 6-8), compound 17 (lane 9-11), compound 33 (lane 12-14), compound 24 (lane 15-17), compound 18 (lane 18-20) at 37° C. for 30 minutes. Positions of supercoiled monomer (SM), relaxed and nicked monomer (RM/NM) are indicated.

Both recombinant TopI enzyme and endogenous TopI from the whole cell extracts of human breast adenocarcinoma (MCF7) cell were used to determine the specificity of the compounds of formula I below and as shown in FIG. 1. Relaxation of supercoiled pBSSK($^+$) DNA with recombinant human TopI (HTopI) at a molar ratio of 3:1 at 37° C. for 30 minutes was performed When recombinant TopI and compound 18 were added simultaneously in the plasmid DNA relaxation assays, 85-90% inhibition of TopI was observed at 0.1 µM concentration of compound 18 (FIG. 1).

cellular extracts were utilized as a source of TopI (ex vivo) in plasmid DNA relaxation assays. TopI enzyme in the extract is conserved in its native structure among a plethora of other cellular proteins. When the cellular extracts were incubated with the test compounds the ex vivo relaxation inhibition assays efficiently inhibited TopI activity as shown in FIG. 2 (S. K. Das, J. Med. Chem. 2018, 61, 804-817; B. Kundu, J. Med. Chem. 2019, 62, 3428-3446).

TABLE 6

IC$_{50}$ values of the compounds with general formula I composition of the invention.

| CODE | Compound No | STRUCTURE | In vitro IC$_{50}$ (µM) | Ex vivo IC$_{50}$ (µM) |
|---|---|---|---|---|
| Camptothecin | | 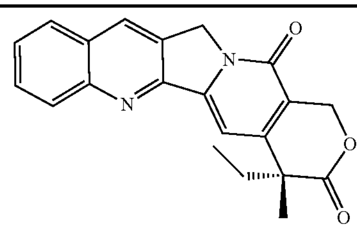 | 0.025 | 2.5 |
| Topotecan | | 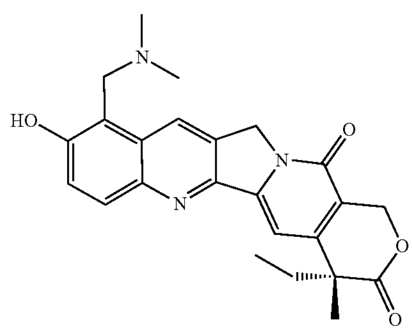 [SMILES: CC[C@@]1(C)C(=O)OCc2c1cc1n(c2=O)Cc2cc3c(CN(C)C)c(O)ccc3nc2-1] | 0.021 | 1.8 |
| TBK-2-129 | 33 | 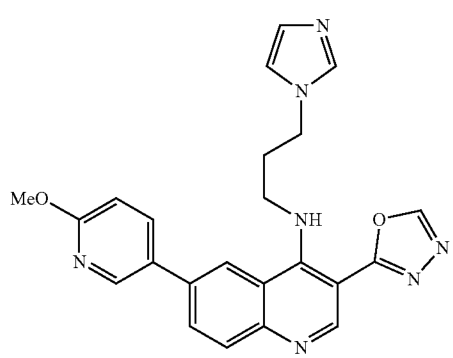 [SMILES: COc1ccc(-c2ccc3ncc(-c4nnco4)c(NCCCn4ccnc4)c3c2)cn1] | 0.017 | 0.625 |

TABLE 6-continued

IC$_{50}$ values of the compounds with general formula I composition of the invention.

| CODE | Compound No | STRUCTURE | In vitro IC$_{50}$ (µM) | Ex vivo IC$_{50}$ (µM) |
|---|---|---|---|---|
| TBK-1-125 | 24 | 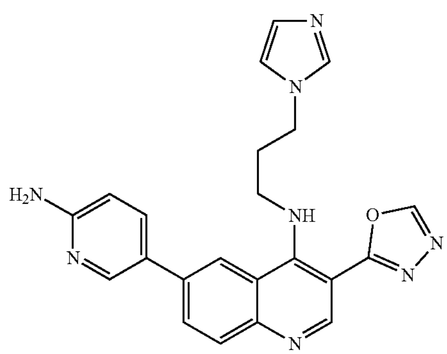 [SMILES: Nc1ccc(-c2ccc3ncc(-c4nnco4)c(NCCCn4ccnc4)c3c2)cn1] | 0.021 | 1.83 |
| TBK-1-97 | 20 | 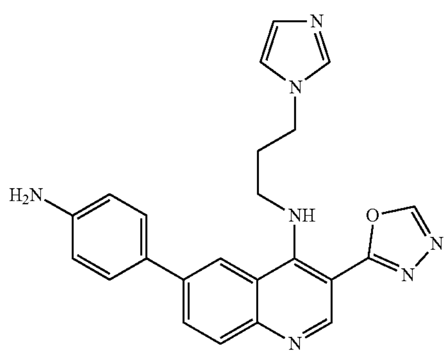 [SMILES: Nc1ccc(-c2ccc3ncc(-c4nnco4)c(NCCCn4ccnc4)c3c2)cc1] | 0.024 | 2.25 |
| TBK-1-53 | 18 | 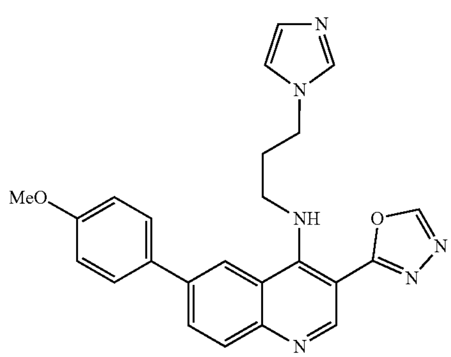 [SMILES: COc1ccc(-c2ccc3ncc(-c4nnco4)c(NCCCn4ccnc4)c3c2)cc1] | 0.029 | 2.74 |
| TBK-2-19 | 30 | 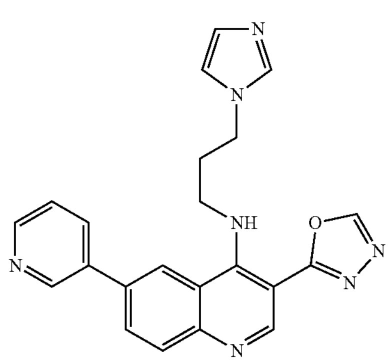 [SMILES: c1cncc(-c2ccc3ncc(-c4nnco4)c(NCCCn4ccnc4)c3c2)c1] | 0.397 | 1.25 |

TABLE 6-continued
IC$_{50}$ values of the compounds with general formula I composition of the invention.
| CODE | Compound No | STRUCTURE | In vitro IC$_{50}$ (μM) | Ex vivo IC$_{50}$ (μM) |
|---|---|---|---|---|
| TBK-1-157 | 42 | 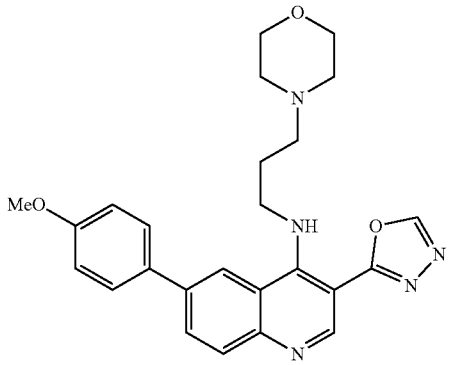 [SMILES: COc1ccc(-c2ccc3ncc(-c4nnco4)c(NCCCN4CCOCC4)c3c2)cc1] | 1.79 | 2.51 |
| TBK-2-17 | 29 | 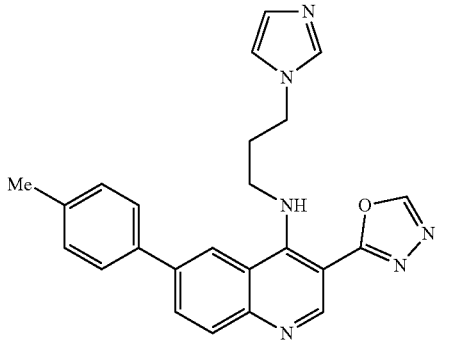 [SMILES: Cc1ccc(-c2ccc3ncc(-c4nnco4)c(NCCCn4ccnc4)c3c2)cc1] | 1.06 | 3.75 |
| TBK-1-145 | 28 | 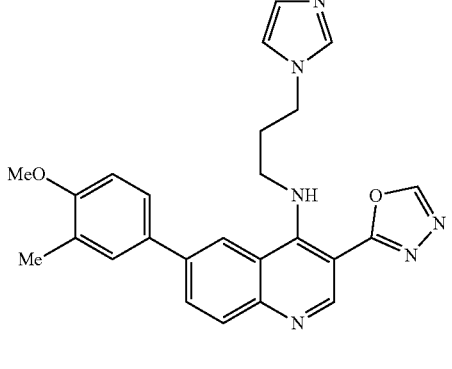 | 2.36 | 3.0 |
| TBK-1-137 | 73 | 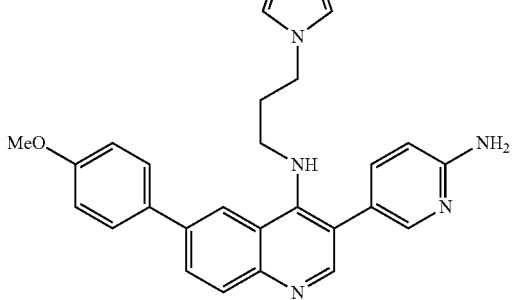 | 5.24 | 9.0 |

TABLE 6-continued
IC50 values of the compounds with general formula I composition of the invention.
| CODE | Compound No | STRUCTURE | In vitro IC$_{50}$ (μM) | Ex vivo IC$_{50}$ (μM) |
|---|---|---|---|---|
| TBK-3-11 | 82 | 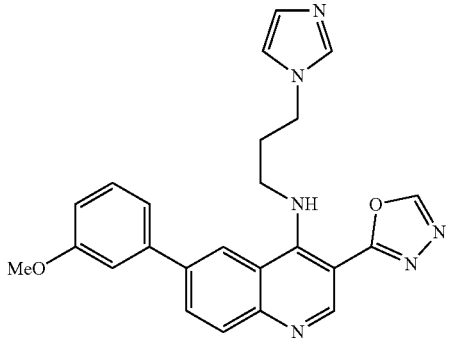 [SMILES: COc1cccc(-c2ccc3ncc(-c4nnco4)c(NCCCn4ccnc4)c3c2)c1] | 1.05 | 4.11 |
| TBK-1-39 | 9 | 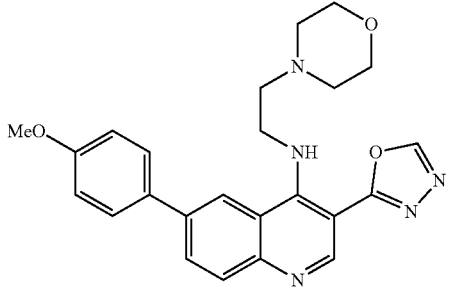 [SMILES: COc1ccc(-c2ccc3ncc(-c4nnco4)c(NCCN4CCOCC4)c3c2)cc1] | 45% inhibition at 10 μM | NA |
| TBK-1-71 | 14 | 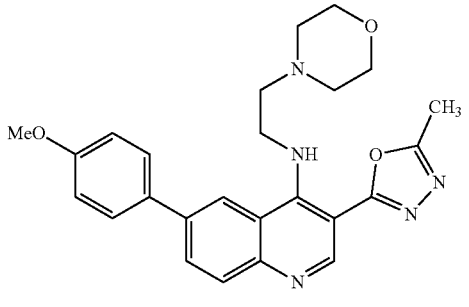 [SMILES: COc1ccc(-c2ccc3ncc(-c4nnc(C)o4)c(NCCN4CCOCC4)c3c2)cc1] | 50% inhibition at 10 μM | NA |
| TBK-1-139 | 27 | 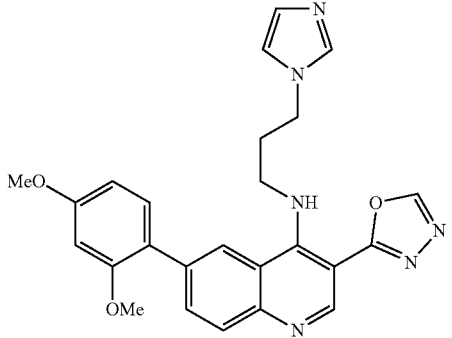 | 45% inhibition at 10 μM | NA |

TABLE 6-continued

IC$_{50}$ values of the compounds with general formula I composition of the invention.

| CODE | Compound No | STRUCTURE | In vitro IC$_{50}$ (μM) | Ex vivo IC$_{50}$ (μM) |
|---|---|---|---|---|
| TBK-1-151 | 52 | 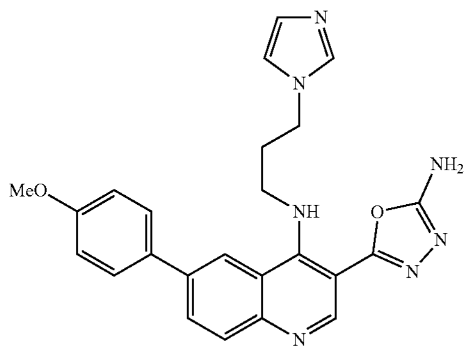 | 45% inhibition at 10 μM | NA |
| TBK-2-13 | 54 | 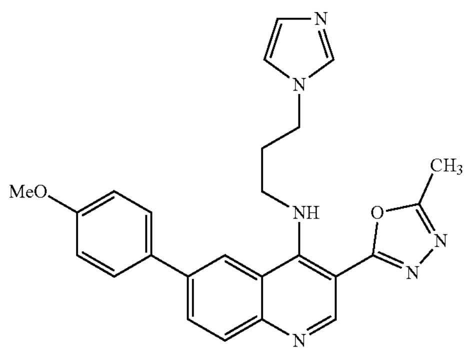 [SMILES: COc1ccc(-c2ccc3ncc(-c4nnc(N)o4)c(NCCCn4ccnc4)c3c2)cc1] | 55% inhibition at 10 μM | NA |
| TBK-2-89 | 78 | 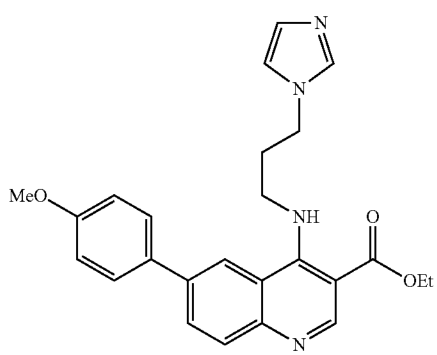 [SMILES: CCOC(=O)c1cnc2ccc(-c3ccc(OC)cc3)cc2c1NCCCn1ccnc1] | 35% inhibition at 10 μM | NA |
| TBK-1-45 | 17 | 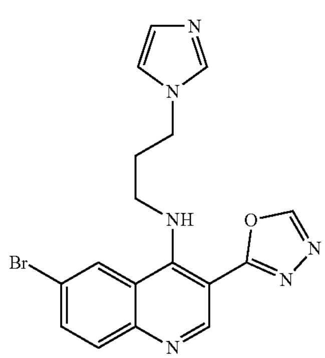 [SMILES: Brc1ccc2ncc(-c3nnco3)c(NCCCn3ccnc3)c2c1] | 30% inhibition at 10 μM | NA |

TABLE 6-continued

IC$_{50}$ values of the compounds with general formula I composition of the invention.

| CODE | Compound No | STRUCTURE | In vitro IC$_{50}$ (µM) | Ex vivo IC$_{50}$ (µM) |
|---|---|---|---|---|
| TBK-2-15 | 77 | (structure) | 20% Inhibition at 10 µM | NA |
| TBK-1-19 | 15 | (structure) | 30% inhibition at 10 µM | NA |

DNA Cleavage Assay

Cleavage reaction and electrophoresis in agarose gel were performed as described in B. Kundu, J. Med. Chem. 2019, 62, 3428-3446. Lane 1 comprises 50 fmol of pBluescript (SK$^+$) supercoiled DNA. Lanes 2-9 are same as lane 1 but incubated with equal amounts (100 fmol) of HTopI at the indicated concentration of CPT or compound 24 or only DMSO. Positions of supercoiled substrate (Form I) and nicked monomers (Form II) are indicated in FIG. 3.

The mechanism of TopI inhibition with compound 24 in the plasmid DNA cleavage assays was investigated. Closed circular DNA (form I) get converted to nicked circular DNA (form II) by TopI in the presence of compound 24 and CPT and are referred to as "cleavage complex" (FIG. 3). FIG. 3 shows that compound 24 is capable of stabilising TopIcc formation like CPT, suggesting that compound 24 acts as a TopI poison.

Figure 4:
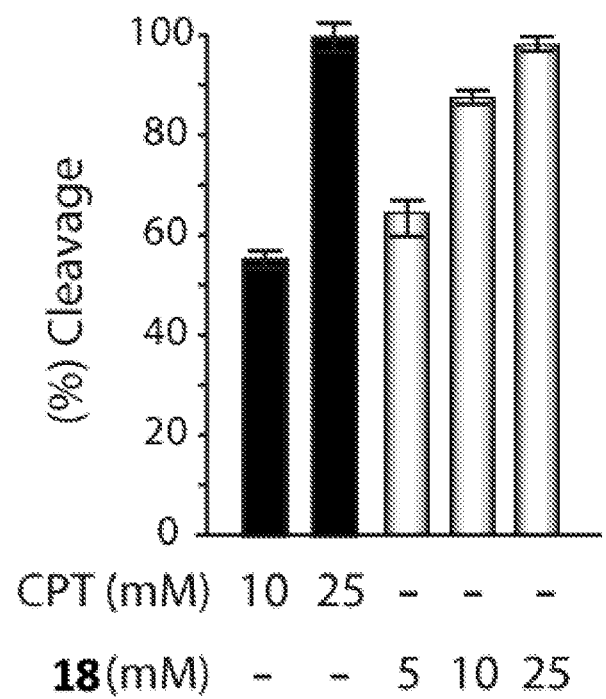
FIG. 4: quantitative measurement of formation of cleavage complex (%) by compound 18 and CPT by supercoiled DNA is depicted.

FIG. 4 shows a comparison between the extent or rate of TopI-DNA cleavage complex formation (% cleavage) with compound 18 and CPT at indicated concentration. Similar trapping of topoisomerase I-DNA cleavage complexes (Top-I-DNA cleavage complexes, TopIccs) by CPT and 18 is observed by FIG. 4.

Figure 3:
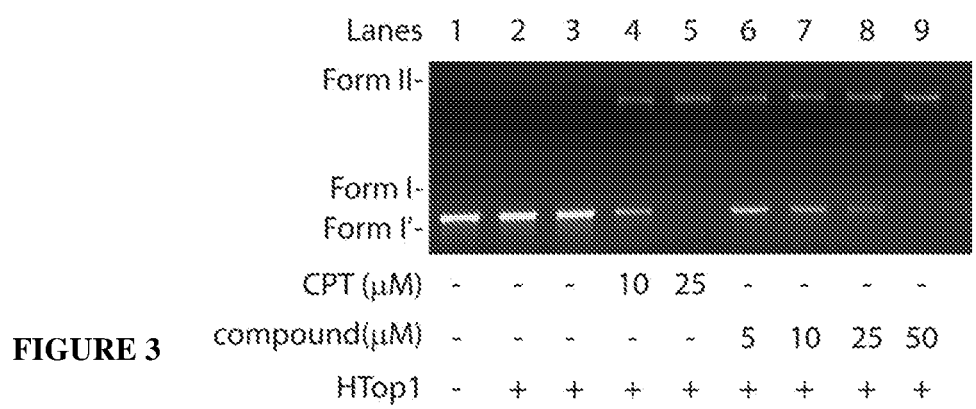
FIG. 3: depicts test compound 24 mediated trapping of human TopI-plasmid DNA cleavage complexes in the presence of SDS-K$^+$. Lane 1: 50 fmol of pBluescript (SK$^+$) supercoiled DNA. Lanes 2-9: same as lane 1 but incubated with equal amounts (100 fmol) of HTopI at the indicated concentration of CPT or compound 24 or only DMSO. Positions of supercoiled substrate (Form I) and nicked monomers (Form II) are indicated.

From FIGS. 3 and 4, it can be inferred that compound 18 and 24 stabilise TopI cleavage complexes and inhibit the religation activity with similar efficacy as that of CPT. Therefore Compound 18 (FIG. 4) and 24 (FIG. 3) acts as a poison by stabilizing human TopI-DNA cleavage complexes.

Figure 5:
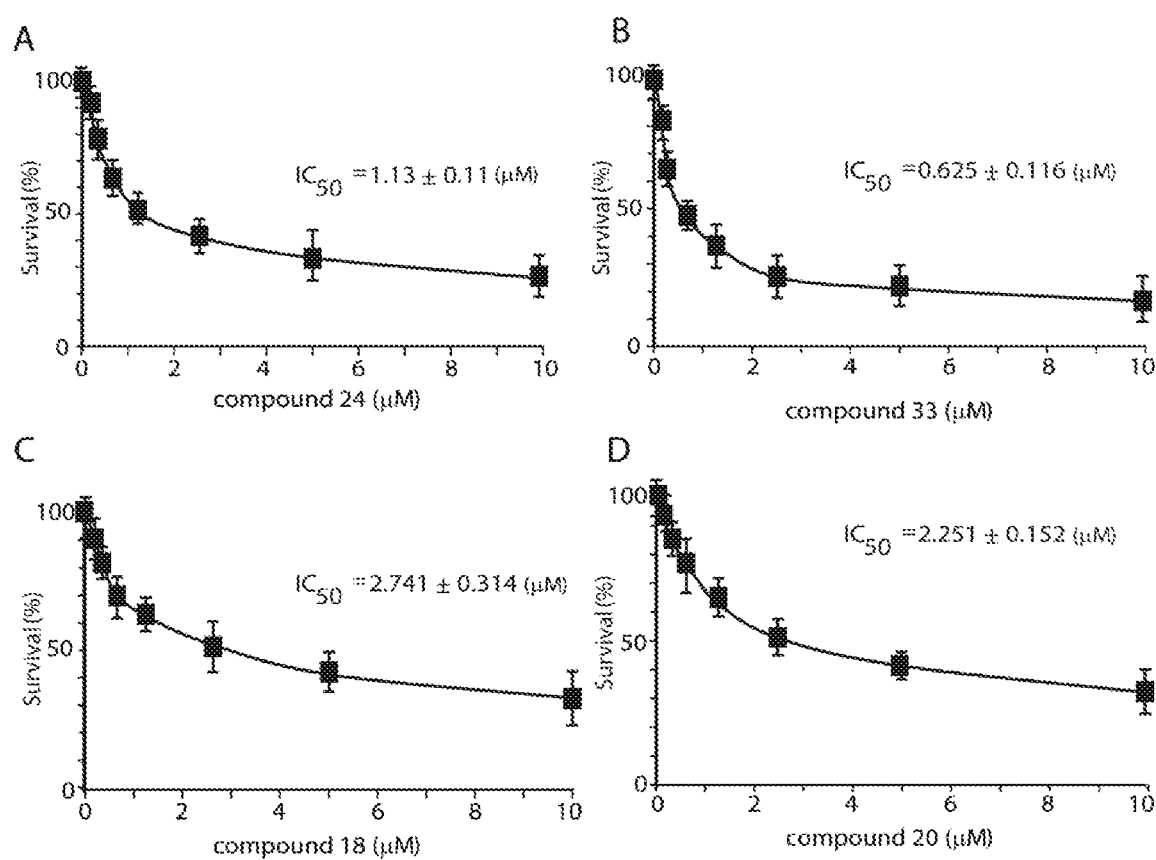
FIG. 5: depicts the graphical representation of % survival of MCF7 cells in cytotoxicity assays (MTT assays) of test compound 24, 33, 18, 20 in human breast adenocarcinoma cell lines (MCF7), with variable concentrations of compound.

Cytotoxicity Assay:

The compound 18, 24, 33 and 20 were evaluated for its cytotoxicity in different cell lines such as human breast adenocarcinoma cell lines (MCF7) (FIG. 5), human cervical cancer cell lines (HeLa), human colon carcinoma cell lines (HCT116), human ovarian adenocarcinoma cell lines (NIH: OVCAR-3), as well as noncancerous human embryonic kidney (HEK293) cells with variable concentrations of the aforesaid compounds and compared with camptothecin (CPT) (B. Kundu, J. Med. Chem. 2019, 62, 3428-3446).

TABLE 7

Cytotoxicity of compound 18 in different cell lines

| Cell lines | IC50 of CPT(µM) | IC50 of 18 (µM) |
|---|---|---|
| MCF7 | 2.5 ± 0.36 | 2.74 ± 0.31 |
| HCT116 | — | 2.34 ± 0.86 |
| NIH:OVCAR-3 | — | 2.35 ± 0.78 |
| HEK293 | 8.75 ± 0.63 | 8.34 ± 0.96 |
| TDP1+/+ | 2.80 ± 0.47 | 2.91 ± 0.23 |
| TDP1−/− | 1.57 ± 0.21 | 1.02 ± 0.08 |
| HeLa | — | 2.61 ± 0.86 |

The results of table 7 show that compound 18 revealed cytotoxicity in cancerous cells including MCF7 (IC50: 2.74 µM), HeLa (IC50: 2.61 µM), HCT116 (IC50: 2.34 µM), and NIH:OVCAR-3 (IC50: 2.35 µM) cells compared to the noncancerous cells such as HEK293 (IC50: 8.34 µM). The cytotoxicity assays with TDP1−/− (IC50: 1.02 µM) were also performed, which are hypersensitive toward TopI poisons and TDP1+/+ MEFs (IC50: 2.91 µM) cells in the presence of compound 18. The anticancer activity data confirm that compound 18 acts as a potent TopI poison by trapping human Top I-DNA cleavage complexes (TopIcc). The graphical representation (FIG. 5) of percentage survival (%) of MCF7 cells was plotted as a function of each compound 18, 24, 33 and 20 at different concentrations. The percent inhibition of viability for each concentration of compound was calculated with respect to the control and IC$_{50}$ (PM) values were estimated. Each point corresponds to the mean±S.D of at least three experiments in duplicates. Error bars represent SD (n=3).

Figure 6:
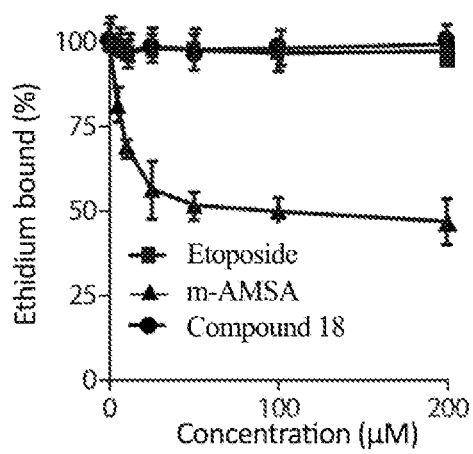
FIG. 6: depicts the Ethidium bromide (EtBr) bound (%) with varying concentration of Etoposide, m-AMSA and test compound 18 in EtBr displacement assay (fluorescence-based).

Ethidium Bromide (EtBr) Displacement Assays:

EtBr displacement assays were carried in order to investigate the ability of compound 18 to intercalate into DNA. All samples contained 1 µM EtBr and 5 nM calf thymus (CT) DNA. The EtBr bound (%) fluorescence is measured with increasing concentration (0-200 PM) of compound 18, m-ASA (intercalative agent) and etoposide. It is apparent in FIG. 6 that the intercalative drug m-AMSA has the capability to dislodge the bound fluorophore (EtBr) at 50 μM concentration. However, non intercalative drug such as etoposide was unable to displace EtBr. Under similar condition, compound 18 induces no displacement of fluorophore even at high concentration (200 μM) compared with the very low $IC_{50}$ (29 nM) of TopI inhibition. FIG. 6 suggest that compound 18 is not a DNA intercalator.

Mutation Assay

Figure 7:
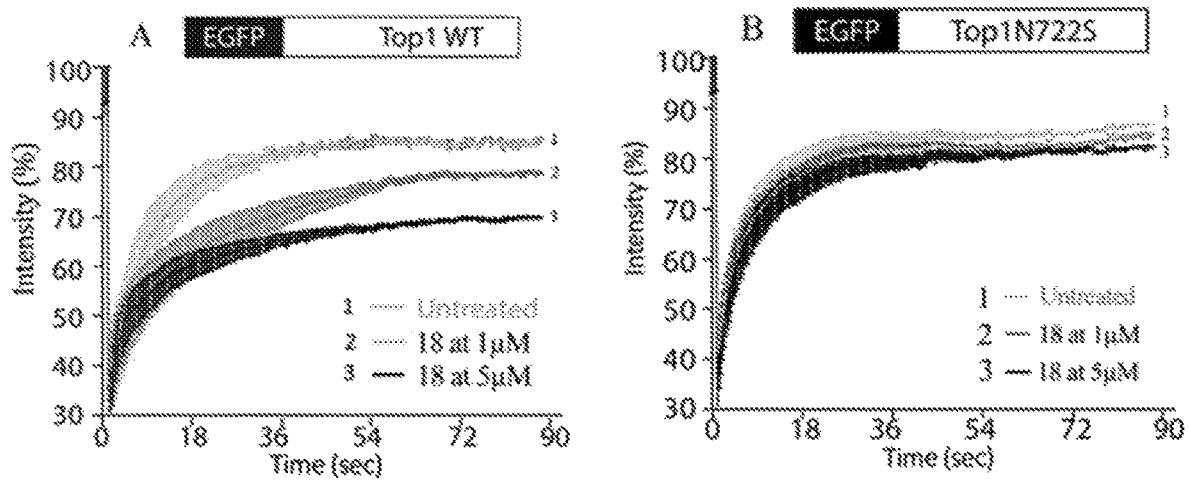
FIG. 7: depicts the direct evidence of test compound 18 mediated stabilization of the TopI-DNA cleavage complex in live MCF7 cells.

Fluoresence recovery after photobleaching (FRAP) technology has been used here to obtain direct evidence for compound 18-mediated trapping of TopIcc (FIG. 7A) in live MCF7 cells. Quantification of fluorescence return into the bleached areas was performed on treatment with specific concentration of compound 18 with transiently expressed in MCF7 cells were analysed by live cell spinning disk confocal microscopy, and fluorescence recovery after photobleaching (FRAP) experiments with the enhanced green fluorescent protein EGFP-TopIWT (A) and with TopIN722S (B).

We expressed a green fluorescent-tagged human TopI (EGFP-TopI) in MCF7 cells and the nuclear mobility of TopI has been tested under live cell spinning disk confocal microscopy. It is observed that FRAP recovery of EGFP-TopI was fast (~85-90%) in the absence of compound 18, suggesting a large mobile population and a smaller (~10-15%) immobile population of EGFP-TopI. These data prove that TopI is mostly mobile and binds transiently with the DNA (reversible TopIcc). In the presence of compound 18, the fluorescence recovery of EGFP-TopI was markedly impeded (~55-65%) with increasing concentration of compound 18 (FIG. 4A, compound 18; 1 and 5 μM). All these data suggest that compound 18 traps TopIcc on DNA in live cells like CPT which leads to a subsequent increase in bound immobile fraction of EGFP-TopI. This is consistent with 18-mediated stabilization of TopIcc in the in vitro cleavage assays. In order to investigate this possibility, FRAP analysis of compound 18 to trap mutant TopI at residue Asn722 (EGFP-TopIN722S) in live cells was carried out(FIG. 7B). The results suggest that the FRAP recovery of EGFP-TopIN722S was unaffected in the presence of increasing concentration of 18 and was similar to no drug treatment condition. This data suggests that compound 18 failed to trap TopIcc when Asn722 is mutated to Serine, signifying the importance of N722 residue for the Top I inhibition and depicting the mechanism of action.

Figure 8:
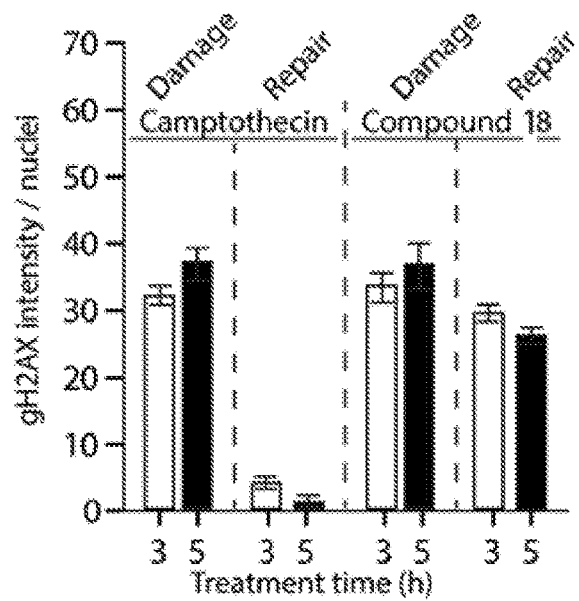
FIG. 8: depicts quantification of comparative ability of CPT and test compound 18 to form DSBs by measuring TH2AX intensity per nucleus by varying treatment time.

It is inferred that TopI cleavage complexes being trapped by compound 18 in live MCF7 cells (FIG. 7):

γH2AX Assay:

Quantification of comparative ability of CPT and 18 to form DSBs was quantified after 3 hours and 5 hours by measuring γH2AX intensity per nucleus after treatment and after the removal of 18 or CPT was obtained from immunofluorescence confocal microscopy. Figure shows generation of more persistent and less reversible DSBs compared to CPT. As it is already discussed, compound 18 stabilizes TopIcc in vitro (FIG. 3) and in live cells (FIG. 7). the accumulation and disappearance of DSBs in MCF7 cells treated with compound 18 was measured by TH2AX foci formation under confocal microscopy (FIG. 8). TH2AX is a well-defined marker for TopI-mediated DSBs. Under similar condition, we detected a time-dependent increase in TH2AX foci formation in cells treated with compound 18 as well as CPT for 3 and 5 hours. The result shows that both compound 18 and CPT generate similar levels of DSBs at indicated time periods in MCF7 cells (FIG. 8). But CPT-induced TH2AX have a short half-life. FIG. 8 shows faster disappearance of TH2AX foci after washing out CPT from media at indicated time periods. (T. Furuta. J. Biol. Chem. 2003, 278, 20303-20312). It is inferred that TopIccs formed by compound 18 lead to the formation of persistent and less reversible DNA double-strand breaks (DSBs) detected by TH2AX staining.

Advantages of the Invention

The synthesized new compounds with general formula I of the present invention have several advantages.

1. The compounds with general formula I show potent inhibitory activity on Human Topoisomerase I and also show cytotoxicity in Breast Cancer cells and therefore may act as novel anticancer therapeutics.
2. The compounds with general formula I act as anticancer agent by inhibition Topoisomerase I enzyme like the camptothecin.
3. The compounds with general formula I with $R_1$, $R_2$ and $R_3$ substituted aromatic ring together show better or comparable inhibitory activity in in-vivo and ex-vivo assay system than camptothecin.
4. The compounds with general formula I are stable drug candidates which possess the ability to increase the stability of the drug-DNA-TopI ternary complex that eventually results in cancer cell death to achieve clinical anticancer activity.
5. The compounds with general formula I generate more persistent and less reversible TopIcc-induced double strand breaks as compared to CPT in γH2AX assay.
6. The compounds with general formula I are not a DNA intercalator.
7. The compounds with general formula I are non-camptothecin inhibitors will help to develop more effective chemotherapeutics for this deadliest disease.
8. Compounds with formula I described in claim 1 or in acceptable salt can be useful to treat any of a variety of conditions where inhibition of topoisomerase I enzyme is important.
9. The plasma stability of the compounds with general formula I shows that they are highly stable at pH 7.4 in plasma.
10. The aqueous solubility of the compounds with general formula I show moderate solubility at pH 7.4.
11. The compounds with general formula I show good Caco-2 permeability and acceptable lipophilicity (Log D at pH 7.4) profile.

We claim:
1. A compound of Formula I or salts thereof,

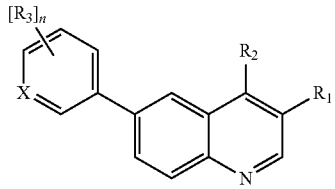

Formula I wherein:
$R_1$ is a substituted aromatic heterocyclic group selected from the group consisting of oxadiazole, pyridyl, amino pyridyl, and furyl, wherein the aromatic heterocyclic group is substituted with —CH$_3$ or —NH$_2$;

R$_2$ is a water soluble or hydrophilic functional group —NR$_5$R$_6$;

R$_5$ and R$_6$ are either same or different selected from hydrogen atom, a substituted C$_1$-C$_6$ alkyl chain bearing nitrogen containing aromatic heterocyclic group, or a substituted C$_1$-C$_6$ alkyl chain bearing nitrogen containing aliphatic heterocyclic group;

R$_3$ is selected from hydrogen, halogen, hydroxy, cyano, C$_1$-C$_6$ alkyl, C$_1$-C$_6$ haloalkyl, C$_1$-C$_6$ alkoxy, C$_1$-C$_6$ haloalkoxy, amino, alkylamino, acyl amino, or carbamate;

X is CH; and n is 0-3.

2. The compound as claimed in claim 1, wherein the compound is selected from:

6-(4-methoxyphenyl)-N-(2-morpholinoethyl)-3-(1,3,4-oxadiazol-2-yl)quinolin-4-amine (9);
6-(4-methoxyphenyl)-3-(5-methyl-1,3,4-oxadiazol-2-yl)-N-(2-morpholinoethyl)quinolin-4-amine (14);
N-(3-(1H-imidazol-1-yl)propyl)-6-(4-methoxyphenyl)-3-(1,3,4-oxadiazol-2-yl)quinolin-4-amine (18);
N-(3-(1H-imidazol-1-yl)propyl)-6-(3,4-dimethoxyphenyl)-3-(1,3,4-oxadiazol-2-yl)quinolin-4-amine (19);
N-(3-(1H-imidazol-1-yl)propyl)-6-(4-aminophenyl)-3-(1,3,4-oxadiazol-2-yl)quinolin-4-amine (20);
4-(4-((3-(1H-imidazol-1-yl)propyl)amino)-3-(1,3,4-oxadiazol-2-yl)quinolin-6-yl)benzonitrile (21);
4-(4-((3-(1H-imidazol-1-yl)propyl)amino)-3-(1,3,4-oxadiazol-2-yl)quinolin-6-yl)phenol (22);
N-(3-(1H-imidazol-1-yl)propyl)-6-(4-methoxy-3-methylphenyl)-3-(1,3,4-oxadiazol-2-yl)quinolin-4-amine (28);
N-(3-(1H-imidazol-1-yl)propyl)-3-(1,3,4-oxadiazol-2-yl)-6-(p-tolyl)quinolin-4-amine (29);
N-(3-(1H-imidazol-1-yl)propyl)-6-(4-methoxy-2-methylphenyl)-3-(1,3,4-oxadiazol-2-yl)quinolin-4-amine (31);
N-(3-(1H-imidazol-1-yl)propyl)-6-(4-methoxy-2,6-dimethylphenyl)-3-(1,3,4-oxadiazol-2-yl)quinolin-4-amine (32);
N-(3-(1H-imidazol-1-yl)propyl)-6-(4-ethoxyphenyl)-3-(1,3,4-oxadiazol-2-yl)quinolin-4-amine (34);
N-(3-(1H-imidazol-1-yl)propyl)-6-(4-ethylphenyl)-3-(1,3,4-oxadiazol-2-yl)quinolin-4-amine (35);
N-(3-(1H-imidazol-1-yl)propyl)-6-(4-isopropoxyphenyl)-3-(1,3,4-oxadiazol-2-yl)quinolin-4-amine (36);
N-(3-(1H-imidazol-1-yl)propyl)-6-(4-isopropylphenyl)-3-(1,3,4-oxadiazol-2-yl)quinolin-4-amine (37);
6-(4-methoxyphenyl)-N-(3-morpholinopropyl)-3-(1,3,4-oxadiazol-2-yl)quinolin-4-amine (43);
N-(3-morpholinopropyl)-3-(1,3,4-oxadiazol-2-yl)-6-(p-tolyl)quinolin-4-amine (44a);
6-(3,4-dimethoxyphenyl)-N-(3-morpholinopropyl)-3-(1,3,4-oxadiazol-2-yl)quinolin-4-amine (45a);
N-(2-(1H-imidazol-1-yl)ethyl)-6-(4-methoxyphenyl)-3-(1,3,4-oxadiazol-2-yl)quinolin-4-amine (50);
5-(4-((3-(1H-imidazol-1-yl)propyl)amino)-6-(4-methoxyphenyl)quinolin-3-yl)-1,3,4-oxadiazol-2-amine (52);
N-(3-(1H-imidazol-1-yl)propyl)-6-(4-methoxyphenyl)-3-(5-methyl-1,3,4-oxadiazol-2-yl)quinolin-4-amine (54);
N-(3-(1H-pyrrol-1-yl)propyl)-6-(4-methoxyphenyl)-3-(1,3,4-oxadiazol-2-yl)quinolin-4-amine (58);
6-(4-methoxyphenyl)-3-(1,3,4-oxadiazol-2-yl)-N-(3-(pyrrolidin-1-yl)propyl)quinolin-4-amine (62);

N-(3-(1H-imidazol-1-yl)propyl)-3-(furan-2-yl)-6-(4-methoxyphenyl)quinolin-4-amine (70);
N-(3-(1H-imidazol-1-yl)propyl)-3-(6-aminopyridin-3-yl)-6-(4-methoxyphenyl)quinolin-4-amine (73);
N-(3-(1H-imidazol-1-yl)propyl)-3-(1,3,4-oxadiazol-2-yl)-6-(4-(trifluoromethyl)phenyl)quinolin-4-amine (79);
N-(3-(1H-imidazol-1-yl)propyl)-6-(4-(dimethylamino)phenyl)-3-(1,3,4-oxadiazol-2-yl)quinolin-4-amine (80);
N-(3-(1H-imidazol-1-yl)propyl)-3-(1,3,4-oxadiazol-2-yl)-6-(4-(trifluoromethoxy)phenyl)quinolin-4-amine (81);
N-(3-(1H-imidazol-1-yl)propyl)-6-(3-methoxyphenyl)-3-(1,3,4-oxadiazol-2-yl)quinolin-4-amine (82);
N-(3-(1H-imidazol-1-yl)propyl)-6-(2-methoxyphenyl)-3-(1,3,4-oxadiazol-2-yl)quinolin-4-amine (83);
tert-butyl (4-(4-((3-(1H-imidazol-1-yl)propyl)amino)-3-(1,3,4-oxadiazol-2-yl)quinolin-6-yl)phenyl)(methyl)carbamate (84);
N-(3-(1H-imidazol-1-yl)propyl)-6-(4-(methylamino)phenyl)-3-(1,3,4-oxadiazol-2-yl)quinolin-4-amine (85); and
N-(4-(4-((3-(1H-imidazol-1-yl)propyl)amino)-3-(1,3,4-oxadiazol-2-yl)quinolin-6-yl)phenyl)acetamide (86).

3. A process of preparation of the compound of Formula I as claimed in claim 1 comprising reacting a compound of Formula II

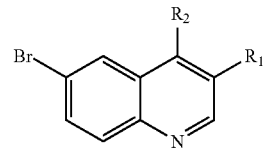

Formula II with a boronic acid of Formula V or Formula VI

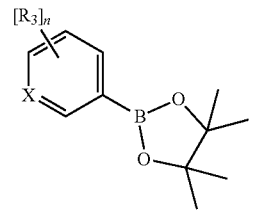

Formula V or

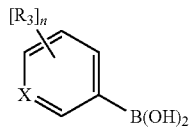

Formula VI in presence of a 2(M) sodium carbonate solution and a tetrakis(triphenylphosphine)palladium(0) catalyst in a solvent to obtain the compound of Formula I,

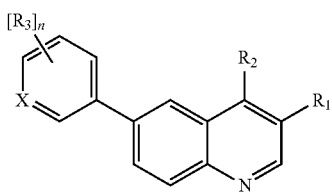

Formula I wherein R₁-R₃, n and X are as defined in claim 1.

4. The process of preparation of compound of Formula I as claimed in claim 3, wherein R₁ of the Formula I is

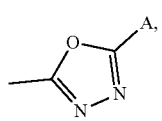

the process comprising:
  (i) reacting a 4-bromoaniline (compound 1) with a diethyl ethoxymethylenemalonate at 120° C. for 2 hours to obtain a diethyl 2-((4-bromophenylamino)methylene)malonate (compound 2);
  (ii) heating the compound 2 in a dowtherm solvent at 240° C. for 2.5 hours to obtain a ethyl 6-bromo-4-hydroxyquinoline-3-carboxylate (compound 3);
  (iii) reacting the compound 3 with a chlorinating agent at 100° C. for 2 hours to produce an ethyl 6-bromo-4-chloroquinoline-3-carboxylate (compound 4);
  (iv) reacting the compound 4 with an amine selected from the group consisting of -(2-aminoethyl)morpholine, 3-(1H-imidazol-1-yl)propan-1-amine, 3-morpholinopropan-1-amine, 2-(1H-imidazol-1-yl)ethanamine, 3-(1H-pyrrol-1-yl)propan-1-amine, 3-(pyrrolidin-1-yl)propan-1-amine and methylamine in presence of DIPEA to obtain a compound of Formula III;

Formula III

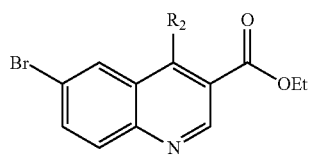

(v) reacting the compound of Formula III as obtained in previous step with a hydrazine monohydrate in ethanol at room temperature to obtain a compound of Formula IV;

Formula IV

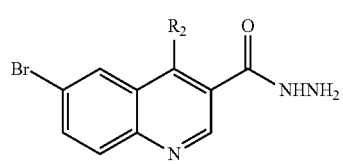

(vi) heating the compound of Formula IV with triethylorthoformate or triethylorthoacetate to obtain a compound of formula IIA;

Formula IIA

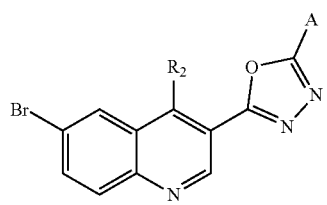

wherein A is H or methyl group, and
  (vii) reacting the compound of Formula IIA with the boronic acid of formula V or formula VI Formula V

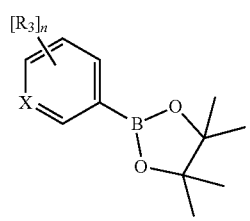

or

Formula VI

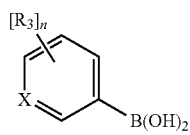

in presence of the 2(M) sodium carbonate solution and the tetrakis(triphenylphosphine)palladium(0) catalyst in a solvent to obtain the compound of formula IA, Formula IA

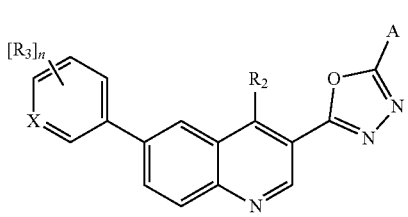

wherein R₂, R₃, X and n are as defined in claim 1.

5. The process of preparation of the compound of Formula I as claimed in claim 3, wherein the solvent is ethanol.

6. The process of preparation of the compound of Formula I as claimed in claim 3, wherein R₁ of the formula I is

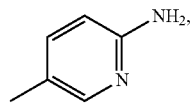

the process comprising:
(i) treating the compound 67 with a 5-(4,4,5,5-tetramethyl-1,3,2-dioxaborolan-2-yl)pyridin-2-amine along with the 2(M) sodium carbonate solution and the tetrakis(triphenylphosphine)palladium(0) catalyst in 1,4-dioxane and DMF at 80° C. for 12 hours to obtain a N-(3-(1H-imidazol-1-yl)propyl)-3-(6-aminopyridin-3-yl)-6-bromoquinolin-4-amine (compound 72); and
(ii) heating the compound 72 with 2-(4-methoxyphenyl)-4,4,5,5-tetramethyl-1,3,2-dioxaborolane, the 2(M) sodium carbonate solution and the tetrakis (triphenylphosphine)palladium(0) catalyst in 1,4-dioxane and DMF at 100° C. for 28 hours to obtain the compound 73.

7. The process of preparation of the compound of Formula I as claimed in claim 3, wherein the compound of formula II is selected from:
6-bromo-N-(2-morpholinoethyl)-3-(1,3,4-oxadiazol-2-yl) quinolin-4-amine (7);
6-bromo-3-(5-methyl-1,3,4-oxadiazol-2-yl)-N-(2-morpholinoethyl)quinolin-4-amine (12);
N-(3-(1H-imidazol-1-yl)propyl)-6-bromo-3-(1,3,4-oxadiazol-2-yl)quinolin-4-amine (17);
6-bromo-N-(3-morpholinopropyl)-3-(1,3,4-oxadiazol-2-yl)quinolin-4-amine (42);
N-(2-(1H-imidazol-1-yl)ethyl)-6-bromo-3-(1,3,4-oxadiazol-2-yl)quinolin-4-amine(48);
5-(4-(3-(1H-imidazol-1-yl)propylamino)-6-bromoquinolin-3-yl)-1,3,4-oxadiazol-2-amine (51);
N-(3-(1H-imidazol-1-yl)propyl)-6-bromo-3-(5-methyl-1,3,4-oxadiazol-2-yl)quinolin-4-amine (53);
N-(3-(1H-pyrrol-1-yl)propyl)-6-bromo-3-(1,3,4-oxadiazol-2-yl)quinolin-4-amine (57);
6-bromo-3-(1,3,4-oxadiazol-2-yl)-N-(3-(pyrrolidin-1-yl) propyl)quinolin-4-amine (61);
N-(3-(1H-imidazol-1-yl)propyl)-3-(6-aminopyridin-3-yl)-6-bromoquinolin-4-amine (72); and
6-bromo-N-methyl-3-(1,3,4-oxadiazol-2-yl)quinolin-4-amine(76).

8. The compound as claimed in claim 1, wherein the compound is stable at pH 7.4 in plasma.

9. The compound as claimed in claim 1, wherein the compound is soluble in water at pH 7.4.

10. The compound as claimed in claim 1, wherein the compound is in a free form or in pharmaceutically acceptable salt form.

11. A method for treatment comprising:
administering a compound of Formula I or salts thereof,

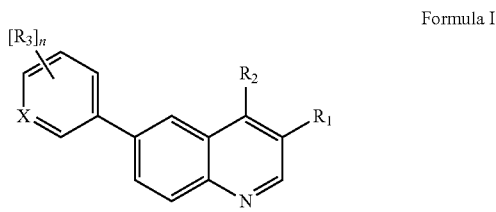

Formula I wherein:
$R_1$ is a substituted aromatic heterocyclic group selected from the group consisting of oxadiazole, pyridyl, amino pyridyl, and furyl, wherein the aromatic heterocyclic group is substituted with —$CH_3$ or —$NH_2$;
$R_2$ is a water soluble or hydrophilic functional group —$NR_5R_6$;
$R_5$ and $R_6$ are either same or different selected from hydrogen atom, a substituted $C_1$-$C_6$ alkyl chain bearing nitrogen containing aromatic heterocyclic group, or a substituted $C_1$-$C_6$ alkyl chain bearing nitrogen containing aliphatic heterocyclic group;
$R_3$ is selected from hydrogen, halogen, hydroxy, cyano, $C_1$-$C_6$ alkyl, $C_1$-$C_6$ haloalkyl, $C_1$-$C_6$ alkoxy, $C_1$-$C_6$ haloalkoxy, amino, alkylamino, acyl amino, or carbamate;
X is CH; and
n is 0-3,
thereby inhibiting or modulating topoisomerase I enzyme to treat diseases and disorders.

12. The method as claimed in claim 11, wherein the diseases and disorders comprise breast cancer.

* * * * *